US012168047B2

(12) United States Patent
Laddy et al.

(10) Patent No.: US 12,168,047 B2
(45) Date of Patent: *Dec. 17, 2024

(54) TUBERCULOSIS ANTIGEN CASSETTES

(71) Applicant: International AIDS Vaccine Initiative, Inc., New York, NY (US)

(72) Inventors: Dominick Laddy, New York, NY (US); Danilo Casimiro, New York, NY (US); Thomas Evans, New York, NY (US); Megan Fitzpatrick Forrest, New York, NY (US); Nathalie Cadieux, New York, NY (US)

(73) Assignee: International AIDS Vaccine Initiative, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/184,869

(22) Filed: Mar. 16, 2023

(65) Prior Publication Data

US 2023/0270834 A1  Aug. 31, 2023

Related U.S. Application Data

(63) Continuation of application No. 16/756,206, filed as application No. PCT/US2018/055817 on Oct. 15, 2018, now Pat. No. 11,638,749.

(60) Provisional application No. 62/573,432, filed on Oct. 17, 2017.

(51) Int. Cl.
*A61K 39/04* (2006.01)
*C07K 14/35* (2006.01)

(52) U.S. Cl.
CPC .............. *A61K 39/04* (2013.01); *C07K 14/35* (2013.01); *C07K 2319/00* (2013.01)

(58) Field of Classification Search
None
See application file for complete search history.

(56) References Cited

U.S. PATENT DOCUMENTS

| | | |
|---|---|---|
| 5,334,498 A | 8/1994 | Roizman et al. |
| 5,593,873 A | 1/1997 | Cochran et al. |
| 5,593,972 A | 1/1997 | Weiner et al. |
| 5,599,544 A | 2/1997 | Cochran et al. |
| 5,676,952 A | 10/1997 | Audonnet et al. |
| 5,720,957 A | 2/1998 | Jones et al. |
| 5,731,188 A | 3/1998 | Cochran et al. |
| 5,741,696 A | 4/1998 | Cochran et al. |
| 5,753,476 A | 5/1998 | Jones et al. |
| 5,804,372 A | 9/1998 | Cochran et al. |
| 5,837,532 A | 11/1998 | Preston et al. |
| 5,843,458 A | 12/1998 | Jones |
| 5,846,806 A | 12/1998 | Jones et al. |
| 5,853,733 A | 12/1998 | Cochran et al. |
| 5,874,279 A | 2/1999 | Cochran et al. |
| 5,906,935 A | 5/1999 | Jones et al. |
| 5,908,780 A | 6/1999 | Jones |
| 5,962,428 A | 10/1999 | Carrano |
| 6,033,671 A | 3/2000 | Frueh et al. |
| 6,103,531 A | 8/2000 | Sedmak et al. |
| 6,140,114 A | 10/2000 | Klatzman et al. |
| 6,410,033 B1 | 6/2002 | Cochran |
| 6,613,892 B2 | 9/2003 | Preston et al. |
| 6,740,324 B2 | 5/2004 | Schall et al. |
| 6,913,751 B2 | 7/2005 | Cochran et al. |
| 6,953,661 B1 | 10/2005 | Diefenbach et al. |
| 7,364,893 B2 | 4/2008 | Wild et al. |
| 7,749,745 B2 | 7/2010 | Johnson et al. |
| 7,892,564 B2 | 2/2011 | Wild et al. |
| 9,249,427 B2 | 2/2016 | Picker et al. |
| 2009/0304750 A1 | 12/2009 | Hone et al. |
| 2011/0117133 A1 | 5/2011 | Shafferman et al. |
| 2013/0136768 A1 | 5/2013 | Picker et al. |
| 2013/0209500 A1 | 8/2013 | Reed et al. |
| 2014/0004151 A1 | 1/2014 | Sette et al. |
| 2014/0141038 A1 | 5/2014 | Picker et al. |
| 2014/0377300 A1 | 12/2014 | Ravi et al. |
| 2015/0165014 A1 | 6/2015 | Tupin et al. |
| 2016/0228528 A1 | 8/2016 | Jungersen et al. |
| 2016/0331823 A1 | 11/2016 | Marchand et al. |
| 2017/0043003 A1 | 2/2017 | Aagaard et al. |
| 2017/0362284 A1 | 12/2017 | Anantha et al. |

FOREIGN PATENT DOCUMENTS

| | | |
|---|---|---|
| WO | 94016737 | 8/1994 |
| WO | 2007058663 | 5/2007 |
| WO | 2008124647 | 10/2008 |
| WO | 2014009438 | 1/2014 |
| WO | 2014063704 | 5/2014 |
| WO | 2014140301 | 9/2014 |
| WO | 2014210018 | 12/2014 |
| WO | 20170087921 | 5/2017 |

(Continued)

OTHER PUBLICATIONS

Angulo et al., "The Major Immediate-Early Gene ie3 of Mouse Cytomegalovirus is Essential for Viral Growth", J. Virol., 2000, 74, 11129-11136.

Asanuma, H., et al., "Frequencies of memory T cells specific for varicella-zoster virus, herpes simplex virus, and cytomegalovirus by intracellular detection of cytokine expression", J Infect Dis, 2000, 181, p. 859-866.

Barnes et al., "Harnessing Endogenous miRNAs to Control Virus Tissue Tropism as a Strategy for Developing Attenuated Virus VaccinesCell Host Microbe", 2008, 4, 239-248.

Brown et al., "Endogenous microRNA can be broadly exploited to regulate transgene expression according to tissue, lineage and differentiation state", Nat. Biotechnol., 2007, 25, 1457-1467.

Dankner, W. M., et al., "Localization of human cytomegalovirus in peripheral blood leukocytes by in situ hybridization", J Infect Dis, 1990, 161, p. 31-36.

(Continued)

*Primary Examiner* — Brian Gangle

(74) *Attorney, Agent, or Firm* — Armstrong Teasdale LLP

(57) ABSTRACT

The present disclosure provides fusion proteins comprising *Mycobacterium tuberculosis* (Mtb) antigens, nucleic acid molecules encoding the same, vectors comprising nucleic acid molecules, compositions comprising the same, and methods of eliciting an immune response against tuberculosis.

7 Claims, No Drawings

Specification includes a Sequence Listing.

(56) References Cited

FOREIGN PATENT DOCUMENTS

WO 2017218867 12/2017

OTHER PUBLICATIONS

Einhorn, L., et al., "Cytomegalovirus infection of human blood cells", J Infect Dis, 1984, 149, p. 207-214.
Gerna, G., et al., "Dendritic-cell infection by human cytomegalovirus is restricted to strains carrying functional UL 131-128 genes and mediates efficient viral antigen presentation to CD8+ T cells", J Gen Virol, 2005, 86, p. 275-284.
Gnann, J. W. Jr., et al., "Inflammatory cells in transplanted kidneys are infected by human cytomegalovirus", Am J Pathol, 1988, 132, p. 239-248.
Hahn, G., et al., "Human cytomegalovirus UL131-128 genes are indispensable for virus growth in endothelial cells and virus transfer to leukocytes", J Virol, 2004, 78, p. 10023-10033.
Hansen et al., "Effector memory T cell responses are associated with protection of rhesus monkeys from mucosal simian immunodeficiency virus challenge", Nat. Med., 2009, 15, 293-299.
Hansen, S. G., et al., "Evasion of CD8+ T cells is critical for superinfection by cytomegalovirus", Science, 2010, 328, . 102-106.
Hansen et al., "Profound early control of highly pathogenic SIV by an effector memory T-cell vaccine", Nature, 2011, 473, 523-527.
Hansen et al., "Immune clearance of highly pathogenic SIV infection", Nature, 2013, 502, 100-104.
Hansen et al., "Cytomegalovirus Vectors Violate CD8+ T Cell Epitope Recognition Paradigms", Science, 2013, 340, 1237874.
Hansen et al., "Broadly targeted CD8+ T cell responses restricted by major histocompatibility complex E", Science, 2016, 351, 714-720.
Harari, A., et al., "Functional heterogeneity of memory CD4+ T cell responses in different conditions of antigen exposure and persistence", J Immunol, 2005, 174, p. 1037-1045.
Harari, A., et al., "Distinct profiles of cytotoxic granules in memory CD8+ T cells correlate with function, differentiation stage, and antigen exposure", J Virol, 2009, 83, p. 2862-2871.
Howell, C. L., et al., "Comparison of rates of virus isolation from leukocyte populations separated from blood by conventional and Ficoll-Paque/Macrodex methods", J Clin Microbiol, 1979, 10, p. 533-537.
Jarvis, M. A., et al., "Mechanisms of human cytomegalovirus persistence and latency", Front Biosci., 2002, 7, d1575-1582.
Lee et al., "MicroRNA Regulation of Oncolytic Herpes Simplex Virus-1 for Selective Killing of Prostate Cancer Cells", Clin. Cancer Res., 2009, 15, 5126-5135.
Lilja, et al., "Efficient replication of rhesus cytomegalovirus variants in multiple rhesus and human cell types", Proc Natl Acad Sci USA, 2008, 105, p. 19950-19955.
Lilja, A. E., et al., "Functional genetic analysis of rhesus cytomegalovirus: Rh-1 is an epithelial cell tropism factor", J Virol, 2008, 82, p. 2170-2181.
Myerson, D., et al., "Widespread presence of histologically occult cytomegalovirus", Hum Pathol, 1984, 15, p. 430-439.
Perez et al., "MicroRNA-mediated species-specific attenuation of influenza A virus", Nat. Biotechnol., 2009, 27, 572-576.
Rue, C. A., et al., "A cyclooxygenase-2 homologue encoded by rhesus cytomegalovirus is a determinant for endothelial cell tropism", Journal of Virology, 2004, 78, p. 12529-12536.
Ryckman, B. J., et al., "Human cytomegalovirus entry into epithelial and endothelial cells depends on genes UL128 to UL150 and occurs by endocytosis and low-pH fusion", J Virol, 2006, 80, p. 710-722.
Ryckman, B. J., et al., "Characterization of the human cytomegalovirus gH/gL/UL128-131 complex that mediates entry into epithelial and endothelial cells", J Virol, 2008, 82, p. 60-70.
Schrier, R. D., et al., "Detection of human cytomegalovirus in peripheral blood lymphocytes in a natural infection", Science, 1985, 230, p. 1048-1051.

Sinzger, C., et al., "Fibroblasts, epithelial cells, endothelial cells and smooth muscle cells are major targets of human cytomegalovirus infection in lung and gastrointestinal tissues", J Gen Virol, 1995, 76, p. 741-750.
Snyder et al., "Cross-presentation of a spread-defective MCMV is sufficient to prime the majority of virus-specific CD8+ T cells", PLoS One, 2010, 5:e9681, doi: 10.1371/journal.pone.0009681.
Sylwester, A. W., et al., "Broadly targeted human cytomegalovirus-specific CD4+ and CD8+ T cells dominate the memory compartments of exposed subjects", J Exp Med, 2005, 202, p. 673-685.
Wang, D., et al., "Human cytomegalovirus UL131 open reading frame is required for epithelial cell tropism", J Virol, 2005, 79, p. 10330-10338.
Wang, D., et al., "Human cytomegalovirus virion protein complex required for epithelial and endothelial cell tropism", Proc Natl Acad Sci USA, 2005, 102, p. 18153-18158.
Singh et al., "Mycobacterium tuberculosis controls microRNA-99b (miR-99b) expression in infected murine dendritic cells to modulate host immunity", J Biol Chem, 2012, 288(7), pp. 5056-5061.
McGregor et al., "Expression of the human cytomegalovirus UL97 gene in a chimeric guinea pig cytomegalovirus (GPCMV) results in viable virus with increased susceptibility to ganciclovir and maribavir", Antiviral Res, 2008, 78(3), pp. 250-259.
Hoft et al., "Safety and Immunogenicity of the Recombinant BCG Vaccine AERAS-422 in Healthy BCG-naive Adults: A Randomized, Active-controlled, First-in-human Phase 1 Trail", EBioMedicine, 2016, 7, pp. 278-286.
Velmurugan et al., "Nonclinical Development of BCG Replacement Vaccine Candidates", Vaccines, 2013, 1(2), pp. 120-138.
Graves et al., "Tuberculosis Vaccines: Review of Current Development Trends and Future Challenges", J Bioterr Biodef, 2011, S1-009.
Da Costa et al., "Tuberculosis vaccines-state of the art, and novel approaches to vaccine development", Int J Infect Dis, 2015, 32, pp. 5-12.
Zvi et al., "Whole genome identification of *Mycobacterium tuberculosis* vaccine candidates by comprehensive data mining and bioinformatic analyses", BMC Med Genomics, 2008, 1(18), pp. 1-25.
De Sousa et al., "Immunogenicity of a Fusion Protein Containing Immunodominant Epitopes of Ag85C, MPT51, and HspX from *Mycobacterium tuberculosis* in Mice and Active TB Infection", Plos ONE, 2012, 7(10), e47781.
Langermans et al., "Protection of macaques against *Mycobacterium tuberculosis* infection by a subunit vaccine based on a fusion protein of antigen 85B and ESAT-6", Vaccine, 2005, 23, pp. 2740-2750.
Luo et al., "Fusion Protein Ag85B-MPT64(190-198)-Mtb8.4 Has Higher Immunogenicity Than Ag85B With Capacity to Boost BCG-primed Immunity Against *Mycobacterium Tuberculosis* in Mice", Vaccine, 2009, 27, pp. 6179-6185.
Non-Final Office Action mailed Feb. 28, 2018 for U.S. Appl. No. 15/628,921 (190151.01501 (3031).
Final Office Action mailed Jan. 25, 2019 for U.S. Appl. No. 15/628,921.
Non-Final Office Action mailed Aug. 20, 2019 for U.S. Appl. No. 15/628,921.
Non-Final Office Action mailed May 14, 2020 for U.S. Appl. No. 15/628,921.
Leung-Theung-Long et al., "A Novel MVA-Based Multiphasic Vaccine for Prevention or Treatment of Tuberculosis Induces Broad and Multifunctional Cell-Mediated Immunity in Mice and Primates", PLoS One, 2015, 10(11), e0143552.
Leung-Theung-Long, "MVA Technology in the Development of Highly Complexed TB Vaccine Candidates", TBVI Symposium, Les Diablerets, Feb. 3, 2016.
Final Office Action mailed Dec. 4, 2020 for U.S. Appl. No. 15/628,921.
Notice of Allowance dated Apr. 2, 2021 in related U.S. Appl. No. 15/628,921.
Brennan, "The Enigmatic PE/PPE Multigene Family of Mycobacteria and Tuberculosis Vaccination", Infection and Immunity, 2017, 85(6), pp. 1-8.

(56) References Cited

OTHER PUBLICATIONS

Non-Final Office Action dated Sep. 12, 2022 in related U.S. Appl. No. 17/365,509.

Final Office Action dated Mar. 8, 2023 in related U.S. Appl. No. 17/365,509.

Olsen et al., "Protection of Mice with a Tuberculosis Subunit Vaccine Based on a Fusion Protein of Antigen 85B and ESAT-6", Infection and Immunity, 2001, 69(5), pp. 2773-2778.

Mu et al., "Immunization with a bivalent adenovirus-vectored Tuberculosis vaccine provides markedly improved protection over its monovalent counterpart against pulmonary tuberculosis", Molecular Therapy, 2009, 17(6), pp. 1093-1100.

Havenga et al., "Novel replication-incompetent adenoviral B-group vectors: high vector stability and yield in PER.C6 cells", Journal of General Virology, 2006, 87, pp. 2135-2143.

Sun et al., "Novel recombinant BCG expressing perfringolysin O and the over-expression of key immunodominant antigens; preclinical characterization, safety and protection against challenge with *Mycobacterium tuberculosis*", Vaccine, 2009, 27, pp. 4412-4423.

Zhang et al., "Effects of the fusion design and immunization route on the immunogenicity of Ag85A—Mtb32 in adenoviral vectored tuberculosis vaccine", Human Vaccines and Immunotherapeutics, 2015, 11(7), pp. 1803-1813.

Bennekov et al., "Alteration of epitope recognition pattern in Ag85B and ESAT-6 has a profound influence on vaccine-induced protection against *Mycobacterium tuberculosis*", Eur J Immunol, 2006, 36, pp. 3346-3355.

Final Office Action dated May 16, 2023 in related U.S. Appl. No. 17/365,509.

Hansen et al., "Prevention of tuberculosis in rhesus macaques by a cytomegalovirus-based vaccine", Nature Medicine, 2018, 24(2), pp. 130-143.

Notice of Allowance dated Jul. 28, 2023 in related U.S. Appl. No. 17/365,509.

SEQUENCE LISTING

```
Sequence total quantity: 71
SEQ ID NO: 1            moltype = DNA  length = 300
FEATURE                 Location/Qualifiers
misc_feature            1..300
                        note = Rv3872 (PE35)
source                  1..300
                        mol_type = other DNA
                        organism = synthetic construct
SEQUENCE: 1
atggagaaga tgagccacga ccccatcgcc gccgacatcg gcacccaggt gagcgacaac   60
gccctgcacg gcgtgaccgc cggcagcacc gccctgacca gcgtgaccgg cctggtgccc  120
gccggcgccg acgaggtgag cgcccaggcc gccaccgcct tcaccagcga gggcatccag  180
ctgctggcca gcaacgccag cgcccaggac cagctgcaca gggccggcga ggccgtgcag  240
gacgtggcca ggacctacag ccagatcgac gacggcgccg ccggcgtgtt cgccgagtga  300

SEQ ID NO: 2            moltype = AA  length = 99
FEATURE                 Location/Qualifiers
REGION                  1..99
                        note = Rv3872 (PE35)
source                  1..99
                        mol_type = protein
                        organism = synthetic construct
SEQUENCE: 2
MEKMSHDPIA ADIGTQVSDN ALHGVTAGST ALTSVTGLVP AGADEVSAQA ATAFTSEGIQ   60
LLASNASAQD QLHRAGEAVQ DVARTYSQID DGAAGVFAE                          99

SEQ ID NO: 3            moltype = DNA  length = 300
FEATURE                 Location/Qualifiers
misc_feature            1..300
                        note = Rv1788 (PE18)
source                  1..300
                        mol_type = other DNA
                        organism = synthetic construct
SEQUENCE: 3
atgagcttcg tgaccaccca gcccgaggcc ctggccgccg ccgccggcag cctgcagggc   60
atcggcagcg ccctgaacgc ccagaacgcc gccgccgcca cccccaccac cggcgtggtg  120
cccgccgccg ccgacgaggt gagcgccctg accgccgcc agttcgccgc ccacgcccag  180
atctaccagg ccgtgagcgc ccaggccgcc gccatccacg agatgttcgt gaacaccctg  240
cagatgagca gcggcagcta cgccgccacc gaggccgcca acgccgccgc cgccggctga  300

SEQ ID NO: 4            moltype = AA  length = 99
FEATURE                 Location/Qualifiers
REGION                  1..99
                        note = Rv1788 (PE18)
source                  1..99
                        mol_type = protein
                        organism = synthetic construct
SEQUENCE: 4
MSFVTTQPEA LAAAAGSLQG IGSALNAQNA AAATPTTGVV PAAADEVSAL TAAQFAAHAQ   60
IYQAVSAQAA AIHEMFVNTL QMSSGSYAAT EAANAAAAG                          99

SEQ ID NO: 5            moltype = DNA  length = 234
```

| FEATURE | Location/Qualifiers |
|---|---|
| misc_feature | 1..234 |
| | note = Rv3893c (PE36) |
| source | 1..234 |
| | mol_type = other DNA |
| | organism = synthetic construct |

SEQUENCE: 5

```
atggtgtgga gcgtgcagcc cgaggccgtg ctggccagcg ccgccgccga gagcgccatc    60
agcgccgaga ccgaggccgc cgccgccggc gccgccccg ccctgctgag caccacccc    120
atgggcggcg accccgacag cgccatgttc agcgccgcc tgaacgcctg cggcgccagc    180
tacctgggcg tggtggccga gcacgccagc cagaggggcc tgttcgccgg ctga    234
```

| SEQ ID NO: 6 | moltype = AA length = 77 |
|---|---|
| FEATURE | Location/Qualifiers |
| REGION | 1..77 |
| | note = Rv3893c (PE36) |
| source | 1..77 |
| | mol_type = protein |
| | organism = synthetic construct |

SEQUENCE: 6

```
MVWSVQPEAV LASAAAESAI SAETEAAAAG AAPALLSTTP MGGDPDSAMF SAALNACGAS    60
YLGVVAEHAS QRGLFAG                                                  77
```

| SEQ ID NO: 7 | moltype = DNA length = 309 |
|---|---|
| FEATURE | Location/Qualifiers |
| misc_feature | 1..309 |
| | note = Rv0285 (PE5) |
| source | 1..309 |
| | mol_type = other DNA |
| | organism = synthetic construct |

SEQUENCE: 7

```
atgaccctga gggtggtgcc cgagggcctg gccgccgcca gcgccgccgt ggaggccctg    60
accgccaggt tggccgccgc ccacgccagc gccgccccg tgatcaccgc cgtggtgccc    120
cccgccgcca cccccgtgag cctgcagacc gccgccggct tcagcgccca gggcgtggag    180
cacgccgtgg tgaccgccga gggcgtggag gagctgggca gggccggcgt gggcgtgggc    240
gagagcggcg ccagctacct ggccggcgac gccgccgccg ccgccaccta cggcgtggtg    300
ggcggctga                                                           309
```

| SEQ ID NO: 8 | moltype = AA length = 102 |
|---|---|
| FEATURE | Location/Qualifiers |
| REGION | 1..102 |
| | note = Rv0285 (PE5) |
| source | 1..102 |
| | mol_type = protein |
| | organism = synthetic construct |

SEQUENCE: 8

```
MTLRVVPEGL AAASAAVEAL TARLAAAHAS AAPVITAVVP PAADPVSLQT AAGFSAQGVE    60
HAVVTAEGVE ELGRAGVGVG ESGASYLAGD AAAAATYGVV GG                      102
```

| SEQ ID NO: 9 | moltype = DNA length = 303 |
|---|---|
| FEATURE | Location/Qualifiers |
| misc_feature | 1..303 |
| | note = Rv1818c (PE_PGRS33) |
| source | 1..303 |
| | mol_type = other DNA |
| | organism = synthetic construct |

SEQUENCE: 9

```
atgagcttcg tggtgaccat ccccgaggcc ctggccgccg tggccaccga cctggccggc    60
atcggcagca ccatcggcac cgccaacgcc gccgccgcc tgcccaccac caccgtgctg    120
gccgccgccg ccgacgaggt gagcgccgcc atggccgcc tgttcagcgg ccacgcccag    180
gcctaccagg ccctgagcgc ccaggccgcc ctgttccacg agcagttcgt gagggccctg    240
accgccggcg ccggcagcta cgccgccgcc gaggccgcca gcgccgcccc cctggagggc    300
tga                                                                 303
```

| SEQ ID NO: 10 | moltype = AA length = 100 |
|---|---|
| FEATURE | Location/Qualifiers |
| REGION | 1..100 |
| | note = Rv1818c (PE_PGRS33) |
| source | 1..100 |
| | mol_type = protein |
| | organism = synthetic construct |

SEQUENCE: 10

```
MSFVVTIPEA LAAVATDLAG IGSTIGTANA AAAVPTTTVL AAAADEVSAA MAALFSGHAQ    60
AYQALSAQAA LFHEQFVRAL TAGAGSYAAA EAASAAPLEG                         100
```

| SEQ ID NO: 11 | moltype = DNA length = 333 |
|---|---|
| FEATURE | Location/Qualifiers |
| misc_feature | 1..333 |
| | note = Rv0159c (PE3) |

```
source                    1..333
                          mol_type = other DNA
                          organism = synthetic construct
SEQUENCE: 11
atgagctacg tgatcgccgc ccccgagatg ctggccacca ccgccgccga cgtggacggc    60
atcggcagcg ccatcagggc cgccagcgcc agcgccgccg gccccaccac cggcctgctg   120
gccgccgccg ccgacgaggt gagcagcgcc gccgccgccc tgttcagcga gtacgccagg   180
gagtgccagg aggtgctgaa gcaggccgcc gccttccacg gcgagttcac cagggccctg   240
gccgccgccg gcgccgccta cgcccaggcc gaggccagca caccgccgc catgagcggc   300
accgccggca gcggcgc cctgggcagc tga                                    333

SEQ ID NO: 12             moltype = AA   length = 110
FEATURE                   Location/Qualifiers
REGION                    1..110
                          note = Rv0159c (PE3)
source                    1..110
                          mol_type = protein
                          organism = synthetic construct
SEQUENCE: 12
MSYVIAAPEM LATTAADVDG IGSAIRAASA SAAGPTTGLL AAAADEVSSA AAALFSEYAR    60
ECQEVLKQAA AFHGEFTRAL AAAGAAYAQA EASNTAAMSG TAGSSGALGS              110

SEQ ID NO: 13             moltype = DNA   length = 333
FEATURE                   Location/Qualifiers
misc_feature              1..333
                          note = Rv1172c (PE12)
source                    1..333
                          mol_type = other DNA
                          organism = synthetic construct
SEQUENCE: 13
atgagcttcg tgttcgccgc ccccgaggcc ctggccgccg ccgccgccga catggccggc    60
atcggcagca ccctgaacgc cgccaacgtg gtggccgccg tgcccaccac cggcgtgctg   120
gccgccgccg ccgacgaggt gagcacccag gtggccgccc tgctgagcgc ccacgcccag   180
ggctaccagc agctgagcag gcagatgatg accgccttcc acgaccagtt cgtgcaggcc   240
ctgagggcca gcgccgacgc ctacgccacc gccgaggcca gcgccgccca gaccatggtg   300
aacgccgtga acgcccccgc cagggccctg tga                                 333

SEQ ID NO: 14             moltype = AA   length = 110
FEATURE                   Location/Qualifiers
REGION                    1..110
                          note = Rv1172c (PE12)
source                    1..110
                          mol_type = protein
                          organism = synthetic construct
SEQUENCE: 14
MSFVFAAPEA LAAAAADMAG IGSTLNAANV VAAVPTTGVL AAAADEVSTQ VAALLSAHAQ    60
GYQQLSRQMM TAFHDQFVQA LRASADAYAT AEASAAQTMV NAVNAPARAL              110

SEQ ID NO: 15             moltype = DNA   length = 2097
FEATURE                   Location/Qualifiers
misc_feature              1..2097
                          note = Rv3872-Rv1788-Rv3893c-Rv0285-Rv1818c-Rv0159c-Rv1172c
                          fusion protein
source                    1..2097
                          mol_type = other DNA
                          organism = synthetic construct
SEQUENCE: 15
atggagaaga tgagccacga ccccatcgcc gccgacatcg gcacccaggt gagcgacaac    60
gccctgcacg gcgtgaccgc cggcagcacc gccctgacca gcgtgaccgg cctggtgccc   120
gccggccg acgaggtgag cgccctgacc gccgccagt cgccgccca cgcccagatc   180
ctgctgccca gcaacgccag cgcccaggac cagctgcaca gggccggcga ggccgtgcag   240
gacgtggcca ggacctacag ccagatcgac gacggcgccc ccggcgtgtt cgccgagatg   300
agcttcgtga ccacccagcc cgaggccctg gccgccgccg ccggcagcct gcagggcatc   360
ggcagcgccc tgaacgccca gaaccgccgc cgccgccacc cgtggtgccc   420
gccgccgccg acgaggtgag cgccctgacc gccgcccagt cgccgcccca cgcccagatc   480
taccaggccc tgagccccca ggccgccgcc atccacgaga tgttcgtgaa cacccctgcag   540
atgagcagcg gcagctacgc cgccaccgag ccgccaacg ccgccgccgc cggcgccgcc   600
gccatggtgt ggacgtgca gccgaggcc gtgctggcca gcgccgccgc cgagagcgcc   660
atcagcgccg agaccgaggc cgccgccgcc ccggccgccg ccgccctgct gagcaccacc   720
cccatgggcg cgaccccga cagcgccatg ttcagcgccg ccctgaacgc ctgcggcgcc   780
agctacctgg gcgtggtggc cgagcacgcc agcagaggg gcctgttcgc cggcatgacc   840
ctgagggtgt gcccgagggg cctggccgcc gcagcgccg cgtgaggc cctgaccgcc   900
aggctggccg ccgcccacgc cagcgccgcc ccgtgatca ccgccgtggt gcccccgcc   960
gccgaccccg tgagcctgca ggccgccgcc ggcttcagcg gcatgacgcc  1020
gtggtgaccg ccgagggcgt ggaggagctg gcagggccg gcgtgggcgt gggcgagagc  1080
ggcgccagct acctggccgg cgacgccgcc gccgcgcca cctacggcgt ggtgggcggc  1140
atgagcttcg tggtgaccat ccccgaggcc ctggccgccg tggccaccga cctgccggc  1200
atcggcagca ccatcggcac cgccaacgcc gccgccgccg tgcccaccac caccgtgctg  1260
gccgccgccg ccgacgaggt gagcgccgcc atggccgccc tgttcagcgg ccacgcccag  1320
```

-continued

```
gcctaccagg ccctgagcgc ccaggccgcc ctgttccacg agcagttcgt gagggccctg   1380
accgccggcg ccggcagcta cgccgccatg agctacgtga tcgccgcccc cgagatgctg   1440
gccaccaccg ccgccgacgt ggacggcatc ggcagcgcca tcagggccgc cagcgccagc   1500
gccgccggcc ccaccaccgg cctgctggcc gccgccgccg acgaggtgag cagcgccgcc   1560
gccgccctgt tcagcgagta cgccagggag tgccaggagg tgctgaagca ggccgccgcc   1620
ttccacggcg agttcaccag ggccctggcc gccgccggcc ccgcctacgc ccaggccgag   1680
gccagcaaca ccgccgccat gagcggcacc gccggcagca gcggcgccct gggcagcatg   1740
agcttcgtgt tcgccgcccc cgaggccctg gccgccgccg ccgccgacat ggccggcatc   1800
ggcagcaccc tgaacgccgc caacgtggtg gccgccgtgc ccaccaccgg cgtgctggcc   1860
gccgccgccg acgaggtgag cacccaggtg gccgccctgc tgagccacgc ccagcaggtg   1920
taccagcagc tgagcaggca gatgatgacc gccttccacg accagttcgt gcaggccctg   1980
agggccagcg ccgacgccta cgccaccgcc gaggccagcg ccgcccagac catggtgaac   2040
gccgtgaacc ccccgccag ggccctgtac ccctacgacg tgcccgacta cgcctga      2097
```

```
SEQ ID NO: 16           moltype = AA  length = 698
FEATURE                 Location/Qualifiers
REGION                  1..698
                        note = Rv3872-Rv1788-Rv3893c-Rv0285-Rv1818c-Rv0159c-Rv1172c
                         fusion protein
source                  1..698
                        mol_type = protein
                        organism = synthetic construct
SEQUENCE: 16
MEKMSHDPIA ADIGTQVSDN ALHGVTAGST ALTSVTGLVP AGADEVSAQA ATAFTSEGIQ    60
LLASNASAQD QLHRAGEAVQ DVARTYSQID DGAAGVFAEM SFVTTQPEAL AAAAGSLQGI   120
GSALNAQNAA AATPTTGVVP AAADEVSALT AAQFAAHAQI YQAVSAQAAA IHEMFVNTLQ   180
MSSGSYAATE AANAAAAGAA AMVWSVQPEA VLASAAAESA ISAETEAAAA GAAPALLSTT   240
PMGGDPDSAM FSAALNACGA SYLGVVAEHA SQRGLFAGMT LRVVPEGLAA ASAAVEALTA   300
RLAAAHASAA PVITAVVPPA ADPVSLQTAA GFSAQGVEHA VVTAEGVEEL GRAGVGVGES   360
GASYLAGDAA AAATYGVVGG MSFVVTIPEA LAAVATDLAG IGSTIGTANA AAAVPTTTVL   420
AAAAADEVSAA MAALFSGHAQ AYQALSAQAA LFHEQFVRAL TAGAGSYAAM SYVIAAPEML   480
ATTAADVDGI GSAIRAASAS AAGPTTGLLA AAADEVSSAA AALFSEYARE CQEVLKQAAA   540
FHGEFTRALA AAGAAYAQAE ASNTAAMSGT AGSSGALGSM SFVFAAPEAL AAAAADMAGI   600
GSTLNAANVV AAVPTTGVLA AAADEVSTQV AALLSAHAQQ YQQLSRQMMT AFHDQFVQAL   660
RASADAYATA EASAAQTMVN AVNAPARALY PYDVPDYA                          698
```

```
SEQ ID NO: 17           moltype = AA  length = 9
FEATURE                 Location/Qualifiers
REGION                  1..9
                        note = Hemagglutinin tag
source                  1..9
                        mol_type = protein
                        organism = synthetic construct
SEQUENCE: 17
YPYDVPDYA                                                             9
```

```
SEQ ID NO: 18           moltype = DNA  length = 543
FEATURE                 Location/Qualifiers
misc_feature            1..543
                        note = Rv3873 (PPE68)
source                  1..543
                        mol_type = other DNA
                        organism = synthetic construct
SEQUENCE: 18
atgctgtggc acgccatgcc ccccgagctg aacaccgcca ggctgatggc cggcgccggc    60
cccgcccca tgctggccgc cgccgccggc tggcagaccc tgagcgccgc cctggacgcc   120
caggccgtgg agctgaccgc caggctgaac agcctgggcg aggcctggac cggcggcggc   180
agcgacaagg ccctggccgc cgccacccc atggtggtgt ggctgcagac cgccagcacc   240
caggccaaga ccagggccat gcaggccacc gcccaggccg ccgcctacgc ccaggccatg   300
gccaccaccc ccagcctgcc cgagatcgcc gccaaccaca tcacccaggc cgtgctgacc   360
gccaccaact tcttcggcat caacaccatc cccatcgccc tgaccgagat ggactacttc   420
atcaggatgt ggaaccaggc cgccctggcc atggaggtgt accaggccga accgccgtg   480
aacaccctgt tcgagaagct ggagcccatg gccagcatcc tggaccccgg cgccagccag   540
tga                                                                 543
```

```
SEQ ID NO: 19           moltype = AA  length = 180
FEATURE                 Location/Qualifiers
REGION                  1..180
                        note = Rv3873 (PPE68)
source                  1..180
                        mol_type = protein
                        organism = synthetic construct
SEQUENCE: 19
MLWHAMPPEL NTARLMAGAG PAPMLAAAAG WQTLSAALDA QAVELTARLN SLGEAWTGGG    60
SDKALAAATP MVVWLQTAST QAKTRAMQAT AQAAAYTQAM ATTPSLPEIA ANHITQAVLT   120
ATNFFGINTI PIALTEMDYF IRMWNQAALA MEVYQAETAV NTLFEKLEPM ASILDPGASQ   180
```

```
SEQ ID NO: 20           moltype = DNA  length = 543
FEATURE                 Location/Qualifiers
```

```
misc_feature            1..543
                        note = Rv1387 (PPE20)
source                  1..543
                        mol_type = other DNA
                        organism = synthetic construct
SEQUENCE: 20
atgaccgagc cctggatcgc cttccccccc gaggtgcaca cgccatgct gaactacggc      60
gccggcgtgg cccccatgct gatcagcgcc acccagaacg gcgagctgag cgcccagtac   120
gccgaggccg ccagcgaggt ggaggagctg ctgggcgtgg tggccagcga gggctggcag   180
ggccaggccg ccgaggcctt cgtggccgcc tacatgccct tcctggcctg gctgatccag   240
gccagcgccg actgcgtgga gatggccgcc cagcagcacg tggtgatcga ggcctacacc   300
gccgccgtgg agctgatgcc cacccaggtg gagctggccg ccaaccagat caagctggcc   360
gtgctggtgg ccaccaactt cttcggcatc aacaccatcc ccatcgccat caacgaggcc   420
gagtacgtgg agatgtgggt gagggccgcc accaccatgg ccacctacag caccgtgagc   480
aggagcgccc tgagcgccat gccccacacc agccccccc cctgatcct gaagagcgac      540
tga                                                                 543

SEQ ID NO: 21           moltype = AA   length = 180
FEATURE                 Location/Qualifiers
REGION                  1..180
                        note = Rv1387 (PPE20)
source                  1..180
                        mol_type = protein
                        organism = synthetic construct
SEQUENCE: 21
MTEPWIAFPP EVHSAMLNYG AGVGPMLISA TQNGELSAQY AEAASEVEEL LGVVASEGWQ    60
GQAAEAFVAA YMPFLAWLIQ ASADCVEMAA QQHVVIEAYT AAVELMPTQV ELAANQIKLA   120
VLVATNFFGI NTIPIAINEA EYVEMWVRAA TTMATYSTVS RSALSAMPHT SPPPLILKSD   180

SEQ ID NO: 22           moltype = DNA   length = 543
FEATURE                 Location/Qualifiers
misc_feature            1..543
                        note = Rv3892c (PPE69)
source                  1..543
                        mol_type = other DNA
                        organism = synthetic construct
SEQUENCE: 22
atgcccgacc ccggctgggc cgccaggacc cccgaggcca acgacctgct gctgaccgcc      60
ggcaccggcg tgggcaccca cctggccaac cagaccgcct ggaccaccct gggcgccagc   120
caccacgcca cgcggcgtgg ccagcgccatc aacaccgccg ccaccgccgc cagctggctg   180
ggcgtgggca cgccgccag cgccctgaac gtgaccatgc tgaacgccac cctgcacggc   240
ctggccggct ggtggacgt gaagcccgcc gtggtgagca ccgccatcgc cgccttcgag   300
accgccaacg ccgccatgag gcccgccccc gagtgcatgg agaacaggga cgagtggggc   360
gtggacaacg ccatcaaccc cagcgtgctg tggaccctga cccccaggat cgtgagcctg   420
gacgtggagt acttcggcgt gatgtggccc aacaacgccg ccgtgggcgc cacctacggc   480
ggcgtgctgg ccgccctggc cgagagcctg gccatccccc cccccgtggc caccatgggc   540
tga                                                                 543

SEQ ID NO: 23           moltype = AA   length = 180
FEATURE                 Location/Qualifiers
REGION                  1..180
                        note = Rv3892c (PPE69)
source                  1..180
                        mol_type = protein
                        organism = synthetic construct
SEQUENCE: 23
MPDPGWAART PEANDLLLTA GTGVGTHLAN QTAWTTLGAS HHASGVASAI NTAATAASWL    60
GVGSAASALN VTMLNATLHG LAGWVDVKPA VVSTAIAAFE TANAAMRPAP ECMENRDEWG   120
VDNAINPSVL WTLTPRIVSL DVEYFGVMWP NNAAVGATYG GVLAALAESL AIPPPVATMG   180

SEQ ID NO: 24           moltype = DNA   length = 543
FEATURE                 Location/Qualifiers
misc_feature            1..543
                        note = Rv1789 (PPE26)
source                  1..543
                        mol_type = other DNA
                        organism = synthetic construct
SEQUENCE: 24
atggacttcg gcgccctgcc ccccgaggtg aacagcgtga ggatgtacgc cggccccggc      60
agcgccccca tggtgccgc cgccagcgcc tggaacggcc tggccgccga gctgagcagc   120
gccgccaccg gctacgagac cgtgatcacc cagctgagca gcgagggctg gctgggcccc   180
gccagcgccg ccatggccga ggccgtggcc cctacgtgg cctggatgag cgccgccgcc   240
gccaggccg agcaggccgc cacccaggcc agggccgccg ccgccgcctt cgaggccgcc   300
ttcgccgacc ccgtgccccc ccccctgatc gccgccaaca gggccagcct gatgcagctg   360
atcagcacca acgtgttcgg ccagaacacc agcgccatcg ccgccgccga ggcccagtac   420
ggcgagatgt gggcccagga cagcgccgcc atgtacgcct acgccggcag cagcgccagc   480
gccagcgccg tgaccccctt cagcacccc cccccagatcg ccaaccccac cgcccagggc   540
tga                                                                 543
```

| SEQ ID NO: 25 | moltype = AA length = 180 |
| --- | --- |
| FEATURE | Location/Qualifiers |
| REGION | 1..180 |
| | note = Rv1789 (PPE26) |
| source | 1..180 |
| | mol_type = protein |
| | organism = synthetic construct |

SEQUENCE: 25

```
MDFGALPPEV NSVRMYAGPG SAPMVAAASA WNGLAAELSS AATGYETVIT QLSSEGWLGP  60
ASAAMAEAVA PYVAWMSAAA AQAEQAATQA RAAAAAFEAA FAATVPPPLI AANRASLMQL 120
ISTNVFGQNT SAIAAAEAQY GEMWAQDSAA MYAYAGSSAS ASAVTPFSTP PQIANPTAQG 180
```

| SEQ ID NO: 26 | moltype = DNA length = 543 |
| --- | --- |
| FEATURE | Location/Qualifiers |
| misc_feature | 1..543 |
| | note = Rv1800 (PPE28) |
| source | 1..543 |
| | mol_type = other DNA |
| | organism = synthetic construct |

SEQUENCE: 26

```
atgctgccca acttcgccgt gctgccccc gaggtgaaca cgccagggt gttcgccggc   60
gcggcagcg cccccatgct ggccgccagc gccgcctggc cagcgagctg             120
cactgcgccg ccatgagctt cggcagcgtg accagcggcc tggtggtggg ctggtggcag 180
ggcagcgcca cgccgccat ggtggacgcc gccgccagct acatcggctg gctgagcacc  240
agcgccgccc acgccgaggg cgccgccggc ctggccaggg ccgccgtgag cgtgttcgag 300
gaggccctgg ccgccaccgt gcaccccgcc atggtgccg ccaacaggcc cgaggtggcc  360
agcctggtgg ccagcaacct gttcggccag aacgcccccg ccatcgccgc cctggagagc 420
ctgtacgagt gcatgtgggc ccaggacgcc gccgccatgg ccggctacta cgtgggcgcc 480
agcgccgtgg ccacccagct ggccagctgg ctgcagaggc tgcagagcat ccccggcgcc 540
tga                                                              543
```

| SEQ ID NO: 27 | moltype = AA length = 180 |
| --- | --- |
| FEATURE | Location/Qualifiers |
| REGION | 1..180 |
| | note = Rv1800 (PPE28) |
| source | 1..180 |
| | mol_type = protein |
| | organism = synthetic construct |

SEQUENCE: 27

```
MLPNFAVLPP EVNSARVFAG AGSAPMLAAA AAWDDLASEL HCAAMSFGSV TSGLVVGWWQ  60
GSASAAMVDA AASYIGWLST SAAHAEGAAG LARAAVSVFE EALAATVHPA MVAANRAQVA 120
SLVASNLFGQ NAPAIAALES LYECMWAQDA AAMAGYYVGA SAVATQLASW LQRLQSIPGA 180
```

| SEQ ID NO: 28 | moltype = DNA length = 543 |
| --- | --- |
| FEATURE | Location/Qualifiers |
| misc_feature | 1..543 |
| | note = Rv1039c (PPE15) |
| source | 1..543 |
| | mol_type = other DNA |
| | organism = synthetic construct |

SEQUENCE: 28

```
atggacttcg cgccctgcc ccccgagatc aacagcgcca ggatgtacgc cggcgccggc   60
gccggcccca tgatggccgc cggcgccgcc tggaacggcc tggccgccga gctgggcacc 120
accgccgcca gctacgagag cgtgatcacc aggctgacca ccgagagctg gatgggcccc 180
gccagcatgg ccatggtggc cgccgcccag ccctacctgg cctggctgac ctacaccgcc 240
gaggccgccg cccacgccgg cagccaggcc atgccagcc ccgccgccta cgaggccgcc  300
tacgccatga ccgtgccccc cgaggtggtg gccgccaaca gggccctgct ggccgccctg 360
gtggccacca acgtgctggg catcaacacc ccgccatca tggccaccga ggccctgtac  420
gccgagatgt gggcccagga cgccctggcc atgtacggct acgccgccgc cagcggcgcc 480
gccggcatgc tgcagcccct gagccccccc agccagacca ccaaccccgg cggcctggcc 540
tga                                                              543
```

| SEQ ID NO: 29 | moltype = AA length = 180 |
| --- | --- |
| FEATURE | Location/Qualifiers |
| REGION | 1..180 |
| | note = Rv1039c (PPE15) |
| source | 1..180 |
| | mol_type = protein |
| | organism = synthetic construct |

SEQUENCE: 29

```
MDFGALPPEI NSARMYAGAG AGPMMAAGAA WNGLAAELGT TAASYESVIT RLTTESWMGP  60
ASMAMVAAAQ PYLAWLTYTA EAAAHAGSQA MASAAAYEAA YAMTVPPEVV AANRALLAAL 120
VATNVLGINT PAIMATEALY AEMWAQDALA MYGYAAASGA AGMLQPLSPP SQTTNPGGLA 180
```

| SEQ ID NO: 30 | moltype = DNA length = 1650 |
| --- | --- |
| FEATURE | Location/Qualifiers |
| misc_feature | 1..1650 |
| | note = Rv3873-Rv1387-Rv3892c fusion protein |
| source | 1..1650 |

```
                    mol_type = other DNA
                    organism = synthetic construct
SEQUENCE: 30
atgctgtggc acgccatgcc ccccgagctg aacaccgcca ggctgatggc cggcgccggc    60
cccgccccca tgctggccgc cgccgccggc tggcagaccc tgagcgccgc cctggacgcg   120
caggccgtgg agctgacccg caggctgaac agcctgggcg aggcctggac cggcggcggc   180
agcgacaagg ccctggccgc cgccacccccc atggtggtgt ggctgcagac cgccagcacc   240
caggccaaga ccagggccat gcaggccacc gcccaggccg ccgcctacac ccaggccatg   300
gccaccaccc cagcctgcc cgagatcgcc gccaaccaca tcacccaggc cgtgctgacc   360
gccaccaact tcttcggcat caacaccatc cccatcgccc tgaccgagat ggactacttc   420
atcaggatgt ggaaccaggc cgccctggcc atggaggtgt accaggccga gaccgccgtg   480
aacaccctgt tcgagaagct ggagcccatg gccagcatcc tggaccccgg cgccagccag   540
atgaccgagc cctggatcgc cttccccccc gaggtgcaca gcgccatgct gaactacggc   600
gccggcgtgg gccccatgct gatcagcgcc acccagaacg gcgagctgag cgcccagtac   660
gccgaggccg ccagcgaggt ggaggagctg ctgggcgtgg tggccagcga gggctggcag   720
ggccaggccg ccgaggcctt cgtggccgcc tacatgcctt tcctggcctg gctgatccag   780
gccagcgccg actgcgtgga gatggccgcc cagcagcacg tggtgatcga ggcctacacc   840
gccgcggtgg agctgatgcc cacccaggtg gagctgggcc caaccagat caagctggcc   900
gtgctggtgg ccaccaactt cttcggcatc aacaccatcc ccatcgccat caacgaggcc   960
gagtacgtgg agatgtgggt gagggccgcc accaccatgg ccacctacag caccgtgagc  1020
aggagcgccc tgagcgccat gccccacacc agccccccc cctgatcct gaagagcgac  1080
atgcccgacc ccggctgggc cgccaggacc cccgaggcca acgacctgct gctgaccgcc  1140
ggcaccggcg tgggcaccca cctgccaac cagaccgcct ggaccaccct gggcgccagc  1200
caccacgcca gcggcgtggc cagcgccatc aacaccgccg ccaccgccgc cagctggctg  1260
ggcgtgggca gcgccgccag cgccctgaac gtgaccatgc tgaacgccac cctgcacggc  1320
ctggccggct gggtgacgt gaagcccgcc gtggtgagca ccgccatcgc cgccttcgag  1380
accgccaacg ccgccatgag gcccgcccccc gagtgcatgg agaacaggga cgagtggggc  1440
gtggacaacg ccatcaaccc cagcgtgctg tggaccctga ccccaggat cgtgagcctg  1500
gacgtggagt acttcggcgt gatgtggccc aacaacgccg ccgtgggcgc cacctacggc  1560
ggcgtgctgg ccgccctggc cgagagcctg gccatccccc ccccgtggc caccatgggc  1620
tacccctacg acgtgcccga ctacgcctga                                  1650

SEQ ID NO: 31          moltype = AA  length = 549
FEATURE                Location/Qualifiers
REGION                 1..549
                       note = Rv3873-Rv1387-Rv3892c fusion protein
source                 1..549
                       mol_type = protein
                       organism = synthetic construct
SEQUENCE: 31
MLWHAMPPEL NTARLMAGAG PAPMLAAAAG WQTLSAALDA QAVELTARLN SLGEAWTGGG    60
SDKALAAATP MVVWLQTAST QAKTRAMQAT AQAAAYTQAM ATTPSLPEIA ANHITQAVLT   120
ATNFFGINTI PIALTEMDYF IRMWNQAALA MEVYQAETAV NTLFEKLEPM ASILDPGASQ   180
MTEPWIAFPP EVHSAMLNYG AGVGPMLISA TQNGELSAQY AEAASEVEEL LGVVASEGWQ   240
GQAAEAFVAA YMPFLAWLIQ ASADCVEMAA QQHVVIEAYT AAVELMPTQV ELAANQIKLA   300
VLVATNFFGI NTIPIAINEA EYVEMWVRAA TTMATYSTVS RSALSAMPHT SPPPLILKSD   360
MPDPGWAART PEANDLLLTA GTGVGTHLAN QTAWTTLGAS HHASGVASAI NTAATAASWL   420
GVGSAASALN VTMLNATLHG LAGWVDVKPA VVSTAIAAFE TANAAMRPAP ECMENRDEWG   480
VDNAINPSVL WTLTPRIVSL DVEYFGVMWP NNAAVGATYG GVLAALAESL AIPPPVATMG   540
YPYDVPDYA                                                          549

SEQ ID NO: 32          moltype = DNA  length = 1650
FEATURE                Location/Qualifiers
misc_feature           1..1650
                       note = Rv1789-Rv1800-Rv1039c fusion protein
source                 1..1650
                       mol_type = other DNA
                       organism = synthetic construct
SEQUENCE: 32
atggacttcg gcgccctgcc ccccgaggtg aacagcgtga ggatgtacgc cggcccccggc    60
agcgcccca tggtggccgc cgccagcgcc tggaacggcc tggccgccga gctgagcagc   120
gccgccaccg gctacgagac cgtgatcacc agctgagca gcgagggctg gctgggcccc   180
gccagcgccg ccatggccga ggccgtggcc ccctacgtgg cctggatgag cgccgccgcc   240
gccaggccg agcaggccgc cacccaggcc agggccgcc cggaggccga cgagggccgcc   300
ttcgccgcca ccgtgccccc ccccctgatc gccgccaaca ggccagcct gatgcagctg   360
atcagccacca acgtgttcgg ccagaacacc agcgccatcg ccgccgccga ggcccagtac   420
ggcgagatgt gggcccagga cagcgccgcc atgtacgcct acgccggcag cagcgccagc   480
gccagcgccg tgaccccctt cagcacccc ccgagatcgc caaccccac cgccaggggc   540
atgctgccca acttcgccgt gctcgccccc gaggtgaaca gccccaggtg gttcgccggc   600
gccggcagcg cccccatgct ggccgccgcc gccgctgggg acgacctggc cagcgagctg   660
cactgcgccg ccatgagctt cggcagcgtg accagcggcc tggtggtgg ctggtggcag   720
ggcagcgcca gcgccgccat ggtggacgcc gccagcctcc acatcggctg gctgagcacc   780
agcgccgccc acgccgaggg cgccgccggc ctggccaggg ccgccgtgag cgtgttcgag   840
gagccctgg ccgccaccgt gcacccgac gcaccaggga ccaggtgccc cgccaccgcc   900
agcctggtgg ccagcaacct gttcggccag aacgcccccg ccatcgccgc cctggagagc   960
ctgtacgagt gcatgtgggc ccaggacgcc gccgccatgg ccggctacta cgtgggcgcc  1020
agcgccgtgg ccacccagct ggccagctgg ctgcagaggc tgcagagcat ccccggcgcc  1080
atggacttcg gcgccctgcc ccccgagatc aacagcgcca ggatgtacgc cggcgccggc  1140
gccgccccca tgatggccgc cggcgccgcc tggaacggcc tggccgccga gctgggcacc  1200
```

```
accgccgcca gctacgagag cgtgatcacc aggctgacca ccgagagctg gatgggcccc  1260
gccagcatgg ccatggtggc cgccgcccag ccctacctgg cctggctgac ctacaccgcc  1320
gaggccgccg cccacgccgg cagccaggcc atgccagcg ccgccgccta cgaggccgcc  1380
tacgccatga ccgtgccccc cgaggtggtg gccgccaaca gggccctgct ggccgccctg  1440
gtggccacca acgtgctggg catcaacacc ccgccatca tggccaccga ggccctgtac  1500
gccgagatgt gggcccagga cgccctggcc atgtacggct acgccgccgc cagcggcgcc  1560
ggcatgc tgcagcccct gagcccccc agccagacca ccaaccccgg cggcctggcc  1620
taccccacg acgtgcccga ctacgcctga                                   1650

SEQ ID NO: 33           moltype = AA   length = 549
FEATURE                 Location/Qualifiers
REGION                  1..549
                        note = Rv1789-Rv1800-Rv1039c fusion protein
source                  1..549
                        mol_type = protein
                        organism = synthetic construct
SEQUENCE: 33
MDFGALPPEV NSVRMYAGPG SAPMVAAASA WNGLAAELSS AATGYETVIT QLSSEGWLGP   60
ASAAMAEAVA PYVAWMSAAA AQAEQAATQA RAAAAAFEAA FAATVPPPLI AANRASLMQL  120
ISTNVFGQNT SAIAAAEAQY GEMWAQDSAA MYAYAGSSAS ASAVTPFSTP PQIANPTAQG  180
MLPNFAVLPP EVNSARVFAG AGSAPMLAAA AAWDDLASEL HCAAMSFGSV TSGLVVGWWQ  240
GSASAAMVDA AASYIGWLST SAAHAEGAAG LARAAVSVFE EALAATVHPA MVAANRAQVA  300
SLVASNLFGQ NAPAIAALES LYECMWAQDA AAMAGYYVGA SAVATQLASW LQRLQSIPGA  360
MDFGALPPEI NSARMYAGAG AGPMMAAGAA WNGLAAELGT TAASYESVIT RLTTESWMGP  420
ASMAMVAAAQ PYLAWLTYTA EAAAHAGSQA MASAAAYEAA YAMTVPPEVV AANRALLAAL  480
VATNVLGINT PAIMATEALY AEMWAQDALA MYGYAAASGA AGMLQPLSPP SQTTNPGGLA  540
YPYDVPDYA                                                         549

SEQ ID NO: 34           moltype = DNA   length = 363
FEATURE                 Location/Qualifiers
misc_feature            1..363
                        note = Rv3017c (esxQ)
source                  1..363
                        mol_type = other DNA
                        organism = synthetic construct
SEQUENCE: 34
gtgagccaga gcatgtacag ctaccccgcc atgaccgcca acgtgggcga catggccggc   60
tacaccggca ccacccagag cctgggcgcc gacatcgcca gcgagaggac cgcccccagc  120
agggcctgcc agggcgacct gggcatgagc caccaggccg gcaccgccca gtggaaccag  180
gccatggagg ccctggccag ggcctacagg aggtgcagga gggccctgag gcagatcggc  240
gtgctggaga ggcccgtggg cgacagcagc gactgcggca ccatcagggt gggcagcttc  300
aggggcaggt ggctggaccc caggcacgcc ggccccgcca ccgccgccga cgccggcgac  360
tga                                                               363

SEQ ID NO: 35           moltype = AA   length = 120
FEATURE                 Location/Qualifiers
REGION                  1..120
                        note = Rv3017c (esxQ)
source                  1..120
                        mol_type = protein
                        organism = synthetic construct
SEQUENCE: 35
VSQSMYSYPA MTANVGDMAG YTGTTQSLGA DIASERTAPS RACQGDLGMS HQDWQAQWNQ   60
AMEALARAYR RCRRALRQIG VLERPVGDSS DCGTIRVGSF RGRWLDPRHA GPATAADAGD  120

SEQ ID NO: 36           moltype = DNA   length = 294
FEATURE                 Location/Qualifiers
misc_feature            1..294
                        note = Rv3020c (esxS)
source                  1..294
                        mol_type = other DNA
                        organism = synthetic construct
SEQUENCE: 36
atgagcctgc tggacgccca catccccag ctgatcgcca gccacaccgc cttcgccgcc    60
aaggccggcc tgatgaggca caccatcggc caggccgagc agcaggccat gagcgcccag  120
gccttccacc agggcgagag cgccgccgcc ttccagggcg cccacgccag gttcgtggcc  180
gccgccgcca aggtgaacac cctgctggac atcgcccagg ccaacctggg cgaggccgcc  240
ggcacctacg tggccgccga cgccgccgcc gccagcagct acaccggctt ctga        294

SEQ ID NO: 37           moltype = AA   length = 97
FEATURE                 Location/Qualifiers
REGION                  1..97
                        note = Rv3020c (esxS)
source                  1..97
                        mol_type = protein
                        organism = synthetic construct
SEQUENCE: 37
MSLLDAHIPQ LIASHTAFAA KAGLMRHTIG QAEQQAMSAQ AFHQGESAAA FQGAHARFVA   60
AAAKVNTLLD IAQANLGEAA GTYVAADAAA ASSYTGF                            97
```

```
SEQ ID NO: 38            moltype = DNA   length = 291
FEATURE                  Location/Qualifiers
misc_feature             1..291
                         note = Rv3019c (esxR)
source                   1..291
                         mol_type = other DNA
                         organism = synthetic construct
SEQUENCE: 38
atgagccaga tcatgtacaa ctaccccgcc atgatggccc acgccggcga catggccggc    60
tacgccggca ccctgcagag cctgggcgcc gacatcgcca gcgagcaggc cgtgctgagc   120
agcgcctggc agggcgacac cggcatcacc taccagggct ggcagaccca gtggaaccag   180
gccctggagg acctggtgag ggcctaccag agcatgagcg gcacccacga gagcaacacc   240
atggccatgc tggccaggga cggcgccgag gccgccaagt ggggcggctg a            291

SEQ ID NO: 39            moltype = AA   length = 96
FEATURE                  Location/Qualifiers
REGION                   1..96
                         note = Rv3019c (esxR)
source                   1..96
                         mol_type = protein
                         organism = synthetic construct
SEQUENCE: 39
MSQIMYNYPA MMAHAGDMAG YAGTLQSLGA DIASEQAVLS SAWQGDTGIT YQGWQTQWNQ    60
ALEDLVRAYQ SMSGTHESNT MAMLARDGAE AAKWGG                              96

SEQ ID NO: 40            moltype = DNA   length = 324
FEATURE                  Location/Qualifiers
misc_feature             1..324
                         note = Rv3891c (esxD)
source                   1..324
                         mol_type = other DNA
                         organism = synthetic construct
SEQUENCE: 40
gtggccgaca ccatccaggt gacccccccag atgctgagga gcaccgccaa cgacatccag   60
gccaacatgg agcaggccat gggcatcgcc aagggctacc tggccaacca ggagaacgtg  120
atgaaccccg ccacctggag cggcaccggc gtggtggcca gccacatgac cgccaccgag  180
atcaccaacg agctgaacaa ggtgctgacc ggcggcacca ggctggccga gggcctggtg  240
caggccgccg ccctgatgga gggccacgag gccgacagcc agaccgcctt ccaggccctg  300
ttcggcgcca gccacggcag ctga                                          324

SEQ ID NO: 41            moltype = AA   length = 107
FEATURE                  Location/Qualifiers
REGION                   1..107
                         note = Rv3891c (esxD)
source                   1..107
                         mol_type = protein
                         organism = synthetic construct
SEQUENCE: 41
VADTIQVTPQ MLRSTANDIQ ANMEQAMGIA KGYLANQENV MNPATWSGTG VVASHMTATE    60
ITNELNKVLT GGTRLAEGLV QAAALMEGHE ADSQTAFQAL FGASHGS                 107

SEQ ID NO: 42            moltype = DNA   length = 285
FEATURE                  Location/Qualifiers
misc_feature             1..285
                         note = Rv2346c (esxO)
source                   1..285
                         mol_type = other DNA
                         organism = synthetic construct
SEQUENCE: 42
atgaccatca actaccagtt cggcgacgtg gacgcccacg gcgccatgat cagggcccag    60
gccggcctgc tggaggccga gcaccaggcc atcgtgaggg acgtgctggc cgccggcgac  120
ttctggggcg gcgccggcag cgtggcctgc caggagttca tcacccagct gggcaggaac  180
ttccaggtga tctacgagca ggccaacgcc cacggccaga ggtgcaggc cgccggcaac   240
aacatggccc agaccgacag cgccgtgggc agcagctggg cctga                  285

SEQ ID NO: 43            moltype = AA   length = 94
FEATURE                  Location/Qualifiers
REGION                   1..94
                         note = Rv2346c (esxO)
source                   1..94
                         mol_type = protein
                         organism = synthetic construct
SEQUENCE: 43
MTINYQFGDV DAHGAMIRAQ AGLLEAEHQA IVRDVLAAGD FWGGAGSVAC QEFITQLGRN    60
FQVIYEQANA HGQKVQAAGN NMAQTDSAVG SSWA                                94

SEQ ID NO: 44            moltype = DNA   length = 318
FEATURE                  Location/Qualifiers
```

```
misc_feature              1..318
                          note = Rv3445c (esxU)
source                    1..318
                          mol_type = other DNA
                          organism = synthetic construct
SEQUENCE: 44
gtgagcaccc ccaacaccct gaacgccgac ttcgacctga tgaggagcgt ggccggcatc    60
accgacgcca ggaacgagga gatcagggcc atgctgcagg ccttcatcgg caggatgagc   120
ggcgtgcccc ccagcgtgtg gggcggcctg ccgccgccca ggttccagga cgtggtggac   180
aggtggaacg ccgagagcac caggctgtac cacgtgctgc acgccatcgc cgacaccatc   240
aggcacaacg aggccgccct gagggaggcc ggccagatcc acgccaggca catcgccgcc   300
gccggcggcg acctgtga                                                 318

SEQ ID NO: 45             moltype = AA  length = 105
FEATURE                   Location/Qualifiers
REGION                    1..105
                          note = Rv3445c (esxU)
source                    1..105
                          mol_type = protein
                          organism = synthetic construct
SEQUENCE: 45
VSTPNTLNAD FDLMRSVAGI TDARNEEIRA MLQAFIGRMS GVPPSVWGGL AAARFQDVVD    60
RWNAESTRLY HVLHAIADTI RHNEAALREA GQIHARHIAA AGGDL                   105

SEQ ID NO: 46             moltype = DNA  length = 285
FEATURE                   Location/Qualifiers
misc_feature              1..285
                          note = Rv3619c (esxV)
source                    1..285
                          mol_type = other DNA
                          organism = synthetic construct
SEQUENCE: 46
atgaccatca actaccagtt cggcgacgtg gacgcccacg gcgccatgat cagggcccag    60
gccggcagcc tggaggccga gcaccaggca atcatcagcg acgtgctgac cgccagcgac   120
ttctggggcg gcgccggcag cgccgcctgc caggggttca tcacccagct gggccaggaa   180
ttccaggtga tctacgagca ggccaacgcc cacggccaga aggtgcaggc cgccgcaggc   240
aacatggccc agaccgacag cgccgtgggc agcagctggg cctga                   285

SEQ ID NO: 47             moltype = AA  length = 94
FEATURE                   Location/Qualifiers
REGION                    1..94
                          note = Rv3619c (esxV)
source                    1..94
                          mol_type = protein
                          organism = synthetic construct
SEQUENCE: 47
MTINYQFGDV DAHGAMIRAQ AGSLEAEHQA IISDVLTASD FWGGAGSAAC QGFITQLGRN    60
FQVIYEQANA HGQKVQAAGN NMAQTDSAVG SSWA                                94

SEQ ID NO: 48             moltype = DNA  length = 288
FEATURE                   Location/Qualifiers
misc_feature              1..288
                          note = Rv3875 (esxA, ESAT6)
source                    1..288
                          mol_type = other DNA
                          organism = synthetic construct
SEQUENCE: 48
atgaccgagc agcagtggaa cttcgccggc atcgaggccg ccgccagcgc catccagggc    60
aacgtgacca gcatccacag cctgctggac gagggcaagc agagcctgac caagctggcc   120
gccgctgggg gcggcagcgg cagcgaggcc taccagggcg tgcagcagaa gtgggacgcc   180
accgccaccg agctgaacaa cgccctgcag aacctggcca ggaccatcag cgaggccggc   240
caggccatgg ccagcaccga gggcaacgtg accggcatgt tcgcctga                288

SEQ ID NO: 49             moltype = AA  length = 95
FEATURE                   Location/Qualifiers
REGION                    1..95
                          note = Rv3875 (esxA, ESAT6)
source                    1..95
                          mol_type = protein
                          organism = synthetic construct
SEQUENCE: 49
MTEQQWNFAG IEAAASAIQG NVTSIHSLLD EGKQSLTKLA AAWGGSGSEA YQGVQQKWDA    60
TATELNNALQ NLARTISEAG QAMASTEGNV TGMFA                               95

SEQ ID NO: 50             moltype = DNA  length = 303
FEATURE                   Location/Qualifiers
misc_feature              1..303
                          note = Rv3874 (esxB, CFP10)
source                    1..303
```

```
                        mol_type = other DNA
                        organism = synthetic construct
SEQUENCE: 50
atggccgaga tgaagaccga cgccgccacc ctggcccagg aggccggcaa cttcgagagg    60
atcagcggcg acctgaagac ccagatcgac caggtggaga gcaccgccgg cagcctgcag   120
ggccagtgga ggggcgccgc cggcaccgcc gcccaggccg ccgtggtgag gttccaggag   180
gccgccaaca gcagaagca ggagctggac gagatcagca ccaacatcag gcaggccggc   240
gtgcagtaca gcagggccga cgaggagcag cagcaggccc tgagcagcca gatgggcttc   300
tga                                                                 303

SEQ ID NO: 51           moltype = AA   length = 100
FEATURE                 Location/Qualifiers
REGION                  1..100
                        note = Rv3874 (esxB, CFP10)
source                  1..100
                        mol_type = protein
                        organism = synthetic construct
SEQUENCE: 51
MAEMKTDAAT LAQEAGNFER ISGDLKTQID QVESTAGSLQ GQWRGAAGTA AQAAVVRFQE    60
AANKQKQELD EISTNIRQAG VQYSRADEEQ QQALSSQMGF                         100

SEQ ID NO: 52           moltype = DNA   length = 1887
FEATURE                 Location/Qualifiers
misc_feature            1..1887
                        note = Rv3017c-Rv3020c-Rv3019c-Rv3891c-Rv2346c-Rv3445c
                        fusion protein
source                  1..1887
                        mol_type = other DNA
                        organism = synthetic construct
SEQUENCE: 52
gtgagccaga gcatgtacag ctaccccgcc atgaccgcca acgtgggcga catggccggc    60
tacaccggca ccacccagag cctgggcgcc gacatcgcca gcgagaggac cgccccccagc  120
agggcctgcc agggcgacct gggcatgagc accaggact gcaggccca gtggaaccag    180
gccatggagg ccctggccag ggcctacagg aggtgcagga gggccctgag gcagatcggc   240
gtgctggaga ggcccgtggg cgacagcagc gactgcggca ccatcagggt gggcagcttc   300
agggcaggt ggctggaccc caggcacgcc ggccccgcca ccgccgccga cgccggcgac    360
atgagcctgc tggacgccca catccccag ctgatcgcca gccacccgc cttcgccgcc    420
aaggccggct gatgaggca ccatccggc caggccgagc agcaggccat gagcgcccag    480
gccttccacc agggcgagag cgccgccgcc ttccagggcg ccacgccga gttcgtggcc    540
gccgccgcca aggtgaacac cctgctggac atccccagg ccaacctggg cgaggccgcc   600
ggcacctacg tggccgccga cgccgccgcc gccagcagct acaccggctt catgagccag   660
atcatgtaca actaccccgc catgatggcc cacgccggcg acatggccgg ctacgccggc   720
accctgcaga gcctgggcgc cgacatcgcc agcgagcagg ccgtgctgag cagcgcctgg   780
cagggcgaca ccggcatcac ctaccagggc tggcagaccc agtggaacca ggccctggag   840
gacctggtga ggcctaccac gagcatgagc ggcacccacg agagcaacac catggccatg   900
ctggccaggg acggcgccga ggccgccaag tggggcggcg tggccgacac catccaggtg   960
acccccagaa tgctgaggag caccgccaac gatatccagg ccaacatgga gcaggccatg  1020
ggcatcgcca agggctacct ggccaaccag gagaacgtga tgaacccgc cacctggagc   1080
ggcaccggcg tggtggccag ccacatgacc gccaccgaga tcaccaacga gctgaacaag  1140
gtgctgaccg gcggcaccag gctggccgag ggcctggtgc aggccgccgc cctgatggag  1200
ggccacgagg ccgacagcca gaccgccttc caggccctgt tcggcgccag ccacggcagc  1260
atgaccatca actaccagtt cggcgacgtg gacgcccacg cgccatgat cagggcccag   1320
gccgccctgc tggaggccga gcaccaggcc atcgtgaggg acgtgctggc cgccggcgac  1380
ttctgggcgg cgccggcag cgtggcctgc aggagttca tcccagct gggcaggaac     1440
ttccaggtga tctacgagca ggccaacgcc cacggccaga aggtgcaggc cgccggcaac   1500
aacatggccc agaccgacag cgccgtgggc agcagctggg ccgtgagcac cccaacacc    1560
ctgaacgccg acttcgacct gatgaggagc gtggccggca tcaccgacgc caggaacgag  1620
gagatcaggg ccatgctgca ggccttcatc ggcaggatga gcggcgtgcc ccccagcgtg  1680
tggggcggcc tggccgccgc caggttccag gacctggtgg acaggtggaa cgccgagagc  1740
accaggctgt accacgtgct gcacgccatc ccgacacca tcaggcacaa cgaggccgcc   1800
ctgagggagg ccggccagat ccacgccagg cacatccgg cgccggcgg cgacctgtac    1860
ccctacgacg tgcccgacta cgcctga                                      1887

SEQ ID NO: 53           moltype = AA   length = 628
FEATURE                 Location/Qualifiers
REGION                  1..628
                        note = Rv3017c-Rv3020c-Rv3019c-Rv3891c-Rv2346c-Rv3445c
                        fusion protein
source                  1..628
                        mol_type = protein
                        organism = synthetic construct
SEQUENCE: 53
VSQSMYSYPA MTANVGDMAG YTGTTQSLGA DIASERTAPS RACQGDLGMS HQDWQAQWNQ    60
AMEALARAYR RCRRALRQIG VLERPVGDSS DCGTIRVGSF RGRWLDPRHA GPATAADAGD   120
MSLLDAHIPQ LIASHTAFAA KAGLMRHTIG QAEQQAMSAQ AFHQGESAAA FQGAHARFVA   180
AAAKVNTLLD IAQANLGEAA GTYVAADAAA ASSYTGFMSQ IMYNYPAMMA HAGDMAGYAG   240
TLQSLGADIA SEQAVLSSAW QGDTGITYQG WQTQWNQALE DLVRAYQSMS GTHESNTMAM   300
LARDGAEEAK WGGVADTIQV TPQMLRSTAN DIQANMEQAM GIAKGYLANQ ENVMNPATWS   360
GTGVVASHMT ATEITNELNK VLTGGTRLAE GLVQAAALME GHEADSQTAF QALFGASHGS   420
```

```
MTINYQFGDV DAHGAMIRAQ AGLLEAEHQA IVRDVLAAGD FWGGAGSVAC QEFITQLGRN    480
FQVIYEQANA HGQKVQAAGN NMAQTDSAVG SSWAVSTPNT LNADFDLMRS VAGITDARNE    540
EIRAMLQAFI GRMSGVPPSV WGGLAAARFQ DVVDRWNAES TRLYHVLHAI ADTIRHNEAA    600
LREAGQIHAR HIAAAGGDLY PYDVPDYA                                      628

SEQ ID NO: 54          moltype = DNA   length = 897
FEATURE                Location/Qualifiers
misc_feature           1..897
                       note = Rv3619c-Rv3875-Rv3874 fusion protein
source                 1..897
                       mol_type = other DNA
                       organism = synthetic construct
SEQUENCE: 54
atgaccatca actaccagtt cggcgacgtg gacgcccacg gcgccatgat cagggcccag     60
gccggcagcc tggaggccga gcaccaggcc atcatcagcg acgtgctgac cgccagcgac    120
ttctggggcg gcgccggcag cgccgcctgc cagggcttca tcacccagct gggcaggaac    180
ttccaggtga tctacgagca ggccaacgcc acgggcagga aggtgcaggc cgccggcaac    240
aacatggccc agaccgacag cgccgtgggc agcagctggg ccatgaccga gcagcagtgg    300
aacttcgccg gcatcgaggc cgccgccagc gccatccagg gcaacgtgac cagcatccac    360
agcctgctgg acgagggcaa gcagagcctg accaagctgg ccgccgcctg gggcggcagc    420
ggcagcgagg cctaccaggg cgtgcagcag aagtgggacg ccaccgccac cgagctgaac    480
aacgccctgc agaacctggc caggaccatc agcgaggccg gccaggccat ggccagcacc    540
gagggcaacg tgaccggcat gttcgccatg gccgagatga agaccgacgc cgccaccctg    600
gcccaggagg ccggcaactt cgagaggatc agcggcgacc tgaagaccca gatcgaccag    660
gtggagagca ccgccggcag cctgcagggc agtggagggg cgccgccgg caccgccgcc    720
caggccgccg tggtgaggtt ccaggaggcc gccaacagga gaagcaggaa gctggacgag    780
atcagcacca acatcaggca ggccggcgtg cagtacagca gggccgacga ggagcagcag    840
caggccctga gcagccagat gggcttctac ccctacgacg tgcccgacta cgcctga       897

SEQ ID NO: 55          moltype = AA   length = 298
FEATURE                Location/Qualifiers
REGION                 1..298
                       note = Rv3619c-Rv3875-Rv3874 fusion protein
source                 1..298
                       mol_type = protein
                       organism = synthetic construct
SEQUENCE: 55
MTINYQFGDV DAHGAMIRAQ AGSLEAEHQA IISDVLTASD FWGGAGSAAC QGFITQLGRN     60
FQVIYEQANA HGQKVQAAGN NMAQTDSAVG SSWAMTEQQW NFAGIEAAAS AIQGNVTSIH    120
SLLDEGKQSL TKLAAAWGGS GSEAYQGVQQ KWDATATELN NALQNLARTI SEAGQAMAST    180
EGNVTGMFAM AEMKTDAATL AQEAGNFERI SGDLKTQIDQ VESTAGSLQG QWRGAAGTAA    240
QAAVVRFQEA ANKQKQELDE ISTNIRQAGV QYSRADEEQQ QALSSQMGFY PYDVPDYA      298

SEQ ID NO: 56          moltype = DNA   length = 498
FEATURE                Location/Qualifiers
misc_feature           1..498
                       note = Rv2719c
source                 1..498
                       mol_type = other DNA
                       organism = synthetic construct
SEQUENCE: 56
atgacccccg tgaggccccc ccacaccccc gaccccctga acctgagggg ccccctggac     60
ggccccaggt ggaggagggc cgagcccgcc cagagcagga gcccggcag gagcaggccc    120
ggcggcgccc ccctgaggta ccacaggacc ggcgtgggca tgagcaggac cggccacggc    180
agccgccccg tgcccccccg caccaccgtg ggcctggccc tgctggccgc cgccatcacc    240
ctgtggctgg gcctggtggc ccagttccgg cagatgatca ccggcggcag cgccgacggc    300
agcgccgaca gcaccggcag ggtgcccgac aggctggccg tggtgagggt ggagaccggc    360
gagagcctgt acgacgtggc cgtgagggtg gccccaacg ccccccacag gcaggtggcc    420
gacaggatca gggagctgaa cggcctgcag acccccgccc tggccgtggg ccagaccctg    480
atcgcccccg tgggctga                                                 498

SEQ ID NO: 57          moltype = AA   length = 165
FEATURE                Location/Qualifiers
REGION                 1..165
                       note = Rv2719c
source                 1..165
                       mol_type = protein
                       organism = synthetic construct
SEQUENCE: 57
MTPVRPPHTP DPLNLRGPLD GPRWRRAEPA QSRRPGRSRP GGAPLRYHRT GVGMSRTGHG     60
SRPVPPATTV GLALLAAAIT LWLGLVAQFG QMITGGSADG SADSTGRVPD RLAVVRVETG    120
ESLYDVAVRV APNAPTRQVA DRIRELNGLQ TPALAVGQTL IAPVG                    165

SEQ ID NO: 58          moltype = DNA   length = 426
FEATURE                Location/Qualifiers
misc_feature           1..426
                       note = Rv0010c
source                 1..426
                       mol_type = other DNA
```

```
                         organism = synthetic construct
SEQUENCE: 58
atgcagcaga ccgcctgggc ccccaggacc agcggcatcg ccggctgcgg cgccggcggc    60
gtggtgatgg ccatcgccag cgtgaccctg gtgaccgaca cccccggcag ggtgctgacc   120
ggcgtggccg ccctgggcct gatcctgttc gccagcgcca cctggagggc caggcccagg   180
ctggccatca cccccgacgg cctggccatc aggggctggt tcaggaccca gctgctgagg   240
cacagcaaca tcaagatcat caggatcgac gagttcagga ggtacggcag gctggtgagg   300
ctgctggaga tcgagaccgt gagcggcggc ctgctgatcc tgagcaggtg ggacctgggc   360
accgaccccg tggaggtgct ggacgccctg accgccgccg gctacgccgg cagggggcag   420
aggtga                                                              426

SEQ ID NO: 59            moltype = AA  length = 141
FEATURE                  Location/Qualifiers
REGION                   1..141
                         note = Rv0010c
source                   1..141
                         mol_type = protein
                         organism = synthetic construct
SEQUENCE: 59
MQQTAWAPRT SGIAGCGAGG VVMAIASVTL VTDTPGRVLT GVAALGLILF ASATWRARPR    60
LAITPDGLAI RGWFRTQLLR HSNIKIIRID EFRRYGRLVR LLEIETVSGG LLILSRWDLG   120
TDPVEVLDAL TAAGYAGRGQ R                                             141

SEQ ID NO: 60            moltype = DNA  length = 1245
FEATURE                  Location/Qualifiers
misc_feature             1..1245
                         note = Rv1872c
source                   1..1245
                         mol_type = other DNA
                         organism = synthetic construct
SEQUENCE: 60
atggccgtga acaggagggt gcccagggtg agggacctgg cccccctgct gcagttcaac    60
aggcccagt cgacaccag caagaggagg ctgggcgccg ccctgaccat ccaggacctg    120
aggaggatcg ccaagaggag gaccccccagg gccgccttcg actacgccga cggcggcgcc   180
gaggacgagc tgagcatcgc caggggccagg cagggccttca gggaaccatcga gttccacccg   240
accatcctga gggacgtgac caccgtgtgc gccggctgga acgtgctggg ccagcccacc   300
gtgctgccct tcggcatcgc ccccaccggc ttcaccaggc tgatgcacac cgagggcgag   360
atcgccggcc caggggccgc cgccgccgcc ggcatcccct tcagcctgag cacccttggcc   420
acctgcgcca tcgaggacct ggtgatcgcc gtgccccagg gcaggaagtg gttccagctg   480
tacatgtgga gggacaggga caggagcatg gccctggtga ggagggtggc cgccgccggc   540
ttcgacacca tgctggtgac cgtggacgtg cccgtggccg cgccaggct gagggacgtg   600
aggaacggca tgagcatccc ccccgccctg accctgagga ccgtgctgga cgccatgggc   660
caccccaggt ggtggttcga cctgctgacc accgagccct ggccctttcgc cagcctgggac   720
aggtggcccg gcaccgtggg cgagtacctg aacaccgtgt tcgacccccag cctgaccttc   780
gacgacctgg cctggatcaa gagccagtgg cccggcaagc tggtggtgaa gggcatccag   840
accctggacg acgccagggc cgtggtggac aggggcgtgg acggcatcgt gctgagcaac   900
cacggccggca ggcagctgga caggggccccc gtgcccttcc acctgcctgcc ccacgtggcc   960
aggggagctgg gcaagcacac cgagatcctg gtggacaccg gcatcatgag cggcgccgac  1020
atcgtggccg ccatcgccct gggcgccagg tgcaccctga tcggcagggc ctacctgtac  1080
ggcctgatgg ccggcgcga ggccggcgtg aacaggccca tcgagatcct gcagaccggc  1140
gtgatcagga ccatgaggct gctgggcgtg acctgcctgg aggagctgag ccccaggcac  1200
gtgacccagc tgaggaggct gggccccatc ggcgccccca cctga                   1245

SEQ ID NO: 61            moltype = AA  length = 414
FEATURE                  Location/Qualifiers
REGION                   1..414
                         note = Rv1872c
source                   1..414
                         mol_type = protein
                         organism = synthetic construct
SEQUENCE: 61
MAVNRRVPRV RDLAPLLQFN RPQFDTSKRR LGAALTIQDL RRIAKRRTPR AAFDYADGGA    60
EDELSIARAR QGFRDIEFHP TILRDVTTVC AGWNVLGQPT VLPFGIAPTG FTRLMHTEGE   120
IAGARAAAAA GIPFSLSTLA TCAIEDLVIA VPQGRKWFQL YMWRDRDRSM ALVRRVAAAG   180
FDTMLVTVDV PVAGARLRDV RNGMSIPPAL TLRTVLDAMG HPRWWFDLLT TEPLAFASLD   240
RWPGTVGEYL NTVFDPSLTF DDLAWIKSQW PGKLVVKGIQ TLDDARAVVD RGVDGIVLSN   300
HGGRQLDRAP VPFHLLPHVA RELGKHTEIL VDTGIMSGAD IVAAIALGAR CTLIGRAYLY   360
GLMAGGEAGV NRAIEILQTG VIRTMRLLGV TCLEELSPRH VTQLRRLGPI GAPT          414

SEQ ID NO: 62            moltype = DNA  length = 789
FEATURE                  Location/Qualifiers
misc_feature             1..789
                         note = Rv0012
source                   1..789
                         mol_type = other DNA
                         organism = synthetic construct
SEQUENCE: 62
atgaggctga cccaccccac ccctgcccc gagaacggcg agaccatgat cgacaggagg    60
aggagcgcct ggaggttcag cgtgcccctg gtgtgcctgc tggccggcct gctgctggcc   120
```

```
gccacccacg gcgtgagcgg cggcaccgag atcaggagga gcgacgcccc caggctggtg    180
gacctggtga ggagggccca ggccagcgtg aacaggctgg ccaccgagag ggaggccctg    240
accaccagga tcgacagcgt gcacggcagg agcgtggaca ccgccctggc cgccatgcag    300
aggaggagcg ccaagctggc cggcgtggcc gccatgaacc ccgtgcacgg ccccggcctg    360
gtggtgaccc tgcaggacgc ccagagggac gccaacggcc ggttccccag ggacgccagc    420
cccgacgacc tggtggtgca ccagcaggac atcgaggccg tgctgaacgc cctgtggaac    480
gccggcgccg aggccatcca gatgcaggac cagaggatca tcgccatgag catcgccagg    540
tgcgtgggca cacccctgct gctgaacggc aggacctaca gccccccta caccatcgcc    600
gccatcggcg acgccgccgc catgcaggcc gccctggccg ccgcccccct ggtgaccctg    660
tacaagcagt acgtggtgag gttcggcctg ggctacttcg aggaggtgca ccccgacctg    720
cagatcgtgg gctacgccga ccccgtgagg atgcacttcg cccagcccgc cggccccctg    780
gactactga                                                            789

SEQ ID NO: 63           moltype = AA   length = 262
FEATURE                 Location/Qualifiers
REGION                  1..262
                        note = Rv0012
source                  1..262
                        mol_type = protein
                        organism = synthetic construct
SEQUENCE: 63
MRLTHPTPCP ENGETMIDRR RSAWRFSVPL VCLLAGLLLA ATHGVSGGTE IRRSDAPRLV     60
DLVRRAQASV NRLATEREAL TTRIDSVHGR SVDTALAAMQ RRSAKLAGVA AMNPVHGPGL    120
VVTLQDAQRD ANGRFPRDAS PDDLVVHQQD IEAVLNALWN AGAEAIQMQD QRIIAMSIAR    180
CVGNTLLLNG RTYSPPYTIA AIGDAAAMQA ALAAAPLVTL YKQYVVRFGL GYCEEVHPDL    240
QIVGYADPVR MHFAQPAGPL DY                                             262

SEQ ID NO: 64           moltype = DNA   length = 657
FEATURE                 Location/Qualifiers
misc_feature            1..657
                        note = Rv0990c
source                  1..657
                        mol_type = other DNA
                        organism = synthetic construct
SEQUENCE: 64
gtggccgaga gcagcctgaa ccccagcctg gtgagcagga tcagcgcctt cctgaggccc     60
gactggacca ggaccgtgag ggccaggagg ttcgccgccg ccggcctggt gatgctggcc    120
ggcgtggccg ccctgaggag caaccccgag gacgacagga gcgaggtggt ggtggccgcc    180
cacgacctga ggcccggcac cgcccctgacc cccggcgacg tgaggctgga gaagaggagc    240
gccaccaccc tgcccgacgg cagccaggcc gacctggacg ccgtggtggg cagcaccctg    300
gccagcccca ccaggagggg cgaggtgctc accgacgtga ggctgctggg cagcaggctg    360
gccgagagca ccgccggccc cgacgccagg atcgtgcccc tgcacctggc cgacagcgcc    420
ctggtggacc tggtgagggt ggggcgacgtg gtggacgtgc tggccccgtgaccgac        480
agccccgccg ccctgaggct gctggccacc gacgccatcg tggtgctggt gagcgcccag    540
cagaaggccc aggccgccga cagcgacagg gtggtgctgg tggccctgcc cgccaggctg    600
gccaacaccg tggccggcgc cgccctgggc cagaccgtga ccctgaccct gcactga       657

SEQ ID NO: 65           moltype = AA   length = 218
FEATURE                 Location/Qualifiers
REGION                  1..218
                        note = Rv0990c
source                  1..218
                        mol_type = protein
                        organism = synthetic construct
SEQUENCE: 65
VAESSLNPSL VSRISAFLRP DWTRTVRARR FAAAGLVMLA GVAALRSNPE DDRSEVVVAA     60
HDLRPGTALT PGDVRLEKRS ATTLPDGSQA DLDAVVGSTL ASPTRRGEVL TDVRLLGSRL    120
AESTAGPDAR IVPLHLADSA LVDLVRVGDV VDVLAAPVTD SPAALRLLAT DAIVVLVSAQ    180
QKAQAADSDR VVLVALPARL ANTVAGAALG QTVTLTLH                            218

SEQ ID NO: 66           moltype = DNA   length = 612
FEATURE                 Location/Qualifiers
misc_feature            1..612
                        note = Rv0995
source                  1..612
                        mol_type = other DNA
                        organism = synthetic construct
SEQUENCE: 66
atggccgtgg gccccctgag ggtgagcgcc ggcgtgatca ggctgaggcc cgtgaggatg     60
agggacggcg tgcactggag caggatcagg ctggccgaca gggcccacct ggagccctgg    120
gagcccagcg ccgacggcga gtggaccgtg aggcacaccg tggccgcctg gccgccgtg    180
tgcagcggcc tgaggagcga ggccaggaac ggcaggatgc tgccctacgt gatcgagctg    240
gacgccagt tctgcggcca gctgaccatc ggcaacgtga cccacggcgc cctgaggagc    300
gcctggatcg gctactgggt gcccagcgcc ggcaaccggc caccggaggc                360
ctggccctgg gcctgaccca ctgcttcggc cccgtgatgc tgcacagggt ggaggccacc    420
gtgaggcccg agaacgccgc cagcagggcc gtgctggcca agtggggctt cagggaggag    480
ggcctgctga ggaggtacct ggaggtggac agggcctgga ggaccacct gctgatggcc    540
atcaccgtgg aggaggtgta cggcagcgtg gccagcaccc tggtgagggc cggccacgcc    600
agctggcccc ga                                                        612
```

```
SEQ ID NO: 67              moltype = AA  length = 203
FEATURE                    Location/Qualifiers
REGION                     1..203
                           note = Rv0995
source                     1..203
                           mol_type = protein
                           organism = synthetic construct
SEQUENCE: 67
MAVGPLRVSA GVIRLRPVRM RDGVHWSRIR LADRAHLEPW EPSADGEWTV RHTVAAWPAV   60
CSGLRSEARN GRMLPYVIEL DGQFCGQLTI GNVTHGALRS AWIGYWVPSA ATGGVATGA   120
LALGLDHCFG PVMLHRVEAT VRPENAASRA VLAKVGFREE GLLRRYLEVD RAWRDHLLMA 180
ITVEEVYGSV ASTLVRAGHA SWP                                         203

SEQ ID NO: 68              moltype = DNA  length = 2190
FEATURE                    Location/Qualifiers
misc_feature               1..2190
                           note = Rv2719c-Rv0010c-Rv1872c fusion protein
source                     1..2190
                           mol_type = other DNA
                           organism = synthetic construct
SEQUENCE: 68
atgaccccg tgaggccccc ccacacccc gaccccctga acctgagggg ccccctggac    60
ggccccaggt ggaggagggc cgagcccgcc cagagcagga ggcccggcag gagcaggccc  120
ggcggcgccc cctgaggta ccacaggacc ggcgtgggca tgagcaggac cggccacggg  180
agcaggcccg tgccccccgc caccaccgtg ggcctgcccg tgctgccgcc cgccatcacc  240
ctgtggctgg gcctggtggc ccagttcggc cagatgatca ccggcggcag cgccgacggc  300
agcgccgaca gcaccggcag ggtgcccgac aggctggccg tggtgagggt ggagaccggc  360
gagagcctgt acgacgtggc cgtgagggtg ccccccaacg cccccaccag gcaggtggcc  420
gacaggatca gggagctgaa cggcctgcag acccccggtc tggccgtgg ccagaccctg   480
atcgcccccg tgggcatgca gcagaccgcc tgggccccca ggaccagcgg catcgccggc  540
tgcggcgccg gcgcgtggt gatggccatc gccagcgtga ccctggtgac cgacaccccc  600
ggcagggtgc tgaccggcgt ggccgccctg ggcctgatcc tgttcgccag cgccacctgg  660
agggccaggc ccaggctggc catcaccccc gacggctgcc catcaggggc tggttcaggc  720
acccagctgc tgaggcacag caacatcaag atcatcagga tcgacgagtt caggaggtac  780
ggcaggctgg tgaggctgct ggagatcgag accgtgagcg gcggcctgct gatcctgagc  840
aggtgggacc tggcaccgac cccgtgagg tgctgacg cccgtgagc gccgctggctac    900
gccggcaggg ccagaggat ggccgtgaac aggagggtgc ccagggtgag ggacctggcc   960
cccctgctgc agttcaacag gcccccagttc gacaccagca agaggaggt gggcgccgcc 1020
ctgaccatcc aggacctgag gaggatcgcc aagaggagga cccccagggc cgcctcgac  1080
tacgccgacg gcgccgccga ggacgagctg agcatcgcca gggccaggca ggcttcagg  1140
gacatcgagt tccacccac catcctgagg gacgtgacca ccgtgtgcgc cggctggaac  1200
gtgctgggcc agcccaccgt gctgccttc ggcatccca ccaccggctt caccaggctg  1260
atgcacaccg agggcgagat cgccggcgcc agggccgcc ccgccgccgg catccccttc  1320
agcctgagca ccctgccac ctgcgccatc gaggacctgg tgatcgcgt gccccagggc  1380
aggaagtggt tccagctgta catgtggagg gacagggaca ggagcatggc cctggtgagg  1440
agggtgccg ccgccggctt cgacaccatg ctggtgaccg tggacgtgcc cgtggccggc   1500
gccaggctga gggacgtgag gaacggcatg agcatccccc cgccctgac cctgaggacc  1560
gtgctgacg ccatgggcca ccccaggtgg ttcgacc tgctgaccac cgagcccctg     1620
gccttcgcca gcctggacag gtggcccggc accgtgggcg agtacctgaa caccgtgttc  1680
gacccccagc tgaccttcga cgacctggcc tggatcaaga gccagtggcc cggcaagctg  1740
gtggtgaagg gcatccagac cctggacgac gccaggcccg tggtggacag gggcgtggac  1800
ggcatcgtgc tgagcaacca cggcggcagg cagctggaca gggcccccgt gcccttccac  1860
ctgctgcccc acgtggccag ggagctgggc aagcacaccg atcctggt ggacaccggc    1920
atcatgagcg gcgccgacat cgtggccgcc atcgccctgg gcgccaggtg cacccctgatc  1980
ggcagggcct acctgtacgg cctgatggcc ggcggcgagg ccggcgtgaa cagggccatc  2040
gagatcctgc agaccggcgt gatcaggacc atgaggctgc tgggcgtgac ctgcctggag  2100
gagctgagcc ccaggcacgt gacccagctg aggaggctgg ccccatcgg cgcccccacc  2160
taccctacg acgtgcccga ctacgcctga                                   2190

SEQ ID NO: 69              moltype = AA  length = 729
FEATURE                    Location/Qualifiers
REGION                     1..729
                           note = Rv2719c-Rv0010c-Rv1872c fusion protein
source                     1..729
                           mol_type = protein
                           organism = synthetic construct
SEQUENCE: 69
MTPVRPPHTP DPLNLRGPLD GPRWRRAEPA QSRRPGRSRP GGAPLRYHRT GVGMSRTGHG   60
SRPVPPATTV GLALLAAAIT LWLGLVAQFG QMITGGSADG SADSTGRVPD RLAVVRVETG  120
ESLYDVAVRV APNAPTRQVA DRIRELNGLQ TPALAVGQTL IAPVGMQQTA WAPRTSGIAG  180
CGAGGVVMAI ASVTLVTDTP GRVLTGVAAL GLILFASATW RARPRLAITP DGLAIRGWFR  240
TQLLRHSNIK IIRIDEFRRY GRLVRLLEIE TVSGGLLILS RWDLGTDPVE VLDALTAAGY  300
AGRGQRMAVN RRVPRVRDLA PLLQFNRPQF DTSKRRLGAA LTIQDLRRIA KRRTPRAAFD  360
YADGGAEDEL SIARARQGFR DIEFHPTILR DVTTVCAGWN VLGQPTVLPF GIAPTGFTRL  420
MHTEGEIAGA RAAAAGIPF SLSTLATCAI EDLVIAPQG RKWFQLYMWR DRDRSMALVR    480
RVAAAGFDTM LVTVDVPVAG ARLRDVRNGM SIPPALTLRT VLDAMGHPRW WFDLLTTEPL  540
AFASLDRWPG TVGEYLNTVF DPSLTFDDLA WIKSQWPGKL VVKGIQTLDD ARAVVDRGVD  600
GIVLSNHGGR QLDRAPVPFH LLPHVARELG KHTEILVDTG IMSGADIVAA IALGARCTLI  660
```

```
GRAYLYGLMA GGEAGVNRAI EILQTGVIRT MRLLGVTCLE ELSPRHVTQL RRLGPIGAPT    720
YPYDVPDYA                                                           729

SEQ ID NO: 70           moltype = DNA  length = 2079
FEATURE                 Location/Qualifiers
misc_feature            1..2079
                        note = Rv0012-Rv0990c-Rv0995 fusion protein
source                  1..2079
                        mol_type = other DNA
                        organism = synthetic construct
SEQUENCE: 70
atgaggctga cccaccccac cccctgcccc gagaacggcg agaccatgat cgacaggagg    60
aggagcgcct ggaggttcag cgtgcccctg tgtgcctgc tggccggcct gctgctggcc    120
gccacccacg gcgtgagcgg cggcaccgag atcaggagga gcgacgcccc caggctggtg    180
gacctggtga ggagggccca ggccagcgtg aacaggctgg ccaccgagag ggaggccctg    240
accaccagga tcgacagcgt gcacggcagg agcgtggaca ccgccctggc cgccatgcag    300
aggaggagcg ccaagctggc cggcgtggcc gccatgaacc ccgtgcacgg ccccggcctg    360
gtggtgaccc tgcaggacgc ccagagggac gccaacggca ggttccccag ggacgccagc    420
cccgacgacc tggtggtgca ccagcaggac atcgaggccg tgctgaacgc cctgtggaac    480
gccggcgccg aggccatcca gatgcaggac cagaggatca tcgccatgag catcgccagg    540
tgcgtgggca cacccctgct gctgaacggc aggacctaca gccccccta ccatcatcgcc    600
gccatcggcg acgccgccgc catgcaggcc gccctggccg ccgcccccct ggtgaccctg    660
tacaagcagt acgtggtgag gttcggcctg ggctactgcg aggaggtgca ccccgacctg    720
cagatcgtgg gctacgccga ccccgtgagg atgcacttcg cccagcccgc cggccccctg    780
gactacgtgg ccgagagcag cctgaacccc agcctggtga caggatcag cgccttcctg    840
aggcccgact ggaccaggac cgtgagggcc aggaggttcg ccgccggcct cctggtgatg    900
ctggccggcg tggccgccct gaggagcaac cccgaggacg acaggagcga ggtggtggtg    960
gccgccacg acctgaggcc cggcaccgcc ctgacccccg cgacgtgag gctggagaag    1020
aggagcgcca ccaccctgcc cgacggcagc caggccgacc tggacgccgt ggtgggcagc    1080
accctggcca gccccaccag gaggggcgag gtgctgaccg acgtgaggct gctgggcagc    1140
aggctggccg agagcaccgc cggccccgac gccaggatcg tgcccctgca cctggccgac    1200
agcgccctgg tggacctggt gagggtgggc gacgtggtgg acgtgctggc cgcccccgtg    1260
accgacagcc ccgccgccct gaggctgctg gccaccgacg ccatcgtggt gctggtgagc    1320
gcccagcaga aggcccaggc cgccgacagc gacagggtgg tgctggtggc cctgcccgcc    1380
aggctggcca acaccgtggc cggcgccgcc ctgggccaga ccgtgaccct gaccctgcac    1440
atggccgtgg gcccctgag ggtgagcgcc ggcgtgatca ggctgaggcc cgtgaggatg    1500
agggacggcg tgcactggag caggatcagg ctggccgaca gggcccacct ggagccctgg    1560
gagcccagcg ccgacggcga gtggaccgtg aggcacaccg tggccgcctg gccgccgtg    1620
tgcagcggcc tgaggagcga ggccaggaac ggcaggatgc tgccctacgt gatcgagctg    1680
gacggccagt tctgcggcca gctgaccatc ggcaacgtga cccacggcgc cctgaggagc    1740
gcctggatcg gctactgggt gcccagcgcc gccaccggcg gcggcgtggc caccggcgcc    1800
ctggcccctgg gcctggacca ctgcttcggc ccgtgatgc tgcacagggt ggaggccacc    1860
gtgaggcccg agaacgccgc cagcagggcc gtgctggcca agtggggctt cagggaggag    1920
ggcctgctga ggaggtacct ggaggtggac agggcctgga gggaccacct gctgatggcc    1980
atcaccgtgg aggaggtgta cggcagcgtg gccagcaccc tggtgagggc cggccacgcc    2040
agctggccct accctacga cgtgcccgac tacgcctga                           2079

SEQ ID NO: 71           moltype = AA  length = 692
FEATURE                 Location/Qualifiers
REGION                  1..692
                        note = Rv0012-Rv0990c-Rv0995 fusion protein
source                  1..692
                        mol_type = protein
                        organism = synthetic construct
SEQUENCE: 71
MRLTHPTPCP ENGETMIDRR RSAWRFSVPL VCLLAGLLLA ATHGVSGGTE IRRSDAPRLV     60
DLVRRAQASV NRLATEREAL TTRIDSVHGR SVDTALAAMQ RRSAKLAGVA AMNPVHGPGL    120
VVTLQDAQRD ANGRFPRDAS PDDLVVHQQD IEAVLNALWN AGAEAIQMQD QRIIAMSIAR    180
CVGNTLLLNG RTYSPPYTIA AIGDAAAMQA ALAAAPLVTL YKQYVVRFGL GYCEEVHPDL    240
QIVGYADPVR MHFAQPAGPL DYVAESSLNP SLVSRISAFL RPDWTRTVRA RRFAAAGLVM    300
LAGVAALRSN PEDDRSEVVV AAHDLRPGTA LTPGDVRLEK RSATTLPDGS QADLDAVVGS    360
TLASPTRRGE VLTDVRLLGS RLAESTAGPD ARIVPLHLAD SALVDLVRVG DVVDVLAAPV    420
TDSPAALRLL ATDAIVVLVS AQQKAQAADS DRVVLVALPA RLANTVAGAA LGQTVTLTLH    480
MAVGPLRVSA GVIRLRPVRM RDGVHWSRIR LADRAHLEPW EPSADGEWTV RHTVAAWPAV    540
CSGLRSEARN GRMLPYVIEL DGQFCGQLTI GNVTHGALRS AWIGYWVPSA ATGGGVATGA    600
LALGLDHCFG PVMLHRVEAT VRPENAASRA VLAKVGFREE GLLRRYLEVD RAWRDHLLMA    660
ITVEEVYGSV ASTLVRAGHA SWPYPYDVPD YA                                 692
```

TUBERCULOSIS ANTIGEN CASSETTES

REFERENCE TO SEQUENCE LISTING

This application includes a Sequence Listing filed electronically as an XML file named 901513169SEQ, created on Mar. 16, 2023, with a size of 122,055 bytes. The Sequence Listing is incorporated herein by reference.

FIELD

The present disclosure is directed, in part, to fusion proteins comprising *Mycobacterium tuberculosis* (Mtb) antigens, nucleic acid molecules encoding the same, vectors comprising nucleic acid molecules, compositions comprising the same, and methods of eliciting an immune response against tuberculosis.

BACKGROUND

Tuberculosis (TB) is a global health problem resulting in 8 million new cases and 2 million deaths each year. The emergence of multi-drug and totally-drug resistant strains of TB only makes this problem more severe. The life cycle of Mtb has 3 stages. In the acute phase following initial infection the bacteria replicate in the host and virulence factors are expressed, leading to the generation of an immune response by the host. As the immune response begins to control the infection, the Mtb enters a latent, asymptomatic state in which the bacteria become non-replicating and are encased in granulomas. The bacterium can persist in this latent state in infected individuals for many years, making diagnosis and treatment of disease difficult. In some cases, the bacteria are reactivated and begin replicating again, leading back to the disease state. Reactivation can occur for numerous reasons, including immune suppression caused by diseases such as HIV, treatments such as chemotherapy, or the weakening of the immune system due to aging. An estimated 2 billion people are latently infected with Mtb worldwide, and reactivation of latent Mtb accounts for most new cases of active TB disease. Reactivation is associated with inflammation, necrosis and cavitation of the lung, a process that results in draining of the lesions into the bronchus. Aerosols generated when individuals with bronchial lesions cough causes dissemination of the Mtb organism to uninfected, susceptible persons, and the transmission cycle is thus maintained.

The only currently available vaccine against TB, *Mycobacterium bovis* (Bacille Calmette-Guérin) (BCG), was first introduced in 1921. BCG has been widely utilized and while studies show that for some purposes BCG is effective (e.g., against disseminated TB), it is known to be ineffective with respect to preventing the development, persistence and reactivation of latent TB. There is an ongoing need to develop improved, more effective vaccines against TB. In particular, there is a need to develop vaccines that provide protection against the development, maintenance and/or reactivation of latent tuberculosis infection. With the availability of the entire genomic sequence of Mtb, and the tools for bioinformatic and experimental analysis of Mtb antigens, many new potential Mtb vaccine candidates have been identified in recent years. These include antigens that are involved in acute infection, maintenance of latency, or reactivation of Mtb. There are a range of delivery strategies in clinical development that are comprised of combinations of these and other antigens that have been tested in animal models and are currently or will soon be in clinical trials.

While vaccines are often effective to immunize individuals prophylactically or therapeutically against pathogen infection or human diseases, there is a need for improved vaccines. There is also a need for compositions and methods that produce an enhanced immune response. Likewise, while some immunotherapeutics are useful to modulate immune response in a patient, there remains a need for improved immunotherapeutic compositions and methods.

SUMMARY

The present disclosure describes antigen cassettes (and specified variants) that can be used to create tuberculosis vaccines comprising specified *Mycobacterium tuberculosis* (Mtb) antigens. The disclosure also describes the strategic combination of antigens which are incorporated into a variety of delivery platforms in such a way as to provide pathways to a matrix of matched combinations of antigen delivery to obtain an optimized immune response. The subject matter described herein can be used as a prophylactic or therapeutic TB vaccine. Specific selection of antigens for inclusion into a usable cassette was based on a number of additional parameters including, for example, a thorough review of the literature, expression data, responses by human T cells, inclusion of human immunogenic regions, mouse protection studies, and conservation in sequence across most strains of TB with full genome sequences (or lack thereof for the Variable antigens).

The constructs described herein can be integrated into several delivery platforms that include the following classes (but not exhaustive) of representative delivery platforms: 1) viral vector delivery systems, 2) recombinant BCG, 3) recombinant purified protein fusions, 4) DNA plasmid vector systems, and 5) RNA vector systems. These delivery platforms can be used either in a single platform alone or in combinations as matched antigen prime-boost approaches. In addition, the use of these antigens in a single rBCG vector system, which is envisioned to be used as an antigen matched prime for a boost with any of the modalities above, including protein, viral vectors, nucleic acids, or others.

The present disclosure provides fusion proteins that comprise at least two PE Mtb antigens, at least two PPE Mtb antigens, at least two ESX Mtb antigens, or at least two variable Mtb antigens.

The present disclosure also provides nucleic acid molecules encoding fusion proteins that comprise at least two PE Mtb antigens, at least two PPE Mtb antigens, at least two ESX Mtb antigens, or at least two variable Mtb antigens.

The present disclosure also provides: compositions comprising the fusion proteins and a pharmaceutically acceptable carrier; vectors encoding the fusion proteins; compositions comprising the vectors and a pharmaceutically acceptable carrier; cells comprising the vectors; compositions comprising the cells and a pharmaceutically acceptable carrier.

The present disclosure also provides compositions that comprise at least two PE Mtb antigens, at least two PPE Mtb antigens, at least two ESX Mtb antigens, or at least two variable Mtb antigens, and a pharmaceutically acceptable carrier.

The present disclosure also provides compositions that comprise at least two Mtb antigens, wherein the composition comprises at least one nucleic acid molecule encoding at least one of the Mtb antigens, and a pharmaceutically acceptable carrier.

The present disclosure also provides methods of eliciting an immune response against *Mycobacterium tuberculosis* in a mammal comprising administering to the mammal an immunologically sufficient amount of one or more fusion proteins described herein.

The present disclosure also provides methods of eliciting an immune response against *Mycobacterium tuberculosis* in a mammal comprising administering to the mammal an immunologically sufficient amount of a composition comprising one or more fusion proteins described herein, and a pharmaceutically acceptable carrier.

The present disclosure also provides methods of eliciting an immune response against *Mycobacterium tuberculosis* in a mammal comprising administering to the mammal an immunologically sufficient amount of a composition comprising one or more fusion proteins described herein, and a pharmaceutically acceptable carrier, wherein the composition comprises at least one nucleic acid molecule encoding at least one of the Mtb antigens.

The present disclosure also provides any one or more of the fusion proteins described herein for use in the preparation of a medicament for treating or preventing a *Mycobacterium tuberculosis* infection.

The present disclosure also provides any one or more of the fusion proteins described herein for use inn treating or preventing a *Mycobacterium tuberculosis* infection.

The present disclosure also provides use of any one or more of the fusion proteins described herein in the preparation of a medicament for treating or preventing a *Mycobacterium tuberculosis* infection.

The present disclosure also provides use of any one or more of the fusion proteins described herein in treating or preventing a *Mycobacterium tuberculosis* infection.

The present disclosure also provides compositions for use in the preparation of a medicament for treating or preventing a *Mycobacterium tuberculosis* infection, wherein the composition comprises any one or more of the fusion proteins described herein, and a pharmaceutically acceptable carrier.

The present disclosure also provides any one or more of the compositions described herein for use in treating or preventing a *Mycobacterium tuberculosis* infection, and a pharmaceutically acceptable carrier.

The present disclosure also provides any one or more of the compositions described herein in the preparation of a medicament for treating or preventing a *Mycobacterium tuberculosis* infection, and a pharmaceutically acceptable carrier.

The present disclosure also provides use of any one or more of the compositions described herein in treating or preventing a *Mycobacterium tuberculosis* infection, and a pharmaceutically acceptable carrier.

The present disclosure also provides any one or more of the compositions described herein for use in the preparation of a medicament for treating or preventing a *Mycobacterium tuberculosis* infection, and a pharmaceutically acceptable carrier; wherein the composition comprises at least one nucleic acid molecule encoding at least one of the Mtb antigens.

The present disclosure also provides any one or more of the compositions described herein for use in treating or preventing a *Mycobacterium tuberculosis* infection, and a pharmaceutically acceptable carrier, wherein the composition comprises at least one nucleic acid molecule encoding at least one of the Mtb antigens.

The present disclosure also provides use of any one or more of the compositions described herein in the preparation of a medicament for treating or preventing a *Mycobacterium tuberculosis* infection, and a pharmaceutically acceptable carrier, wherein the composition comprises at least one nucleic acid molecule encoding at least one of the Mtb antigens.

The present disclosure also provides use of any one or more of the compositions described herein in treating or preventing a *Mycobacterium tuberculosis* infection, and a pharmaceutically acceptable carrier, wherein the composition comprises at least one nucleic acid molecule encoding at least one of the Mtb antigens.

The present disclosure also provides fusion proteins, compositions, cells, vectors, methods, and uses, as described herein, substantially as described herein.

DESCRIPTION OF EMBODIMENTS

The terminology used herein is for the purpose of describing particular embodiments only and is not intended to be limiting.

As used herein, the singular forms "a," "an" and "the" include plural referents unless the context clearly dictates otherwise.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

As used herein, "adjuvant" means any molecule added to any composition described herein to enhance the immunogenicity of the Mtb antigens.

As used herein, "coding sequence" or "encoding nucleic acid" means the nucleic acids (RNA or DNA molecule) that comprise a nucleotide sequence which encodes an Mtb antigen. The coding sequence can further include initiation and termination signals operably linked to regulatory elements including a promoter and polyadenylation signal capable of directing expression in the cells of an individual or mammal to which the nucleic acid is administered.

As used herein, "consensus" or "consensus sequence" means a polypeptide sequence based on analysis of an alignment of multiple subtypes of a particular Mtb antigen. Nucleic acid sequences that encode a consensus polypeptide sequence can be prepared. Vaccines comprising Mtb antigens that comprise consensus sequences and/or nucleic acid molecules that encode such antigens can be used to induce broad immunity against multiple subtypes or serotypes of a particular antigen.

As used herein, "electroporation" means the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

As used herein, "fragment" respect to nucleic acid sequences, means a nucleic acid sequence or a portion thereof, that encodes a portion of an Mtb antigen capable of eliciting an immune response in a mammal that cross reacts with a full length wild type Mtb antigen. The fragments can be DNA fragments selected from at least one of the various nucleotide sequences that encode protein fragments set forth below.

As used herein, "fragment" or "immunogenic fragment" with respect to polypeptide sequences, means a portion of an Mtb antigen capable of eliciting an immune response in a mammal that cross reacts with a full length wild type strain Mtb antigen. Fragments of consensus or wild type Mtb antigens can comprise at least 10%, at least 20%, at least 30%, at least 40%, at least 50%, at least 60%, at least 70%, at least 80%, at least 90% or at least 95% of a consensus or wild type Mtb antigen. In some embodiments, fragments of consensus proteins can comprise at least 20 amino acids or more, at least 30 amino acids or more, at least 40 amino acids or more, at least 50 amino acids or more, at least 60 amino acids or more, at least 70 amino acids or more, at least 80 amino acids or more, at least 90 amino acids or more, at least 100 amino acids or more, at least 110 amino acids or more, at least 120 amino acids or more, at least 130 amino acids or more, at least 140 amino acids or more, at least 150 amino acids or more, at least 160 amino acids or more, at least 170 amino acids or more, at least 180 amino acids or more of a consensus or wild type protein.

As used herein, "genetic construct" refers to the DNA or RNA molecules that comprise a nucleotide sequence which encodes an Mtb antigen. The coding sequence includes initiation and termination signals operably linked to regulatory elements including a promoter and polyadenylation signal capable of directing expression in the cells of the individual to whom the nucleic acid molecule is administered.

As used herein, "expressible form" refers to gene constructs that contain the necessary regulatory elements operable linked to a coding sequence that encodes an Mtb antigen such that when present in the cell of the individual, the coding sequence will be expressed.

As used herein, "homology" refers to a degree of complementarity. There can be partial homology or complete homology (i.e., identity). A partially complementary sequence that at least partially inhibits a completely complementary sequence from hybridizing to a target nucleic acid is referred to using the functional term "substantially homologous." When used in reference to a double-stranded nucleic acid sequence such as a cDNA or genomic clone, the term "substantially homologous" refers to a probe that can hybridize to a strand of the double-stranded nucleic acid sequence under conditions of low stringency. When used in reference to a single-stranded nucleic acid sequence, the term "substantially homologous" refers to a probe that can hybridize to (i.e., is the complement of) the single-stranded nucleic acid template sequence under conditions of low stringency.

As used herein, "identical" or "identity" in the context of two or more nucleic acids or polypeptide sequences, means that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) residues can be considered equivalent. Identity can be performed manually or by using a computer sequence algorithm such as BLAST or BLAST 2.0.

As used herein, "immune response" means the activation of a host's immune system, e.g., that of a mammal, in response to the introduction of an Mtb antigen. The immune response can be in the form of a cellular or humoral response, or both.

As used herein, "Mtb antigen" means an antigen from *Mycobacterium tuberculosis*, which may be an isolated antigen, or an antigen that forms part of a fusion protein with other antigen(s).

As used herein, "nucleic acid" or "oligonucleotide" or "polynucleotide" means at least two nucleotides covalently linked together. The depiction of a single strand also defines the sequence of the complementary strand. Thus, a nucleic acid also encompasses the complementary strand of a depicted single strand. Many variants of a nucleic acid can be used for the same purpose as a given nucleic acid. Thus, a nucleic acid also encompasses substantially identical nucleic acids and complements thereof. A single strand provides a probe that can hybridize to a target sequence under stringent hybridization conditions. Thus, a nucleic acid also encompasses a probe that hybridizes under stringent hybridization conditions. Nucleic acids can be single stranded or double stranded, or can contain portions of both double stranded and single stranded sequence. The nucleic acid can be DNA, both genomic and cDNA, RNA, or a hybrid, where the nucleic acid can contain combinations of deoxyribo- and ribo-nucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods.

As used herein, "operably linked" means that expression of a gene is under the control of a promoter with which it is spatially connected. A promoter can be positioned 5' (upstream) or 3' (downstream) of a gene under its control. The distance between the promoter and a gene can be approximately the same as the distance between that promoter and the gene it controls in the gene from which the promoter is derived. As is known in the art, variation in this distance can be accommodated without loss of promoter function.

As used herein, "promoter" means a synthetic or naturally-derived molecule which is capable of conferring, activating or enhancing expression of a nucleic acid in a cell. A promoter can comprise one or more specific transcriptional regulatory sequences to further enhance expression and/or to alter the spatial expression and/or temporal expression of same. A promoter can also comprise distal enhancer or repressor elements, which can be located as much as several thousand base pairs from the start site of transcription. A promoter can be derived from sources including viral, bacterial, fungal, plants, insects, and animals. A promoter can regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents.

As used herein, "stringent hybridization conditions" means conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions can be selected to be about 5 to 10° C. lower than the thermal melting point ($T_m$) for the specific sequence at a defined ionic strength pH. The $T_m$ can be the temperature (under defined ionic strength, pH, and nucleic concentration) at which 50% of the probes complementary to the target hybridize to the target sequence at equilibrium (as the target sequences are present in excess, at T$_m$, 50% of the probes are occupied at equilibrium). Stringent conditions can be those in which the salt concentration is less than about 1.0 M sodium ion, such as about 0.01 to 1.0 M sodium ion concentration (or other salts) at pH 7.0 to 8.3 and the temperature is at least about 30° C. for short probes (e.g., about 10 to 50 nucleotides) and at least about 60° C. for long probes (e.g., greater than about 50 nucleotides). Stringent conditions can also be achieved with the addition of destabilizing agents such as formamide. For selective or specific hybridization, a positive signal can be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

As used herein, "substantially complementary" means that a first sequence is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540, or more nucleotides or amino acids, or that the two sequences hybridize under stringent hybridization conditions.

As used herein, "substantially identical" means that a first and second sequence are at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540 or more nucleotides or amino acids, or with respect to nucleic acids, if the first sequence is substantially complementary to the complement of the second sequence.

As used herein, "variant" with respect to a nucleic acid means: i) a portion or fragment of a referenced nucleotide sequence; ii) the complement of a referenced nucleotide sequence or portion thereof; iii) a nucleic acid that is substantially identical to a referenced nucleic acid or the complement thereof; or iv) a nucleic acid that hybridizes under stringent conditions to the referenced nucleic acid, complement thereof, or a sequences substantially identical thereto.

As used herein, "variant" with respect to a peptide or polypeptide means that it differs in amino acid sequence by the insertion, deletion, or conservative substitution of amino acids, but retains at least one biological activity. Variant can also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. Amino acid substitutions that are compatible with biological function are understood to depend on the relative similarity of the amino acids, and particularly the side chains of those amino acids, as revealed by the hydrophobicity, hydrophilicity, charge, size, and other properties.

As used herein, "vector" means a nucleic acid sequence containing an origin of replication. A vector can be a viral vector, bacteriophage, bacterial artificial chromosome or yeast artificial chromosome. A vector can be a DNA or RNA vector. A vector can be a self-replicating extrachromosomal vector.

The present disclosure provides fusion proteins comprising at least two Mtb antigens. In some embodiments, the fusion protein comprises at least three Mtb antigens. In some embodiments, the fusion protein comprises at least four Mtb antigens. In some embodiments, the fusion protein comprises at least five Mtb antigens. In some embodiments, the fusion protein comprises at least six Mtb antigens. In some embodiments, the fusion protein comprises at least seven Mtb antigens.

In some embodiments, the nucleic acid molecule encoding any particular Ma) antigen can be a mycobacterial sequence, a bacterial codon optimized sequence (such as an *E. coli* optimized sequence), or a mammalian optimized sequence (such as a human optimized sequence). The *E. coli* optimized sequences can be used, for example, to produce fusion proteins. The human optimized sequences can be used in, for example, viral vectors. Methods of codon optimization (whether for bacterial or mammalian) are well known to the skilled artisan.

In some embodiments, any of the fusion proteins described herein can comprise a C-terminal HA tag (e.g., YPYDVPDYA) (SEQ ID NO:17).

In some embodiments, the Mtb antigen is a PE antigen. In some embodiments, the PE antigen is Rv3872 (also known as PE35), Rv1.788 (also known as PE18), Rv3893c (also known as 13E36), Rv0285 (also known as PE5), Rv1818c (also known as PE_PGRS33; includes only the PE domain), Rv0159c (also known as PE3; includes only the PE domain), or Rv1172c (also known as PE12; includes only the PE domain).

A nucleotide sequence encoding Rv3872 is shown in Table 1 as SEQ ID NO:1 and an amino acid sequence of Rv3872 is shown in Table 1 as SEQ ID NO:2.

A nucleotide sequence encoding Rv1788 is shown in Table 1 as SEQ ID NO:3, and an amino acid sequence of Rv1788 is shown in Table 1 as SEQ ID NO:4.

A nucleotide sequence encoding Rv3893c is shown in Table 1 as SEQ ID NO:5, and an amino acid sequence of Rv3893c is shown in Table 1 as SEQ ID NO:6.

A nucleotide sequence encoding Rv0285 is shown in Table 1 as SEQ ID NO:7, and an amino acid sequence of Rv0285 is shown in Table 1 as SEQ ID NO:8.

A nucleotide sequence encoding Rv1818c is shown in Table 1 as SEQ ID NO:9, and an amino acid sequence of Rv1818c is shown in Table 1 as SEQ ID NO:10.

A nucleotide sequence encoding Rv0159c is shown in Table 1 as SEQ ID NO: 11, and an amino acid sequence of Rv0159c is shown in Table 1 as SEQ ID NO:12.

A nucleotide sequence encoding Rv1172c is shown in Table 1 as SEQ ID NO:13, and an amino acid sequence of Rv1172c is shown in Table 1 as SEQ ID NO:14.

TABLE 1

PE Antigens

| Construct | nucleotide sequence<br>amino acid sequence |
|---|---|
| Rv3872<br>(PE35) | ATGGAGAAGATGAGCCACGACCCCATCGCCGCCGACATCGGCA<br>CCCAGGTGAGCGACAACGCCCTGCACGGCGTGACCGCCGGCAG |

TABLE 1-continued PE Antigens

| Construct | nucleotide sequence<br>amino acid sequence |
|---|---|
| | CACCGCCCTGACCAGCGTGACCGGCCTGGTGCCCGCCGGCGCC<br>GACGAGGTGAGCGCCCAGGCCGCCACCGCCTTCACCAGCGAGG<br>GCATCCAGCTGCTGGCCAGCAACGCCAGCGCCCAGGACCAGCT<br>GCACAGGGCCGGCGAGGCCGTGCAGGACGTGGCCAGGACCTA<br>CAGCCAGATCGACGACGGCGCCGCCGGCGTGTTCGCCGAGTGA<br>(SEQ ID NO: 1)<br><br>MEKMSHDPIAADIGTQVSDNALHGVTAGSTALTSVTGLVPAGAD<br>EVSAQAATAFTSEGIQLLASNASAQDQLHRAGEAVQDVARTYSQI<br>DDGAAGVFAE (SEQ ID NO: 2) |
| Rv1788<br>(PE18) | ATGAGCTTCGTGACCACCCAGCCCGAGGCCCTGGCCGCCGCCG<br>CCGGCAGCCTGCAGGGCATCGGCAGCGCCCTGAACGCCCAGAA<br>CGCCGCCGCCGCCACCCCCACCACCGGCGTGGTGCCCGCCGCC<br>GCCGACGAGGTGAGCGCCCTGACCGCCGCCCAGTTCGCCGCCC<br>ACGCCCAGATCTACCAGGCCGTGAGCGCCCAGGCCGCCGCCAT<br>CCACGAGATGTTCGTGAACACCCTGCAGATGAGCAGCGGCAGC<br>TACGCCGCCACCGAGGCCGCCAACGCCGCCGCCGCCGGCTGA<br>(SEQ ID NO: 3)<br><br>MSFVTTQPEALAAAAGSLQGIGSALNAQNAAAATPTTGVVPAAA<br>DEVSALTAAQFAAHAQIYQAVSAQAAAIHEMEVNTLQMSSGSYA<br>ATEAANAAAAG (SEQ ID NO: 4) |
| Rv3893c<br>(PE36) | ATGGTGTGGAGCGTGCAGCCCGAGGCCGTGCTGGCCAGCGCCG<br>CCGCCGAGAGCGCCATCAGCGCCGAGACCGAGGCCGCCGCCGC<br>CGGCGCCGCCCCCGCCCTGCTGAGCACCACCCCCATGGGCGGC<br>GACCCCGACAGCGCCATGTTCAGCGCCGCCCTGAACGCCTGCG<br>GCGCCAGCTACCTGGGCGTGGTGGCCGAGCACGCCAGCCAGAG<br>GGGCCTGTTCGCCGGCTGA (SEQ ID NO: 5)<br><br>MVWSVQPEAVLASAAAESAISAETEAAAAGAAPALLSTTPMGGD<br>PDSAMFSAALNACGASYLGVVAEHASQRGLFAG (SEQ ID NO: 6) |
| Rv0285<br>(PE5) | ATGACCCTGAGGGTGGTGCCCGAGGGCCTGGCCGCCGCCAGCG<br>CCGCCGTGGAGGCCCTGACCGCCAGGCTGGCCGCCGCCCACGC<br>CAGCGCCGCCCCCGTGATCACCGCCGTGGTGCCCCCCGCCGCC<br>GACCCCGTGAGCCTGCAGACCGCCGCCGGCTTCAGCGCCCAGG<br>GCGTGGAGCACGCCGTGGTGACCGCCGAGGGCGTGGAGGAGCT<br>GGGCAGGGCCGGCGTGGGCGTGGGCGAGAGCGGCGCCAGCTA<br>CCTGGCCGGCGACGCCGCCGCCGCCACCTACGGCGTGGTG<br>GGCGGCTGA (SEQ ID NO: 7)<br><br>MTLRVVPEGLAAASAAVEALTARLAAAHASAAPVITAVVPPAAD<br>PVSLQTAAGFSAQGVEHAVVTAEGVEELGRAGVGVGESGASYLA<br>GDAAAAATYGVVGG (SEQ ID NO: 8) |
| Rv1818c<br>(PE_PGRS33) | ATGAGCTTCGTGGTGACCATCCCCGAGGCCCTGGCCGCCGTGG<br>CCACCGACCTGGCCGGCATCGGCAGCACCATCGGCACCGCCAA<br>CGCCGCCGCCGCCGTGCCCACCACCACCGTGCTGGCCGCCGCC<br>GCCGACGAGGTGAGCGCCGCCATGGCCGCCCTGTTCAGCGGCC<br>ACGCCCAGGCCTACCAGGCCCTGAGCGCCCAGGCCGCCCTGTT<br>CCACGAGCAGTTCGTGAGGGCCCTGACCGCCGGCGCCGGCAGC<br>TACGCCGCCGCCGAGGCCGCCAGCGCCGCCCCCCTGGAGGGC<br>TGA (SEQ ID NO: 9)<br><br>MSFVVTIPEALAAVATDLAGIGSTIGTANAAAAVPTTTVLAAAAD<br>EVSAAMAALFSGHAQAYQALSAQAALFHEQFVRALTAGAGSYA<br>AEAASAAPLEG (SEQ ID NO: 10) |
| Rv0159c<br>(PE3) | ATGAGCTACGTGATCGCCGCCCCCGAGATGCTGGCCACCACCG<br>CCGCCGACGTGGACGGCATCGGCAGCGCCATCAGGGCCGCCAG<br>CGCCAGCGCCGCCGGCCCCACCACCGGCCTGCTGGCCGCCGCC<br>GCCGACGAGGTGAGCAGCGCCGCCGCCGCCCTGTTCAGCGAGT<br>ACGCCAGGGAGTGCCAGGAGGTGCTGAAGCAGGCCGCCGCCTT<br>CCACGGCGAGTTCACCAGGGCCCTGGCCGCCGCCGGCGCCGCC<br>TACGCCCAGGCCGAGGCCAGCAACACCGCCGCCATGAGCGGC<br>ACCGCCGGCAGCAGCGGCGCCCTGGGCAGCTGA (SEQ ID<br>NO: 11)<br><br>MSYVIAAPEMLATTAADVDGIGSAIRAASASAAGPTTGLLAAAAD<br>EVSSAAAALFSEYARECQEVLKQAAAFHGEFTRALAAAGAAYAQ<br>AEASNTAAMSGTAGSSGALGS (SEQ ID NO: 12) |

TABLE 1-continued

PE Antigens

| Construct | nucleotide sequence<br>amino acid sequence |
|---|---|
| Rv1172c<br>(PE12) | ATGAGCTTCGTGTTCGCCGCCCCGAGGCCCTGGCCGCCGCCGC<br>CGCCGACATGGCCGGCATCGGCAGCACCCTGAACGCCGCCAAC<br>GTGGTGGCCGCCGTGCCCACCACCGGCGTGCTGGCCGCCGCCG<br>CCGACGAGGTGAGCACCCAGGTGGCCGCCCTGCTGAGCGCCCA<br>CGCCCAGGGCTACCAGCAGCTGAGCAGGCAGATGATGACCGCC<br>TTCCACGACCAGTTCGTGCAGGCCCTGAGGGCCAGCGCCGACG<br>CCTACGCCACCGCCGAGGCCAGCGCCGCCCAGACCATGGTGAA<br>CGCCGTGAACGCCCCCGCCAGGGCCCTGTGA (SEQ ID NO: 13)<br><br>MSFVFAAPEALAAAAADMAGIGSTLNAANVVAAVPTTGVLAAA<br>ADEVSTQVAALLSAHAQGYQQLSRQMMTAFHDQFVQALRASAD<br>AYATAEASAAQTMVNAVNAPARAL (SEQ ID NO: 14) |

In some embodiments, a composition comprises at least two of the PE antigens. In some embodiments, the composition comprises at least three of the PE antigens. In some embodiments, the composition comprises at least four of the PE antigens. In some embodiments, the composition comprises at least five of the PE antigens. In some embodiments, the composition comprises at least six of the PE antigens. In some embodiments, the composition comprises all seven PE antigens. In some embodiments, the composition comprises from at least two to seven of the PE antigens. In some embodiments, the composition comprises from at least three to seven of the PE antigens. In some embodiments, the composition comprises from at least four to seven of the PE antigens. In some embodiments, the composition comprises at least five to seven of the PE antigens. In some embodiments, the composition comprises six or seven of the PE antigens. In some embodiments, the composition further comprises a pharmaceutically acceptable carrier.

In some embodiments, the fusion protein comprises at least two of the PE antigens. In some embodiments, the fusion protein comprises at least three of the PE antigens. In some embodiments, the fusion protein comprises at least four of the PE antigens. In some embodiments, the fusion protein comprises at least five of the PE antigens. In some embodiments, the fusion protein comprises at least six of the PE antigens. In some embodiments, the fusion protein comprises all seven PE antigens. In some embodiments, the fusion protein comprises from at least two to seven of the PE antigens. In some embodiments, the fusion protein comprises from at least three to seven of the PE antigens. In some embodiments, the fusion protein comprises from at least four to seven of the PE antigens. In some embodiments, the fusion protein comprises at least five to seven of the PE antigens. In some embodiments, the fusion protein comprises six or seven of the PE antigens.

In some embodiments, the fusion protein comprises Rv3872 and Rv1788. In some embodiments, the fusion protein comprises Rv3893c, Rv0285, and Rv1818c. In some embodiments, the fusion protein comprises Rv0159c and Rv1172c.

In any of the embodiments of fusion proteins set forth herein, the individual PE antigens can be present in any order. For example, for a fusion protein comprising Rv3893c, Rv0285, and Rv1818c antigens, the first (or N-terminal) antigen may be Rv3893c, Rv0285, or Rv1818c; the second antigen may be Rv3893c, Rv0285, or Rv1818c (whichever one is not the first PE antigen); and the third antigen may be Rv3893c, Rv0285, or Rv1818c (whichever one is not the first or second PE antigen). Likewise for every fusion protein disclosed herein.

Individual PE antigens may be linked together in a C-terminus to N-terminus or N-terminus to C-terminus manner without any linker. Alternately, a linker may be present between any two PE antigens within any of the fusion proteins disclosed herein. In some embodiments, the linker is a segment of DNA or RNA optionally containing one or more restrictions sites, wherein the linker is inserted between nucleic acid molecules encoding two PE antigens of any of the fusion proteins disclosed herein.

In some embodiments, the fusion protein comprises Rv3872-Rv1788-Rv3893c-Rv0285-Rv1818c-Rv0159c-Rv1172c (Construct A; see Table 2). The nucleotide sequence is SEQ ID NO:15, and the corresponding amino acid sequence is SEQ ID NO:16 (with inserted AAA between Rv1788 and Rv3893c to disrupt possible epitope with homology to human proteins; C-terminal HA tag (YPYDVPDYA; SEQ ID NO:17) added).

TABLE 2

| PE Antigen Cassette | |
|---|---|
| Construct | nucleotide sequence<br>amino acid sequence |
| A | ATGGAGAAGATGAGCCACGACCCCA<br>TCGCCGCCGACATCGGCACCCAGGT<br>GAGCGACAACGCCCTGCACGGCGTG<br>ACCGCCGGCAGCACCGCCCTGACCA<br>GCGTGACCGGCCTGGTGCCCGCCGG<br>CGCCGACGAGGTGAGCGCCCAGGCC<br>GCCACCGCCTTCACCAGCGAGGGCA<br>TCCAGCTGCTGGCCAGCAACGCCAG<br>CGCCCAGGACCAGCTGCACAGGGCC<br>GGCGAGGCCGTGCAGGACGTGGCCA<br>GGACCTACAGCCAGATCGACGACGG<br>CGCCGCCGGCGTGTTCGCCGAGATG<br>AGCTTCGTGACCACCCAGCCCGAGG<br>CCCTGGCCGCCGCCGCCGGCAGCCT<br>GCAGGGCATCGGCAGCGCCCTGAAC<br>GCCCAGAACGCCGCCGCCGCCACCC<br>CCACCACCGGCGTGGTGCCCGCCGC<br>CGCCGACGAGGTGAGCGCCCTGACC<br>GCCGCCCAGTTCGCCGCCCACGCCC<br>AGATCTACCAGGCCGTGAGCGCCCA<br>GGCCGCCGCCATCCACGAGATGTTC<br>GTGAACACCCTGCAGATGAGCAGCG<br>GCAGCTACGCCGCCACCGAGGCCGC<br>CAACGCCGCCGCCGCCGGCGCCGCC<br>GCCATGGTGTGGAGCGTGCAGCCCG<br>AGGCCGTGCTGGCCAGCGCCGCCGC<br>CGAGAGCGCCATCAGCGCCGAGACC<br>GAGGCCGCCGCCGCCGGCGCCGCCC |

TABLE 2-continued

PE Antigen Cassette

| Construct | nucleotide sequence<br>amino acid sequence |
|---|---|
| | CCGCCCTGCTGAGCACCACCCCCAT<br>GGGCGGCGACCCCGACAGCGCCATG<br>TTCAGCGCCGCCCTGAACGCCTGCG<br>GCGCCAGCTACCTGGGCGTGGTGGC<br>CGAGCACGCCAGCCAGAGGGGCCTG<br>TTCGCCGGCATGACCCTGAGGGTGG<br>TGCCCGAGGGCCTGGCCGCCGCCAG<br>CGCCGCCGTGGAGGCCCTGACCGCC<br>AGGCTGGCCGCCGCCCACGCCAGCG<br>CCGCCCCCGTGATCACCGCCGTGGT<br>GCCCCCCGCCGCCGACCCCGTGAGC<br>CTGCAGACCGCCGCCGGCTTCAGCG<br>CCCAGGGCGTGGAGCACGCCGTGGT<br>GACCGCCGAGGGCGTGGAGGAGCTG<br>GGCAGGGCCGGCGTGGGCGTGGGCG<br>AGAGCGGCGCCAGCTACCTGGCCGG<br>CGACGCCGCCGCCGCCGCCACCTAC<br>GGCGTGGTGGGGGGCATGAGCTTCG<br>TGGTGACCATCCCCGAGGCCCTGGC<br>CGCCGTGGCCACCGACCTGGCCGGC<br>ATCGGCAGCACCATCGGCACCGCCA<br>ACGCCGCCGCCGCCGTGCCCACCAC<br>CACCGTGCTGGCCGCCGCCGCCGAC<br>GAGGTGAGCGCCGCCATGGCCGCCC<br>TGTTCAGCGGCCACGCCCAGGCCTA<br>CCAGGCCCTGAGCGCCCAGGCCGCC<br>CTGTTCCACGAGCAGTTCGTGAGGG<br>CCCTGACCGCCGGCGCCGGCAGCTA<br>CGCCGCCATGAGCTACGTGATCGCC<br>GCCCCCGAGATGCTGGCCACCACCG<br>CCGCCGACGTGGACGGCATCGGCAG<br>CGCCATCAGGGCCGCCAGCGCCAGC<br>GCCGCCGGCCCCACCACCGGCCTGC<br>TGGCCGCCGCCGCCGACGAGGTGAG<br>CAGCGCCGCCGCCGCCCTGTTCAGC<br>GAGTACGCCAGGGAGTGCCAGGAGG<br>TGCTGAAGCAGGCCGCCGCCTTCCA<br>CGGCGAGTTCACCAGGGCCCTGGCC<br>GCCGCCGGCGCCGCCTACGCCCAGG<br>CCGAGGCCAGCAACACCGCCGCCAT<br>GAGCGGCACCGCCGGCAGCAGCGGC<br>GCCCTGGGCAGCATGAGCTTCGTGT<br>TCGCCGCCCCCGAGGCCCTGGCCGC<br>CGCCGCCGCCGACATGGCCGGCATC<br>GGCAGCACCCTGAACGCCGCCAACG<br>TGGTGGCCGCCGTGCCCACCACCGG<br>CGTGCTGGCCGCCGCCGCCGACGAG<br>GTGAGCACCCAGGTGGCCGCCCTGC<br>TGAGCGCCCACGCCCAGGGCTACCA<br>GCAGCTGAGCAGGCAGATGATGACC<br>GCCTTCCACGACCAGTTCGTGCAGG<br>CCCTGAGGGCAGCGCCGACGCCTA<br>CGCCACCGCCGAGGCCAGCGCCGCC<br>CAGACCATGGTGAACGCCGTGAACG<br>CCCCCGCCAGGGCCCTGTACCCCTA<br>CGACGTGCCCGACTACGCCTGA<br>(SEQ ID NO: 15)<br><br>MEKMSHDPIAADIGTQVSDNALHGV<br>TAGSTALTSVTGLVPAGADEVSAQA |

TABLE 2-continued

PE Antigen Cassette

| Construct | nucleotide sequence<br>amino acid sequence |
|---|---|
| | ATAFTSEGIQLLASNASAQDQLHRA<br>GEAVQDVARTYSQIDDGAAGVFAEM<br>SFVTTQPEALAAAAGSLQGIGSALN<br>AQNAAAATPTTGVVPAAADEVSALT<br>AAQFAAHAQIYQAVSAQAAAIHEMF<br>VNTLQMSSGSYAATEAANAAAAGAA<br>AMVWSVQPEAVLASAAAESAISAET<br>EAAAAGAAPALLSTTPMGGDPDSAM<br>FSAALNACGASYLGVVAEHASQRGL<br>FAGMTLRVVPEGLAAASAAVEALTA<br>RLAAAHASAAPVITAVVPPAADPVS<br>LQTAAGFSAQGVEHAVVTAEGVEEL<br>GRAGVGVGESGASYLAGDAAAAATY<br>GVVGGMSFVVTIPEALAAVATDLAG<br>IGSTIGTANAAAAVPTTTVLAAAAD<br>EVSAAMAALFSGHAQAYQALSAQAA<br>LFHEQFVRALTAGAGSYAAMSYVIA<br>APEMLATTAADVDGIGSAIRAASAS<br>AAGPTTGLLAAAADEVSSAAAALFS<br>EYARECQEVLKQAAAFHGEFTRALA<br>AAGAAYAQAEASNTAAMSGTAGSSG<br>ALGSMSFVFAAPEALAAAADMAGI<br>GSTLNAANVVAAVPTTGVLAAAADE<br>VSTQVAALLSAHAQGYQQLSRQMMT<br>AFHDQFVQALRASADAYATAEASAA<br>QTMVNAVNAPARALYPYDVPDYA<br>(SEQ ID NO: 16) |

In some embodiments, the Mtb antigen is a PPE antigen. In some embodiments, the PPE antigen is Rv3873 (also known as PPE68; includes only the PPE domain), Rv1387 (also known as PPE20; includes only the PPE domain), Rv3892c (also known as PPE69; includes only the PPE domain), Rv1789 (also known as PPE26; includes only the PPE domain), Rv1800 (also known as PPE28; includes only the PPE domain), or Rv1039c (also known as PPE15; includes only the PPE domain).

A nucleotide sequence encoding Rv3873 is shown in Table 3 as SEQ ID NO:18, and an amino acid sequence of Rv3873 is shown in Table 3 as SEQ ID NO:19.

A nucleotide sequence encoding Rv1387 is shown in Table 3 as SEQ ID NO:20, and an amino acid sequence of Rv1387 is shown in Table 3 as SEQ ID NO:21.

A nucleotide sequence encoding Rv3892c is shown in Table 3 as SEQ ID NO:22, and an amino acid sequence of Rv3892c is shown in Table 3 as SEQ ID NO:23.

A nucleotide sequence encoding Rv1789 is shown in Table 3 as SEQ ID NO:24, and an amino acid sequence of Rv1789 is shown in Table 3 as SEQ ID NO:25.

A nucleotide sequence encoding Rv1800 is shown in Table 3 as SEQ ID NO:26, and an amino acid sequence of Rv1800 is shown in Table 3 as SEQ ID NO:27.

A nucleotide sequence encoding Rv1039c is shown in Table 3 as SEQ ID NO:28, and an amino acid sequence of Rv1039c is shown in Table 3 as SEQ ID NO:29.

TABLE 3

PPE Antigens

| Construct | nucleotide sequence<br>amino acid sequence |
|---|---|
| Rv3873<br>(PPE68) | ATGCTGTGGCACGCCATGCCCCCCGAGCTGAACACCGCCAGGC<br>TGATGGCCGGCGCCGGCCCCGCCCCATGCTGGCCGCCGCCGC<br>CGGCTGGCAGACCCTGAGCGCCGCCCTGGACGCCCAGGCCGTG<br>GAGCTGACCGCCAGGCTGAACAGCCTGGGCGAGGCCTGGACCG<br>GCGGCGGCAGCGACAAGGCCCTGGCCGCCGCCACCCCCATGGT |

TABLE 3-continued

PPE Antigens

| Construct | nucleotide sequence<br>amino acid sequence |
|---|---|
| | GGTGTGGCTGCAGACCGCCAGCACCCAGGCCAAGACCCAGGGCC<br>ATGCAGGCCACCGCCCAGGCCGCCGCCTACACCCAGGCCATG<br>GCCACCACCCCCAGCCTGCCCGAGATCGCCGCCAACCACATCA<br>CCCAGGCCGTGCTGACCGCCACCAACTTCTTCGGCATCAACACC<br>ATCCCCATCGCCCTGACCGAGATGGACTACTTCATCAGGATGTG<br>GAACCAGGCCGCCCTGGCCATGGAGGTGTACCAGGCCGAGACC<br>GCCGTGAACACCCTGTTCGAGAAGCTGGAGCCCATGGCCAGCA<br>TCCTGGACCCCGGCGCCAGCCAGTGA (SEQ ID NO: 18)<br><br>MLWHAMPPELNTARLMAGAGPAPMLAAAAGWQTLSAALDAQA<br>VELTARLNSLGEAWTGGGSDKALAAATPMVVWLQTASTQAKTR<br>AMQATAQAAAYTQAMATTPSLPEIAANHITQAVLTATNFFGI<br>NTIPIALTEMDYFIRMWNQAALAMEVYQAETAVNTLFEKLEP<br>MASILDPGASQ (SEQ ID NO: 19) |
| Rv1387<br>(PPE20) | ATGACCGAGCCCTGGATCGCCTTCCCCCCCGAGGTGCACAGCG<br>CCATGCTGAACTACGGCGCCGGCGTGGGCCCCATGCTGATCAG<br>CGCCACCCAGAACGGCGAGCTGAGCGCCCAGTACGCCGAGGCC<br>GCCAGCGAGGTGGAGGAGCTGCTGGGCGTGGTGGCCAGCGAG<br>GGCTGGCAGGGCCAGGCCGCCGAGGCCTTCGTGGCCGCCTACA<br>TGCCCTTCCTGGCCTGGCTGATCCAGGCCAGCGCCGACTGCGTG<br>GAGATGGCCGCCCAGCAGCACGTGGTGATCGAGGCCTACACC<br>GCCGCCGTGGAGCTGATGCCCACCCAGGTGGAGCTGGCCGCCA<br>ACCAGATCAAGCTGGCCGTGCTGGTGGCCACCAACTTCTTCGG<br>CATCAACACCATCCCCATCGCCATCAACGAGGCCGAGTACGTG<br>GAGATGTGGGTGAGGGCCGCCACCACCATGGCCACCTACAGCA<br>CCGTGAGCAGGAGCGCCCTGAGCGCCATGCCCCACACCAGCCC<br>CCCCCCCCTGATCCTGAAGAGCGACTGA (SEQ ID NO: 20)<br><br>MTEPWIAFPPEVHSAMLNYGAGVGPMLISATQNGELSAQYAEAA<br>SEVEELLGVVASEGWQGQAAEAFVAAYMPFLAWLIQASADCVE<br>MAAQQHVVIEAYTAAVELMPTQVELAANQIKLAVLVATNFFGIN<br>TIPIAINEAEYVEMWVRAATTMATYSTVSRSALSAMPHTSPPPL<br>ILKSD (SEQ ID NO: 21) |
| Rv3892c<br>(PPE69) | ATGCCCGACCCCGGCTGGGCCGCCAGGACCCCCGAGGCCAACG<br>ACCTGCTGCTGACCGCCGGCACCGGCGTGGGCACCCACCTGGC<br>CAACCAGACCGCCTGGACCACCCTGGGCGCCAGCCACCACGCC<br>AGCGGCGTGGCCAGCGCCATCAACACCGCCGCCACCGCCGCCA<br>GCTGGCTGGGCGTGGGCAGCGCCGCCAGCGCCCTGAACGTGAC<br>CATGCTGAACGCCACCCTGCACGGCCTGGCCGGCTGGGTGGAC<br>GTGAAGCCCGCCGTGGTGAGCACCGCCATCGCCGCCTTCGAG<br>ACCGCCAACGCCGCCATGAGGCCCGCCCCCGAGTGCATGGAGA<br>ACAGGGACGAGTGGGGCGTGGACAACGCCATCAACCCCAGCGT<br>GCTGTGGACCCTGACCCCCAGGATCGTGAGCCTGGACGTGGAG<br>TACTTCGGCGTGATGTGGCCCAACAACGCCGCCGTGGGCGCCA<br>CCTACGGCGGCGTGCTGGCCGCCCTGGCCGAGAGCCTGGCCAT<br>CCCCCCCCCCGTGGCCACCATGGGCTGA (SEQ ID NO: 22)<br><br>MPDPGWAARTPEANDLLLTAGTGVGTHLANQTAWTTLGASHHA<br>SGVASAINTAATAASWLGVGSAASALNVTMLNATLHGLAGWVD<br>VKPAVVSTAIAAFETANAAMRPAPECMENRDEWGVDNAINPSVL<br>WTLTPRIVSLDVEYFGVMWPNNAAVGATYGGVLAALAESLAIPPP<br>VATMG (SEQ ID NO: 23) |
| Rv1789<br>(PPE26) | ATGGACTTCGGCGCCCTGCCCCCCGAGGTGAACAGCGTGAGGA<br>TGTACGCCGGCCCCGGCAGCGCCCCCATGGTGGCCGCCGCCAG<br>CGCCTGGAACGGCCTGGCCGCCGAGCTGAGCAGCGCCGCCACC<br>GGCTACGAGACCGTGATCACCCAGCTGAGCAGCGAGGGCTGGC<br>TGGGCCCCGCCAGCGCCGCCATGGCCGAGGCCGTGGCCCCCTA<br>CGTGGCCTGGATGAGCGCCGCCGCCGCCCAGGCCGAGCAGGCC<br>GCCACCCAGGCCAGGGCCGCCGCCGCCGCCTTCGAGGCCGCC<br>TTCGCCGCCACCGTGCCCCCCCCCCTGATCGCCGCCAACAGGGC<br>CAGCCTGATGCAGCTGATCAGCACCAACGTGTTCGGCCAGAAC<br>ACCAGCGCCATCGCCGCCGCCGAGGCCCAGTACGGCGAGATGT<br>GGGCCCAGGACAGCGCCGCCATGTACGCCTACGCCGGCAGCAG<br>CGCCAGCGCCAGCGCCGTGACCCCCTTCAGCACCCCCCCCCAG<br>ATCGCCAACCCCACCGCCCAGGGCTGA (SEQ ID NO: 24)<br><br>MDFGALPPEVNSVRMYAGPGSAPMVAAASAWNGLAAELSSAAT<br>GYETVITQLSSEGWLGPASAAMAEAVAPYVAWMSAAAAQAEQA<br>ATQARAAAAAFEAAFAATVPPPLIAANRASLMQLISTNVFGQNTS<br>AIAAAAEAQYGEMWAQDSAAMYAYAGSSASASAVTPFSTPPQIAN<br>PTAQG (SEQ ID NO: 25) |

TABLE 3-continued

PPE Antigens

| Construct | nucleotide sequence<br>amino acid sequence |
|---|---|
| Rv1800<br>(PPE28) | ATGCTGCCCAACTTCGCCGTGCTGCCCCCCGAGGTGAACAGCG<br>CCAGGGTGTTCGCCGGCGCCGGCAGCGCCCCCATGCTGGCCGC<br>CGCCGCCGCCTGGGACGACCTGGCCAGCGAGCTGCACTGCGCC<br>GCCATGAGCTTCGGCAGCGTGACCAGCGGCCTGGTGGTGGGCT<br>GGTGGCAGGGCAGCGCCAGCGCCGCCATGGTGGACGCCGCCGC<br>CAGCTACATCGGCTGGCTGAGCACCAGCGCCGCCCACGCCGAG<br>GGCGCCGCCGGCCTGGCCAGGGCCGCCGTGAGCGTGTTCGAG<br>GAGGCCCTGGCCGCCACCGTGCACCCCGCCATGGTGGCCGCCA<br>ACAGGGCCCAGGTGGCCAGCCTGGTGGCCAGCAACCTGTTCGG<br>CCAGAACGCCCCCGCCATCGCCGCCCTGGAGAGCCTGTACGAG<br>TGCATGTGGGCCCAGGACGCCGCCGCCATGGCCGGCTACTACG<br>TGGGCGCCAGCGCCGTGGCCACCCAGCTGGCCAGCTGGCTGCA<br>GAGGCTGCAGAGCATCCCCGGCGCCTGA (SEQ ID NO: 26)<br><br>MLPNFAVLPPEVNSARVFAGAGSAPMLAAAAAWDDLASELHCA<br>AMSFGSVTSGLVVGWWQGSASAAMVDAAASYIGWLSTSAAHAE<br>GAAGLARAAVSVFEEALAATVHPAMVAANRAQVASLVASNLFG<br>QNAPAIAALESLYECMWAQDAAAMAGYYVGASAVATQLASWL<br>QRLQSIPGA (SEQ ID NO: 27) |
| Rv1039c<br>(PPE15) | ATGGACTTCGGCGCCCTGCCCCCCGAGATCAACAGCGCCAGGA<br>TGTACGCCGGCGCCGGCGCCGGCCCCATGATGGCCGCCGGCGC<br>CGCCTGGAACGGCCTGGCCGCCGAGCTGGGCACCACCGCCGCC<br>AGCTACGAGAGCGTGATCACCAGGCTGACCACCGAGAGCTGGA<br>TGGGCCCCGCCAGCATGGCCATGGTGGCCGCCGCCCAGCCCTA<br>CCTGGCCTGGCTGACCTACACCGCCGAGGCCGCCGCCCACGCC<br>GGCAGCCAGGCCATGGCCAGCGCCGCCGCCTACGAGGCCGCC<br>TACGCCATGACCGTGCCCCCCGAGGTGGTGGCCGCCAACAGGG<br>CCCTGCTGGCCGCCCTGGTGGCCACCAACGTGCTGGGCATCAA<br>CACCCCCGCCATCATGGCCACCGAGGCCCTGTACGCCGAGATG<br>TGGGCCCAGGACGCCCTGGCCATGTACGGCTACGCCGCCGCCA<br>GCGGCGCCGCCGGCATGCTGCAGCCCCTGAGCCCCCCCAGCCA<br>GACCACCAACCCCGGCGGCCTGGCCTGA (SEQ ID NO: 28)<br><br>MDFGALPPEINSARMYAGAGAGPMMAAGAAWNGLAAELGTTAA<br>SYESVITRLTTESWMGPASMAMVAAAQPYLAWLTYTAEAAAHA<br>GSQAMASAAAYEAAYAMTVPPEVVAANRALLAALVATNVLGIN<br>TPAIMATEALYAEMWAQDALAMYGYAAASGAAGMLQPLSPPSQ<br>TTNPGGLA (SEQ ID NO: 29) |

In some embodiments, a composition comprises at least two of the PPE antigens. In some embodiments, the composition comprises at least three of the PPE antigens. In some embodiments, the composition comprises at least four of the PPE antigens. In some embodiments, the composition comprises at least five of the PPE antigens. In some embodiments, the composition comprises all six PPE antigens. In some embodiments, the composition comprises from at least two to six of the PPE antigens. In some embodiments, the composition comprises from at least three to six of the PPE antigens. In some embodiments, the composition comprises from at least four to six of the PPE antigens. In some embodiments, the composition comprises at least five or six of the PPE antigens. In some embodiments, the composition further comprises a pharmaceutically acceptable carrier.

In some embodiments, the fusion protein comprises at least two of the PPE antigens. In some embodiments, the fusion protein comprises at least three of the PPE antigens. In some embodiments, the fusion protein comprises at least four of the PPE antigens. In some embodiments, the fusion protein comprises at least five of the PPE antigens. In some embodiments, the fusion protein comprises all six PPE antigens. In some embodiments, the fusion protein comprises from at least two to six of the PPE antigens. In some embodiments, the fusion protein comprises from at least three to six of the PPE antigens. In some embodiments, the fusion protein comprises from at least four to six of the PPE antigens. In some embodiments, the fusion protein comprises at least five or six of the PPE antigens.

In some embodiments, the fusion protein comprises Rv3873, Rv1387, and Rv3892c. In some embodiments, the fusion protein comprises Rv1789, Rv1800, and Rv1039c.

In any of the embodiments of fusion proteins set forth herein, the individual PPE antigens can be present in any order. For example, for a fusion protein comprising Rv1789, Rv1800, and Rv1039c antigens, the first (or N-terminal) antigen may be Rv1789, Rv1800, or Rv1039c; the second antigen may be Rv1789, Rv1800, or Rv1039c (whichever one is not the first PPE antigen); and the third antigen may be Rv1789, Rv1800, and Rv1039c (whichever one is not the first or second PPE antigen). Likewise for every fusion protein disclosed herein.

Individual PPE antigens may be linked together in a C-terminus to N-terminus or N-terminus to C-terminus manner without any linker. Alternately, a linker may be present between any two PPE antigens within any of the fusion proteins disclosed herein. In some embodiments, the linker is a segment of DNA or RNA optionally containing one or more restrictions sites, wherein the linker is inserted between nucleic acid molecules encoding two PE antigens of any of the fusion proteins disclosed herein.

In some embodiments, the fusion protein comprises Rv3873-Rv1387-Rv3892c (Construct B; see Table 4). The nucleotide sequence is SEQ ID NO:30, and the corresponding amino acid sequence is SEQ ID NO:31 (including a C-terminal HA tag (YPYDVPDYA; SEQ ID NO:17) added).

In some embodiments, the fusion protein comprises Rv1789-Rv1800-Rv1039c (Construct C; see Table 4). The nucleotide sequence is SEQ ID NO:32, and the corresponding amino acid sequence is SEQ ID NO:33 (including a C-terminal HA tag (YPYDVPDYA; SEQ ID NO:17) added).

TABLE 4

PPE Antigen Cassette

| Construct | nucleotide sequence amino acid sequence |
|---|---|
| B | ATGCTGTGGCACGCCATGCCCCCCG AGCTGAACACCGCCAGGCTGATGGC CGGCGCCGGCCCCGCCCCCATGCTG GCCGCCGCCGCCGGCTGGCAGACCC TGAGCGCCGCCCTGGACGCCCAGGC CGTGGAGCTGACCGCCAGGCTGAAC AGCCTGGGCGAGGCCTGGACCGGCG GCGGCAGCGACAAGGCCCTGGCCGC CGCCACCCCCATGGTGGTGTGGCTG CAGACCGCCAGCACCCAGGCCAAGA CCAGGGCCATGCAGGCCACCCCCCA GGCCGCCGCCTACACCCAGGCCATG GCCACCACCCCCAGCCTGCCCGAGA TCGCCGCCAACCACATCACCCAGGC CGTGCTGACCGCCACCAACTTCTTC GGCATCAACACCATCCCCATCGCCC TGACCGAGATGGACTACTTCATCAG GATGTGGAACCAGGCCGCCCTGGCC ATGGAGGTGTACCAGGCCGAGACCG CCGTGAACACCCTGTTCGAGAAGCT GGAGCCCATGGCCAGCATCCTGGAC CCCGGCGCCAGCCAGATGACCGAGC CCTGGATCGCCTTCCCCCCCGAGGT GCACAGCGCCATGCTGAACTACGGC GCCGGCGTGGGCCCCATGCTGATCA GCGCCACCCAGAACGGCGAGCTGAG CGCCCAGTACGCCGAGGCCGCCAGC GAGGTGGAGGAGCTGCTGGGCGTGG TGGCCAGCGAGGGCTGGCAGGGCCA GGCCGCCGAGGCCTTCGTGGCCGCC TACATGCCCTTCCTGGCCTGGCTGA TCCAGGCCAGCGCCGACTGCGTGGA GATGGCCGCCCAGCAGCACGTGGTG ATCGAGGCCTACACCGCCGCCGTGG AGCTGATGCCCACCCAGGTGGAGCT GGCCGCCAACCAGATCAAGCTGGCC GTGCTGGTGGCCACCAACTTCTTCG GCATCAACACCATCCCCATCGCCAT CAACGAGGCCGAGTACGTGGAGATG TGGGTGAGGGCCGCCACCACCATGG CCACCTACAGCACCGTGAGCAGGAG CGCCCTGAGCGCCATGCCCCACACC AGCCCCCCCCCCCTGATCCTGAAGA GCGACATGCCCGACCCCGGCTGGGC CGCCAGGACCCCCGAGGCCAACGAC CTGCTGCTGACCGCCGGCACCGGCG TGGGCACCCACCTGGCCAACCAGAC CGCCTGGACCACCCTGGGCGCCAGC CACCACGCCAGCGGCGTGGCCAGCG CCATCAACACCGCCGCCACCGCCGC CAGCTGGCTGGGCGTGGGCAGCGCC GCCAGCGCCCTGAACGTGACCATGC TGAACGCCACCCTGCACGGCCTGGC CGGCTGGGTGGACGTGAAGCCCGCC GTGGTGAGCACCGCCATCGCCGCCT TCGAGACCGCCAACGCCGCCATGAG GCCCGCCCCCGAGTGCATGGAGAAC AGGGACGAGTGGGGCGTGGACAACG CCATCAACCCCAGCGTGCTGTGGAC CCTGACCCCCAGGATCGTGAGCCTG GACGTGGAGTACTTCGGCGTGATGT GGCCCAACAACGCCGCCGTGGGCGC CACCTACGGCGGCGTGCTGGCCGCC CTGGCCGAGAGCCTGGCCATCCCCC CCCCCGTGGCCACCATGGGCTACCC |

TABLE 4-continued

PPE Antigen Cassette

| Construct | nucleotide sequence amino acid sequence |
|---|---|
| | CTACGACGTGCCCGACTACGCCTGA (SEQ ID NO: 30) |
| | MLWHAMPPELNTARLMAGAGPAPML AAAAGWQTLSAALDAQAVELTARLN SLGEAWTGGGSDKALAAATPMVVWL QTASTQAKTRAMQATAQAAAYTQAM ATTPSLPEIAANHITQAVLTATNFF GINTIPIALTEMDYFIRMWNQAALA MEVYQAETAVNTLFEKLEPMASILD PGASQMTEPWIAFPPEVHSAMLNYG AGVGPMLISATQNGELSAQYAEAAS EVEELLGVVASEGWQGQAAEAFVAA YMPFLAWLIQASADCVEMAAQQHVV IEAYTAAVELMPTQVELAANQIKLA VLVATNFFGINTIPIAINEAEYVEM WVRAATTMATYSTVSRSALSAMPHT SPPPLILKSDMPDPGWAARTPEAND LLLTAGTGVGTHLANQTAWTTLGAS HHASGVASAINTAATAASWLGVGSA ASALNVTMLNATLHGLAGWVDVKPA VVSTAIAAFETANAAMRPAPECMEN RDEWGVDNAINPSVLWTLTPRIVSL DVEYFGVMWPNNAAVGATYGGVLAA LAESLAIPPPVATMGYPYDVPDYA (SEQ ID NO: 31) |
| C | ATGGACTTCGGCGCCCTGCCCCCCG AGGTGAACAGCGTGAGGATGTACGC CGGCCCCGGCAGCGCCCCCATGGTG GCCGCCGCCAGCGCCTGGAACGGCC TGGCCGCCGAGCTGAGCAGCGCCGC CACCGGCTACGACCGTGATCACC CAGCTGAGCAGCGAGGGCTGGCTGG GCCCCGCCAGCGCCGCCATGGCCGA GGCCGTGGCCCCCTACGTGGCCTGG ATGAGCGCCGCCGCGCCCAGGCCG AGCAGGCCGCCACCCAGGCCAGGGC CGCCGCCGCCGCCTTCGAGGCCGCC TTCGCCGCCACCGTGCCCCCCCCCC TGATCGCCGCCAACAGGGCCAGCCT GATGCAGCTGATCAGCACCAACGTG TTCGGCCAGAACACCAGCGCCATCG CCGCCGCCGAGGCCCAGTACGGCGA GATGTGGGCCCAGGACAGCGCCGCC ATGTACGCCTACGCCGGCAGCAGCG CCAGCGCCAGCGCCGTGACCCCCTT CAGCACCCCCCCCCAGATCGCCAAC CCCACCGCCCAGGGCATGCTGCCCA ACTTCGCCGTGCTGCCCCCCGAGGT GAACAGCGCCAGGGTGTTCGCCGGC GCCGGCAGCGCCCCCATGCTGGCCG CCGCCGCCTGGGACGACCTGGC CAGCGAGCTGCACTGCGCCGCCATG AGCTTCGGCAGCGTGACCAGCGGCC TGGTGGTGGGCTGGTGGCAGGGCAG CGCCAGCGCCGCCATGGTGGACGCC GCCGCCAGCTACATCGGCTGGCTGA GCACCAGCGCCGCCCACGCCGAGGG CGCCGCCGGCCTGGCCAGGGCCGCC GTGAGCGTGTTCGAGGAGGCCCTGG CCGCCACCGTGCACCCCGCCATGGT GGCCGCCAACAGGGCCCAGGTGGCC AGCCTGGTGGCCAGCAACCTGTTCG GCCAGAACGCCCCGCCATCGCCGC CCTGGGAGAGCCTGTACGAGTGCATG TGGGCCCAGGACGCCGCCGCCATGG CCGGCTACTACGTGGGCGCCAGCGC CGTGGCCACCCAGCTGGCCAGCTGG CTGCAGAGGCTGCAGAGCATCCCCG GCGCCATGGACTTCGGCGCCCTGCC CCCCGAGATCAACAGCGCCAGGATG TACGCCGGCGCCGGCGCCGCCCCA TGATGGCCGCCGGCGCCGCCCTGGAA CGGCCTGGCCGCCGAGCTGGGCACC |

TABLE 4-continued

PPE Antigen Cassette

| Construct | nucleotide sequence amino acid sequence |
|---|---|
| | ACCGCCGCCAGCTACGAGAGCGTGA<br>TCACCAGGCTGACCACCGAGAGCTG<br>GATGGGCCCCGCCAGCATGGCCATG<br>GTGGCCGCCGCCCAGCCCTACCTGG<br>CCTGGCTGACCTACACCGCCGAGGC<br>CGCCGCCCACGCCGGCAGCCAGGCC<br>ATGGCCAGCGCCGCCGCCTACGAGG<br>CCGCCTACGCCATGACCGTGCCCCC<br>CGAGGTGGTGGCCGCCAACAGGGCC<br>CTGCTGGCCGCCCTGGTGGCCACCA<br>ACGTGCTGGGCATCAACACCCCCGC<br>CATCATGGCCACCGAGGCCCTGTAC<br>GCCGAGATGTGGGCCCAGGACGCCC<br>TGGCCATGTACGGCTACGCCGCCGC<br>CAGCGGCGCCGCCGGCATGCTGCAG<br>CCCCTGAGCCCCCCCAGCCAGACCA<br>CCAACCCCGGCGGCCTGGCCTACCC<br>CTACGACGTGCCCGACTACGCCTGA<br>(SEQ ID NO: 32)<br><br>MDFGALPPEVNSVRMYAGPGSAPMV<br>AAASAWNGLAAELSSAATGYETVIT<br>QLSSEGWLGPASAAMAEAVAPYVAW<br>MSAAAAQAEQAATQARAAAAAFEAA<br>FAATVPPPLIAANRASLMQLISTNV<br>FGQNTSAIAAAEAQYGEMWAQDSAA<br>MYAYAGSSASASAVTPFSTPPQIAN<br>PTAQGMLPNFAVIPPEVNSARVFAG<br>AGSAPMLAAAAAWDDLASELHCAAM<br>SFGSVTSGLVVGWWQGSASAAMVDA<br>AASYIGWLSTSAAHAEGAAGLARAA<br>VSVFEEALAATVHPAMVAANRAQVA<br>SLVASNLFGQNAPAIAALESLYECM<br>WAQDAAAMAGYYVGASAVATQLASW<br>LQRLQSIPGAMDFGALPPEINSARM<br>YAGAGAGPMMAAGAAWNGLAAELGT<br>TAASYESVITRLTTESWMGPASMAM<br>VAAAQPYLAWLTYTAEAAAHAGSQA<br>MASAAAYEAAYAMTVPPEVVAANRA<br>LLAALVATNVLGINTPAIMATEALY<br>AEMWAQDALAMYGYAAASGAAGMLQ<br>PLSPPSQTTNPGGLAYPYDVPDYA<br>(SEQ ID NO: 33) |

In some embodiments, the Mtb antigen is an ESX antigen. In some embodiments, the ESX antigen is Rv3017c (also known as esxQ), Rv3020c (also known as esxS), Rv3019c (also known as esxR) Rv3891c (also known as esxD), Rv2346c (also known as esxO), Rv3445c (also known as esxU), Rv3619c (also known as esxV), Rv3875 (also known as esxA and ESAT6), or Rv3874 (also known as esxB and CFP10).

A nucleotide sequence encoding Rv3017c is shown in Table 5 as SEQ ID NO:34, and an amino acid sequence of Rv3017c is shown in Table 5 as SEQ ID NO:35.

A nucleotide sequence encoding Rv3020c is shown in Table 5 as SEQ ID NO:36, and an amino acid sequence of Rv3020c is shown in Table 5 as SEQ ID NO:37.

A nucleotide sequence encoding Rv3019c is shown in Table 5 as SEQ ID NO:38, and an amino acid sequence of Rv3019c is shown in Table 5 as SEQ ID NO:39.

A nucleotide sequence encoding Rv3891c is shown in Table 5 as SEQ ID NO:40, and an amino acid sequence of Rv3891c is shown in Table 5 as SEQ ID NO:41.

A nucleotide sequence encoding Rv2346c is shown in Table 5 as SEQ ID NO:42, and an amino acid sequence of Rv2346c is shown in Table 5 as SEQ ID NO:43.

A nucleotide sequence encoding Rv3445c is shown in Table 5 as SEQ ID NO:44, and an amino acid sequence of Rv3445c is shown in Table 5 as SEQ ID NO:45.

A nucleotide sequence encoding Rv3619c is shown in Table 5 as SEQ ID NO:46, and an amino acid sequence of Rv3619c is shown in Table 5 as SEQ ID NO:47.

A nucleotide sequence encoding Rv3875 is shown in Table 5 as SEQ ID NO:48, and an amino acid sequence of Rv3875 is shown in Table 5 as SEQ ID NO:49.

A nucleotide sequence encoding Rv3874 is shown in Table 5 as SEQ ID NO:50, and an amino acid sequence of Rv3874 is shown in Table 5 as SEQ ID NO:51.

TABLE 5

ESX Antigens

| Construct | nucleotide sequence aminoacidsequence |
|---|---|
| Rv 3017c (esxQ) | GTGAGCCAGAGCATGTACAGCTACC<br>CCGCCATGACCGCCAACGTGGGCGA<br>CATGGCCGGCTACACCGGCACCACC<br>CAGAGCCTGGGCGCCGACATCGCCA<br>GCGAGAGGACCGCCCCCAGCAGGGC<br>CTGCCAGGGCGACCTGGGCATGAGC<br>CACCAGGACTGGCAGGCCCAGTGGA<br>ACCAGGCCATGGAGGCCCTGGCCAG<br>GGCCTACAGGAGGTGCAGGAGGGCC<br>CTGAGGCAGATCGGCGTGCTGGAGA<br>GGCCCGTGGGCGACAGCAGCGACTG<br>CGGCACCATCAGGGTGGGCAGCTTC<br>AGGGGCAGGTGGCTGGACCCCAGGC<br>ACGCCGGCCCCGCCACCGCCGCCGA<br>CGCCGGCGACTGA<br>(SEQ ID NO: 34)<br><br>VSQSMYSYPAMTANVGDMAGYTGTT<br>QSLGADIASERTAPSRACQGDLGMS<br>HQDWQAQWNQAMEALARAYRRCRRA<br>LRQIGVLERPVGDSSDCGTIRVGSF<br>RGRWLDPRHAGPATAADAGD<br>(SEQ ID NO: 35) |
| Rv3020c (esxS) | ATGAGCCTGCTGGACGCCCACATCC<br>CCCAGCTGATCGCCAGCCACACCGC<br>CTTCGCCGCCAAGGCCGGCCTGATG<br>AGGCACACCATCGGCCAGGCCGAGC<br>AGCAGGCCATGAGCGCCCAGGCCTT<br>CCACCAGGGCGAGAGCGCCGCCGCC<br>TTCCAGGGCGCCCACGCCAGGTTCG<br>TGGCCGCCGCCGCCAAGGTGAACAC<br>CCTGCTGGACATCGCCCAGGCCAAC<br>CTGGGCGAGGCCGCCGGCACCTACG<br>TGGCCGCCGACGCCGCCGCCGCCAG<br>CAGCTACACCGGCTTCTGA<br>(SEQ ID NO: 36)<br><br>MSLLDAHIPQLIASHTAFAAKAGLM<br>RHTIGQAEQQAMSAQAFHQGESAAA<br>FQGAHARFVAAAAKVNTLLDIAQAN<br>LGEAAGTYVAADAAAASSYTGF<br>(SEQ ID NO: 37) |
| Rv3019c (esxR) | ATGAGCCAGATCATGTACAACTACC<br>CCGCCATGATGGCCCACGCCGGCGA<br>CATGGCCGGCTACGCCGGCACCCTG<br>CAGAGCCTGGGCGCCGACATCGCCA<br>GCGAGCAGGCCGTGCTGAGCAGCGC<br>CTGGCAGGGCGACACCGGCATCACC<br>TACCAGGGCTGGCAGACCCAGTGGA<br>ACCAGGCCCTGGAGGACCTGGTGAG<br>GGCCTACCAGAGCATGAGCGGCACC<br>CACGAGAGCAACACCATGGCCATGC<br>TGGCCAGGGACGGCGCCGAGGCCGC<br>CAAGTGGGGCGGCTGA<br>(SEQ ID NO: 38)<br><br>MSQIMYNYPAMMAHAGDMAGYAGTL<br>QSLGADIASEQAVLSSAWQGDTGIT<br>YQGWQTQWNQALEDLVRAYQSMSGT<br>HESNTMAMLARDGAEAAKWGG<br>(SEQ ID NO: 39) |

TABLE 5-continued

ESX Antigens

| Construct | nucleotide sequence aminoacidsequence |
|---|---|
| Rv3891c (esxD) | GTGGCCGACACCATCCAGGTGACCC CCCAGATGCTGAGGAGCACCGCCAA CGACATCCAGGCCAACATGGAGCAG GCCATGGGCATCGCCAAGGGCTACC TGGCCAACCAGGAGAACGTGATGAA CCCCGCCACCTGGAGCGGCACCGGC GTGGTGGCCAGCCACATGACCGCCA CCGAGATCACCAACGAGCTGAACAA GGTGCTGACCGGCGGCACCAGGCTG GCCGAGGGCCTGGTGCAGGCCGCCG CCCTGATGGAGGGCCACGAGGCCGA CAGCCAGACCGCCTTCCAGGCCCTG TTCGGCGCCAGCCACGGCAGCTGA (SEQ ID NO: 40)<br><br>VADTIQVTPQMLRSTANDIQANMEQ AMGIAKGYLANQENVMNPATWSGTG VVASHMTATEITNELNKVLTGGTRL AEGLVQAAALMEGHEADSQTAFQAL FGASHGS (SEQ ID NO: 41) |
| Rv2346c (esxO) | ATGACCATCAACTACCAGTTCGGCG ACGTGGACGCCCACGGCGCCATGAT CAGGGCCCAGGCCGGCCTGCTGGAG GCCGAGCACCAGGCCATCGTGAGGG ACGTGCTGGCCGCCGGCGACTTCTG GGGCGGCGCCGGCAGCGTGGCCTGC CAGGAGTTCATCACCCAGCTGGGCA GGAACTTCCAGGTGATCTACGAGCA GGCCAACGCCCACGGCCAGAAGGTG CAGGCCGCCGGCAACAACATGGCCC AGACCGACAGCGCCGTGGGCAGCAG CTGGGCCTGA (SEQ ID NO: 42)<br><br>MTINYQFGDVDAHGAMIRAQAGLLE AEHQAIVRDVLAAGDFWGGAGSVAC QEFITQLGRNFQVIYEQANAHGQKV QAAGNNMAQTDSAVGSSWA (SEQ ID NO: 43) |
| Rv3445c (esxU) | GTGAGCACCCCCAACACCCTGAACG CCGACTTCGACCTGATGAGGAGCGT GGCCGGCATCACCGACGCCAGGAAC GAGGAGATCAGGGCCATGCTGCAGG CCTTCATCGGCAGGATGAGCGGCGT GCCCCCCAGCGTGTGGGGCGGCCTG GCCGCCGCCAGGTTCCAGGACGTGG TGGACAGGTGGAACGCCGAGAGCAC CAGGCTGTACCACGTGCTGCACGCC ATCGCCGACACCATCAGGCACAACG AGGCCGCCCTGAGGGAGGCCGGCCA GATCCACGCCAGGCACATCGCCGCC GCCGGCGGCGACCTGTGA (SEQ ID NO: 44)<br><br>VSTPNTLNADFDLMRSVAGITDARN EEIRAMLQAFIGRMSGVPPSVWGGL AAARFQDVVDRWNAESTRLYHVLHA IADTIRHNEAALREAGQIHARHIAA AGGDL (SEQ ID NO: 45) |
| Rv3619c (esx V) | ATGACCATCAACTACCAGTTCGGCG ACGTGGACGCCCACGGCGCCATGAT CAGGGCCCAGGCCGGCAGCCTGGAG GCCGAGCACCAGGCCATCATCAGCG ACGTGCTGACCGCCAGCGACTTCTG GGGCGGCGCCGGCAGCGCCGCCTGC CAGGGCTTCATCACCCAGCTGGGCA GGAACTTCCAGGTGATCTACGAGCA GGCCAACGCCCACGGCCAGAAGGTG CAGGCCGCCGGCAACAACATGGCCC AGACCGACAGCGCCGTGGGCAGCAG CTGGGCCTGA (SEQ ID NO: 46)<br><br>MTINYQFGDVDAHGAMIRAQAGSLE AEHQAIISDVLTASDFWGGAGSAAC QGFITQLGRNFQVIYEQANAHGQKV QAAGNNMAQTDSAVGSSWA (SEQ ID NO: 47) |
| Rv3875 (esxA, ESAT6) | ATGACCGAGCAGCAGTGGAACTTCG CCGGCATCGAGGCCGCCGCCAGCGC CATCCAGGGCAACGTGACCAGCATC CACAGCCTGCTGGACGAGGGCAAGC AGAGCCTGACCAAGCTGGCCGCCGC CTGGGGCGGCAGCGGCAGCGAGGCC TACCAGGGCGTGCAGCAGAAGTGGG ACGCCACCGCCACCGAGCTGAACAA CGCCCTGCAGAACCTGGCCAGGACC ATCAGCGAGGCCGGCCAGGCCATGG CCAGCACCGAGGGCAACGTGACCGG CATGTTCGCCTGA (SEQ ID NO: 48)<br><br>MTEQQWNFAGIEAAASAIQGNVTSI HSLLDEGKQSLTKLAAAWGGSGSEA YQGVQQKWDATATELNNALQNLART ISEAGQAMASTEGNVTGMFA (SEQ ID NO: 49) |
| Rv3874 (esxB, CFP10) | ATGGCCGAGATGAAGACCGACGCCG CCACCCTGGCCCAGGAGGCCGGCAA CTTCGAGAGGATCAGCGGCGACCTG AAGACCCAGATCGACCAGGTGGAGA GCACCGCCGGCAGCCTGCAGGGCCA GTGGAGGGGCGCCGCCGGCACCGCC GCCCAGGCCGCCGTGGTGAGGTTCC AGGAGGCCGCCAACAAGCAGAAGCA GGAGCTGGACGAGATCAGCACCAAC ATCAGGCAGGCCGGCGTGCAGTACA GCAGGGCCGACGAGGAGCAGCAGCA GGCCCTGAGCAGCCAGATGGGCTTC TGA (SEQ ID NO: 50)<br><br>MAEMKTDAATLAQEAGNFERISGDL KTQIDQVESTAGSLQGQWRGAAGTA AQAAVVRFQEAANKQKQELDEISTN IRQAGVQYSRADEEQQQALSSQMGF (SEQ ID NO: 51) |

In some embodiments, a composition comprises at least two of the ESX antigens. In some embodiments, the composition comprises at least three of the ESX antigens. In some embodiments, the composition comprises at least four of the ESX antigens. In some embodiments, the composition comprises at least five of the ESX antigens. In some embodiments, the composition comprises at least six of the ESX antigens. In some embodiments, the composition comprises at least seven of the ESX antigens. In some embodiments, the composition comprises at least eight of the ESX antigens. In some embodiments, the composition comprises all nine ESX antigens. In some embodiments, the composition comprises from at least two to nine of the ESX antigens. In some embodiments, the composition comprises from at least three to nine of the ESX antigens. In some embodiments, the composition comprises from at least four to nine of the ESX antigens. In some embodiments, the composition comprises at least five to nine of the ESX antigens. In some embodiments, the composition comprises at least six to nine of the ESX antigens. In some embodiments, the composition comprises at least seven to nine of the ESX antigens. In some embodiments, the composition comprises eight or nine of the ESX antigens. In some embodiments, the composition further comprises a pharmaceutically acceptable carrier.

In some embodiments, the fusion protein comprises at least two of the ESX antigens. In some embodiments, the fusion protein comprises at least three of the ESX antigens. In some embodiments, the fusion protein comprises at least four of the ESX antigens. In some embodiments, the fusion protein comprises at least five of the ESX antigens. In some embodiments, the fusion protein comprises at least six of the ESX antigens. In some embodiments, the fusion protein comprises at least seven of the ESX antigens. In some embodiments, the fusion protein comprises at least eight of the ESX antigens. In some embodiments, the fusion protein comprises all nine ESX antigens. In some embodiments, the fusion protein comprises from at least two to nine of the ESX antigens. In some embodiments, the fusion protein comprises from at least three to nine of the ESX antigens. In some embodiments, the fusion protein comprises from at least four to nine of the ESX antigens. In some embodiments, the fusion protein comprises at least five to nine of the ESX antigens. In some embodiments, the fusion protein comprises at least six to nine of the ESX antigens. In some embodiments, the fusion protein comprises at least seven to nine of the ESX antigens. In some embodiments, the fusion protein comprises eight or nine of the ESX antigens.

In some embodiments, the fusion protein comprises Rv3017c, Rv3020c, Rv3019c, Rv3891c, Rv2346c, and Rv3445c. In some embodiments, the fusion protein comprises Rv3619c, Rv3875, and Rv3874.

In any of the embodiments of fusion proteins set forth herein, the individual ESX antigens can be present in any order. For example, for a fusion protein comprising Rv3619c, Rv3875, and Rv3874 antigens, the first (or N-terminal) antigen may be Rv3619c, Rv3875, or Rv3874; the second antigen may be Rv3619c, Rv3875, or Rv3874 (whichever one is not the first ESX antigen); and the third antigen may be Rv3619c, Rv3875, or Rv3874 (whichever one is not the first or second ESX antigen). Likewise for every fusion protein disclosed herein.

Individual ESX antigens may be linked together in a C-terminus to N-terminus or N-terminus to C-terminus manner without any linker. Alternately, a linker may be present between any two ESX antigens within any of the fusion proteins disclosed herein. In some embodiments, the linker is a segment of DNA or RNA optionally containing one or more restrictions sites, wherein the linker is inserted between nucleic acid molecules encoding two ESX antigens of any of the fusion proteins disclosed herein.

In some embodiments, the fusion protein comprises Rv3017c-Rv3020c-Rv3019c-Rv3891c-Rv2346c-Rv3445c (Construct D; see Table 6). The nucleotide sequence is SEQ ID NO:52, and the corresponding amino acid sequence is SEQ ID NO:53 (including a C-terminal HA tag (YPYDVPDYA; SEQ ID NO:17) added).

In some embodiments, the fusion protein comprises Rv3619c-Rv3875-Rv3874 (Construct E; see Table 6). The nucleotide sequence is SEQ ID NO:54, and the corresponding amino acid sequence is SEQ ID NO:55 (including a C-terminal HA tag (YPYDVPDYA; SEQ ID NO:17) added).

TABLE 6

ESX Antigen Cassette

| Construct | nucleotide sequence amino acid sequence |
|---|---|
| D | GTGAGCCAGAGCATGTACAGCTACC
CCGCCATGACCGCCAACGTGGGCGA
CATGGCCGGCTACACCGGCACCACC
CAGAGCCTGGGCGCCGACATCGCCA
GCGAGAGGACCGCCCCCAGCAGGGC
CTGCCAGGGCGACCTGGGCATGAGC
CACCAGGACTGGCAGGCCCAGTGGA
ACCAGGCCATGGAGGCCCTGGCCAG
GGCCTACAGGAGGTGCAGGAGGGCC
CTGAGGCAGATCGGCGTGCTGGAGA
GGCCCGTGGGCGACAGCAGCGACTG
CGGCACCATCAGGGTGGGCAGCTTC
AGGGGCAGGTGGCTGGACCCCAGGC
ACGCCGGCCCCGCCACCGCCGCCGA
CGCCGGCGACATGAGCCTGCTGGAC
GCCCACATCCCCCAGCTGATCGCCA
GCCACACCGCCTTCGCCGCCAAGGC
CGGCCTGATGAGGCACACCATCGGC
CAGGCCGAGCAGCAGGCCATGAGCG
CCCAGGCCTTCCACCAGGGCGAGAG
CGCCGCCGCCTTCCAGGGCGCCCAC
GCCAGGTTCGTGGCCGCCGCCGCCA
AGGTGAACACCCTGCTGGACATCGC
CCAGGCCAACCTGGGCGAGGCCGCC
GGCACCTACGTGGCCGCCGACGCCG
CCGCCGCCAGCAGCTACACCGGCTT
CATGAGCCAGATCATGTACAACTAC
CCCGCCATGATGGCCCACGCCGGCG
ACATGGCCGGCTACGCCGGCACCCT
GCAGAGCCTGGGCGCCGACATCGCC
AGCGAGCAGGCCGTGCTGAGCAGCG
CCTGGCAGGGCGACACCGGCATCAC
CTACCAGGGCTGGCAGACCCAGTGG
AACCAGGCCCTGGAGGACCTGGTGA
GGGCCTACCAGAGCATGAGCGGCAC
CCACGAGAGCAACACCATGGCCATG
CTGGCCAGGGACGGCGCCGAGGCCG
CCAAGTGGGGCGGCGTGGCCGACAC
CATCCAGGTGACCCCCCAGATGCTG
AGGAGCACCGCCAACGACATCCAGG
CCAACATGGAGCAGGCCATGGGCAT
CGCCAAGGGCTACCTGGCCAACCAG
GAGAACGTGATGAACCCCGCCACCT
GGAGCGGCACCGGCGTGGTGGCCAG
CCACATGACCGCCACCGAGATCACC
AACGAGCTGAACAAGGTGCTGACCG
GCGGCACCAGGCTGGCCGAGGGCCT
GGTGCAGGCCGCCGCCCTGATGGAG
GGCCACGAGGCCGACAGCCAGACCG
CCTTCCAGGCCCTGTTCGGCGCCAG
CCACGGCAGCATGACCATCAACTAC
CAGTTCGGCGACGTGGACGCCCACG
GCGCCATGATCAGGGCCCAGGCCGG
CCTGCTGGAGGCCGAGCACCAGGCC
ATCGTGAGGGACGTGCTGGCCGCCG
GCGACTTCTGGGGCGGCGCCGGCAG
CGTGGCCTGCCAGGAGTTCATCACC
CAGCTGGGCAGGAACTTCCAGGTGA
TCTACGAGCAGGCCAACGCCCACGG
CCAGAAGGTGCAGGCCGCCGGCAAC
AACATGGCCCAGACCGACAGCGCCG
TGGGCAGCAGCTGGGCCGTGAGCAC
CCCCAACACCCTGAACGCCGACTTC
GACCTGATGAGGAGCGTGGCCGGCA
TCACCGACGCCAGGAACGAGGAGAT
CAGGGCCATGCTGCAGGCCTTCATC
GGCAGGATGAGCGGCGTGCCCCCCA
GCGTGTGGGCGGCCTGGCCGCCGC
CAGGTTCCAGGACGTGGTGGACAGG
TGGAACGCCGAGAGCACCAGGCTGT
ACCACGTGCTGCACGCCATCGCCGA
CACCATCAGGCACAACGAGGCCGCC
CTGAGGGAGGCCGGCCAGATCCACG
CCAGGCACATCGCCGCCGCCGGCGG
CGACCTGTACCCCTACGACGTGCCC |

TABLE 6-continued

ESX Antigen Cassette

| Construct | nucleotide sequence amino acid sequence |
|---|---|
| | GACTACGCCTGA<br>(SEQ ID NO: 52)<br><br>VSQSMYSYPAMTANVGDMAGYTGTT<br>QSLGADIASERTAPSRACQGDLGMS<br>HQDWQAQWNQAMEALARAYRRCRRA<br>LRQIGVLERPVGDSSDCGTIRVGSF<br>RGRWLDPRHAGPATAADAGDMSLLD<br>AHIPQLIASHTAFAAKAGLMRHTIG<br>QAEQQAMSAQAFHQGESAAAFQGAH<br>ARFVAAAAKVNTLLDIAQANLGEAA<br>GTYVAADAAAASSYTGFMSQIMYNY<br>PAMMAHAGDMAGYAGTLQSLGADIA<br>SEQAVLSSAWQGDTGITYQGWQTQW<br>NQALEDLVRAYQSMSGTHESNTMAM<br>LARDGAEEAAKWGGVADTIQVTPQML<br>RSTANDIQANMEQAMGIAKGYLANQ<br>ENVMNPATWSGTGVVASHMTATEIT<br>NELNKVLTGGTRLAEGLVQAAALME<br>GHEADSQTAFQALFGASHGSMTINY<br>QFGDVDAHGAMIRAQAGLLEAEHQA<br>IVRDVLAAGDFWGGAGSVACQEFIT<br>QLGRNFQVIYEQANAHGQKVQAAGN<br>NMAQTDSAVGSSWAVSTPNTLNADF<br>DLMRSVAGITDARNEEIRAMLQAFI<br>GRMSGVPPSVWGGLAAARFQDVVDR<br>WNAESTRLYHVLHAIADTIRHNEAA<br>LREAGQIHARHIAAAGGDLYPYDVP<br>DYA<br>(SEQ ID NO: 53) |
| E | ATGACCATCAACTACCAGTTCGGCG<br>ACGTGGACGCCCACGGCGCCATGAT<br>CAGGGCCCAGGCCGGCAGCCTGGAG<br>GCCGAGCACCAGGCCATCATCAGCG<br>ACGTGCTGACCGCCAGCGACTTCTG<br>GGGCGGCGCCGGCAGCGCCGCCTGC<br>CAGGGCTTCATCACCCAGCTGGGCA<br>GGAACTTCCAGGTGATCTACGAGCA<br>GGCCAACGCCCACGGCCAGAAGGTG<br>CAGGCCGCCGGCAACAACATGGCCC<br>AGACCGACAGCGCCGTGGGCAGCAG<br>CTGGGCCATGACCGAGCAGCAGTGG<br>AACTTCGCCGGCATCGAGGCCGCCG<br>CCAGCGCCATCCAGGGCAACGTGAC<br>CAGCATCCACAGCCTGCTGGACGAG<br>GGCAAGCAGAGCCTGACCAAGCTGG<br>CCGCCGCCTGGGGCGGCAGCGGCAG<br>CGAGGCCTACCAGGGCGTGCAGCAG<br>AAGTGGGACGCCACCGCCACCGAGC<br>TGAACAACGCCCTGCAGAACCTGGC<br>CAGGACCATCAGCGAGGCCGGCCAG<br>GCCATGGCCAGCACCGAGGGCAACG<br>TGACCGGCATGTTCGCCATGGCCGA<br>GATGAAGACCGACGCCGCCACCCTG<br>GCCCAGGAGGCCGGCAACTTCGAGA<br>GGATCAGCGGCGACCTGAAGACCCA<br>GATCGACCAGGTGGAGAGCACCGCC<br>GGCAGCCTGCAGGGCCAGTGGAGGG<br>CGCCGCCGGCACCGCCGCCCAGGC<br>CGCCGTGGTGAGGTTCCAGGAGGCC<br>GCCAACAAGCAGAAGCAGGAGCTGG<br>ACGAGATCAGCACCAACATCAGGCA<br>GGCCGGCGTGCAGTACAGCAGGGCC<br>GACGAGGAGCAGCAGCAGGCCCTGA<br>GCAGCCAGATGGGCTTCTACCCCTA<br>CGACGTGCCCGACTACGCCTGA<br>(SEQ ID NO: 54)<br><br>MTINYQFGDVDAHGAMIRAQAGSLE<br>AEHQAIISDVLTASDFWGGAGSAAC<br>QGFITQLGRNFQVIYEQANAHGQKV<br>QAAGNNMAQTDSAVGSSWAMTEQQW<br>NFAGIEAAASAIQGNVTSIHSLLDE<br>GKQSLTKLAAAWGGSGSEAYQGVQQ |

TABLE 6-continued

ESX Antigen Cassette

| Construct | nucleotide sequence amino acid sequence |
|---|---|
| | KWDATATELNNALQNLARTISEAGQ<br>AMASTEGNVTGMFAMAEMKTDAATL<br>AQEAGNFERISGDLKTQIDQVESTA<br>GSLQGQWRGAAGTAAQAAVVRFQEA<br>ANKQKQELDEISTNIRQAGVQYSRA<br>DEEQQQALSSQMGFYPYDVPDYA<br>(SEQ ID NO: 55) |

In some embodiments, the Mtb antigen is a variable antigen. In some embodiments, the variable antigen is Rv2719c, Rv0010c, Rv1872c, Rv0012, Rv0990c, or Rv0995.

A nucleotide sequence encoding Rv2719c is shown in Table 7 as SEQ ID NO:56, and an amino acid sequence of Rv2719c is shown in Table 7 as SEQ ID NO:57.

A nucleotide sequence encoding Rv0010c is shown in Table 7 as SEQ ID NO:58, and an amino acid sequence of Rv0010c is shown in Table 7 as SEQ ID NO:59.

A nucleotide sequence encoding Rv1872c is shown in Table 7 as SEQ ID NO:60, and an amino acid sequence of Rv1872c is shown in Table 7 as SEQ ID NO:61.

A nucleotide sequence encoding Rv0012 is shown inn Table 7 as SEQ ID NO:62, and an amino acid sequence of Rv0012 is shown in Table 7 as SEQ ID NO:63.

A nucleotide sequence encoding Rv0990c is shown in Table 7 as SEQ ID NO:64, and an amino acid sequence of Rv0990c is shown in Table 7 as SEQ ID NO:65.

A nucleotide sequence encoding Rv0995 is shown in Table 7 as SEQ ID NO:66, and an amino acid sequence of Rv0995 is shown in Table 7 as SEQ ID NO:67.

TABLE 7

Variable Antigens

| Construct | Nucleotide sequence amino acid sequence |
|---|---|
| Rv2719c | ATGACCCCCGTGAGGCCCCCCACA<br>CCCCCGACCCCCTGAACCTGAGGGG<br>CCCCCTGGACGGCCCCAGGTGGAGG<br>AGGGCCGAGCCCGCCCAGAGCAGGA<br>GGCCCGGCAGGAGCAGGCCCGGCGG<br>CGCCCCCCTGAGGTACCACAGGACC<br>GGCGTGGGCATGAGCAGGACCGGCC<br>ACGGCAGCAGGCCCGTGCCCCCCGC<br>CACCACCGTGGGCCTGGCCCTGCTG<br>GCCGCCGCCATCACCCTGTGGCTGG<br>GCCTGGTGGCCCAGTTCGGCCAGAT<br>GATCACCGGCGGCAGCGCCGACGGC<br>AGCGCCGACAGCACCGGCAGGGTGC<br>CCGACAGGCTGGCCGTGGTGAGGGT<br>GGAGACCGGCGAGAGCCTGTACGAC<br>GTGGCCGTGAGGGTGGCCCCCAACG<br>CCCCCACCAGGCAGGTGGCCGACAG<br>GATCAGGGAGCTGAACGGCCTGCAG<br>ACCCCCGCCCTGGCCGTGGGCCAGA<br>CCCTGATCGCCCCCGTGGGCTGA<br>(SEQ ID NO: 56)<br><br>MTPVRPPHTPDPLNLRGPLDGPRWR<br>RAEPAQSRRPGRSRPGGAPLRYHRT<br>GVGMSRTGHGSRPVPPATTVGLALL<br>AAAITLWLGLVAQFGQMITGGSADG<br>SADSTGRVPDRLAVVRVETGESLYD<br>VAVRVAPNAPTRQVADRIRELNGLQ<br>TPALAVGOTLIAPVG<br>(SEQ ID NO: 57) |

TABLE 7-continued

Variable Antigens

| Construct | Nucleotide sequence amino acid sequence |
|---|---|
| Rv0010c | ATGCAGCAGACCGCCTGGGCCCCA GGACCAGCGGCATCGCCGGCTGCGG CGCCGGCGGCGTGGTGATGGCCATC GCCAGCGTGACCCTGGTGACCGACA CCCCCGGCAGGGTGCTGACCGGCGT GGCCGCCCTGGGCCTGATCCTGTTC GCCAGCGCCACCTGGAGGGCCAGGC CCAGGCTGGCCATCACCCCCGACGG CCTGGCCATCAGGGGCTGGTTCAGG ACCCAGCTGCTGAGGCACAGCAACA TCAAGATCATCAGGATCGACGAGTT CAGGAGGTACGGCAGGCTGGTGAGG CTGCTGGAGATCGAGACCGTGAGCG GCGGCCTGCTGATCCTGAGCAGGTG GGACCTGGGCACCGACCCCGTGGAG GTGCTGGACGCCCTGACCGCCGCCG GCTACGCCGGCAGGGGCCAGAGGTG A (SEQ ID NO: 58) MQQTAWAPRTSGIAGCGAGGVVMAI ASVTLVTDTPGRVLTGVAALGLILF ASATWRARPRLAITPDGLAIRGWFR TQLLRHSNIKIIRIDEFRRYGRLVR LLEIETVSGGLLILSRWDLGTDPVE VLDALTAAGYAGRGQR (SEQ ID NO: 59) |
| Rv1872c | ATGGCCGTGAACAGGAGGGTGCCCA GGGTGAGGGACCTGGCCCCCCTGCT GCAGTTCAACAGGCCCCAGTTCGAC ACCAGCAAGAGGAGGCTGGGCGCCG CCCTGACCATCCAGGACCTGAGGAG GATCGCCAAGAGGAGGACCCCCAGG GCCGCCTTCGACTACGCCGACGGCG CGCCGAGGACGAGCTGAGCATCGC CAGGGCCAGGCAGGGCTTCAGGGAC ATCGAGTTCCACCCCACCATCCTGA GGGACGTGACCACCGTGTGCGCCGG CTGGAACGTGCTGGGCCAGCCCACC GTGCTGCCCTTCGGCATCGCCCCCA CCGGCTTCACCAGGCTGATGCACAC CGAGGGCGAGATCGCCGGCGCCAGG GCCGCCGCCGCCGCCGGCATCCCCT TCAGCCTGAGCACCCTGGCCACCTG CGCCATCGAGGACCTGGTGATCGCC GTGCCCCAGGGCAGGAAGTGGTTCC AGCTGTACATGTGGAGGGACAGGGA CAGGAGCATGGCCCTGGTGAGGAGG GTGGCCGCCGCCGGCTTCGACACCA TGCTGGTGACCGTGGACGTGCCCGT GGCCGGCGCCAGGCTGAGGGACGTG AGGAACGGCATGAGCATCCCCCCCG CCCTGACCCTGAGGACCGTGCTGGA CGCCATGGGCCACCCCAGGTGGTGG TTCGACCTGCTGACCACCGAGCCCC TGGCCTTCGCCAGCCTGGACAGGTG GCCCGGCACCGTGGGCGAGTACCTG AACACCGTGTTCGACCCCAGCCTGA CCTTCGACGACCTGGCCTGGATCAA GAGCCAGTGGCCCGGCAAGCTGGTG GTGAAGGGCATCCAGACCCTGGACG ACGCCAGGGCCGTGGTGGACAGGGG CGTGGACGGCATCGTGCTGAGCAAC CACGGCAGGCAGCTGGACAGGG CCCCCGTGCCCTTCCACCTGCTGCC CCACGTGGCCAGGGAGCTGGGCAAG CACACCGAGATCCTGGTGGACACCG GCATCATGAGCGGCGCCGACATCGT GGCCGCCATCGCCCTGGGCGCCAGG TGCACCCTGATCGGCAGGGCCTAC TGTACGGCCTGATGGCCGGCGGCGA GGCCGGCGTGAACAGGGCCATCGAG ATCCTGCAGACCGGCGTGATCAGGA CCATGAGGCTGCTGGGCGTGACCTG CCTGGAGGAGCTGAGCCCCAGGCAC GTGACCCAGCTGAGGAGGCTGGGCC CCATCGGCGCCCCCACCTGA (SEQ ID NO: 60) MAVNRRVPRVRDLAPLLQFNRPQFD TSKRRLGAALTIQDLRRIAKRRTPR AAFDYADGGAEDELSIARARQGFRD IEFHPTILRDVTTVCAGWNVLGQPT VLPFGIAPTGFTRLMHTEGEIAGAR AAAAAGIPFSLSTLATCAIEDLVIA VPQGRKWFQLYMWRDRDRSMALVRR VAAAGFDTMLVTVDVPVAGARLRDV RNGMSIPPALTLRTVLDAMGHPRWW FDLLTTEPLAFASLDRWPGTVGEYL NTVFDPSLTFDDLAWIKSQWPGKLV VKGIQTLDDARAVVDRGVDGIVLSN HGRQLDRAPVPFHLLPHVARELGK HTEILVDTGIMSGADIVAAIALGAR CTLIGRAYLYGLMAGGEAGVNRAIE ILQTGVIRTMRLLGVTCLEELSPRH VTQLRRLGPIGAPT (SEQ ID NO: 61) |
| Rv0012 | ATGAGGCTGACCCACCCCACCCCCT GCCCCGAGAACGGCGAGACCATGAT CGACAGGAGGAGGAGCGCCTGGAGG TTCAGCGTGCCCCTGGTGTGCCTGC TGGCCGGCCTGCTGCTGGCCGCCAC CCACGGCGTGAGCGGCGGCACCGAG ATCAGGAGGAGCGACGCCCCCAGGC TGGTGGACCTGGTGAGGAGGGCCCA GGCCAGCGTGAACAGGCTGGCCACC GAGAGGGAGGCCCTGACCACCAGGA TCGACAGCGTGCACGGCAGGAGCGT GGACACCGCCCTGGCCGCCATGCAG AGGAGGAGCGCCAAGCTGGCCGGCG TGGCCGCCATGAACCCCGTGCACGG CCCCGGCCTGGTGGTGACCCTGCAG GACGCCCAGAGGGACGCCAACGGCA GGTTCCCCAGGGACGCCAGCCCCGA CGACCTGGTGGTGCACCAGCAGGAC ATCGAGGCCGTGCTGAACGCCCTGT GGAACGCCGGCGCCGAGGCCATCCA GATGCAGGACCAGAGGATCATCGCC ATGAGCATCGCCAGGTGCGTGGGCA ACACCCTGCTGCTGAACGGCAGGAC CTACAGCCCCCCCTACACCATCGCC GCCATCGGCGACGCCGCCGCCATGC AGGCCGCCCTGGCCGCCGCCCCCCT GGTGACCCTGTACAAGCAGTACGTG GTGAGGTTCGGCCTGGGCTACTGCG AGGAGGTGCACCCCGACCTGCAGAT CGTGGGCTACGCCGACCCCGTGAGG ATGCACTTCGCCCAGCCCGCCGGCC CCCTGGACTACTGA (SEQ ID NO: 62) MRLTHPTPCPENGETMIDRRRSAWR FSVPLVCLLAGLLLAATHGVSGGTE IRRSDAPRLVDLVRRAQASVNRLAT EREALTTRIDSVHGRSVDTALAAMQ RRSAKLAGVAAMNPVHGPGLVVTLQ DAQRDANGRFPRDASPDDLVVHQQD IEAVLNALWNAGAEAIQMQDQRIIA MSIARCVGNTLLLNGRTYSPPYTIA AIGDAAAMQAALAAAPLVTLYKQYV VRFGLGYCEEVHPDLQIVGYADPVR MHFAQPAGPLDY (SEQ ID NO: 63) |

TABLE 7-continued

Variable Antigens

| Construct | Nucleotide sequence amino acid sequence |
|---|---|
| Rv0990c | GTGGCCGAGAGCAGCCTGAACCCCA<br>GCCTGGTGAGCAGGATCAGCGCCTT<br>CCTGAGGCCCGACTGGACCAGGACC<br>GTGAGGGCCAGGAGGTTCGCCGCCG<br>CCGGCCTGGTGATGCTGGCCGGCGT<br>GGCCGCCCTGAGGAGCAACCCCGAG<br>GACGACAGGAGCGAGGTGGTGGTGG<br>CCGCCCACGACCTGAGGCCCGGCAC<br>CGCCCTGACCCCCGGCGACGTGAGG<br>CTGGAGAAGAGGAGCGCCACCACCC<br>TGCCCGACGGCAGCCAGGCCGACCT<br>GGACGCCGTGGTGGGCAGCACCCTG<br>GCCAGCCCCACCAGGAGGGGCGAGG<br>TGCTGACCGACGTGAGGCTGCTGGG<br>CAGCAGGCTGGCCGAGAGCACCGCC<br>GGCCCCGACGCCAGGATCGTGCCCC<br>TGCACCTGGCCGACAGCGCCCTGGT<br>GGACCTGGTGAGGGTGGGCGACGTG<br>GTGGACGTGCTGGCCGCCCCCGTGA<br>CCGACAGCCCCGCCGCCCTGAGGCT<br>GCTGGCCACCGACGCCATCGTGGTG<br>CTGGTGAGCGCCCAGCAGAAGGCCC<br>AGGCCGCCGACAGCGACAGGGTGGT<br>GCTGGTGGCCCTGCCCGCCAGGCTG<br>GCCAACACCGTGGCCGGCGCCGCCC<br>TGGGCCAGACCGTGACCCTGACCCT<br>GCACTGA<br>(SEQ ID NO: 64)<br><br>VAESSLNPSLVSRISAFLRPDWTRT<br>VRARRFAAAGLVMLAGVAALRSNPE<br>DDRSEVVVAAHDLRPGTALTPGDVR<br>LEKRSATTLPDGSQADLDAVVGSTL<br>ASPTRRGEVLTDVRLLGSRLAESTA<br>GPDARIVPLHLADSALVDLVRVGDV<br>VDVLAAPVTDSPAALRLLATDAIVV<br>LVSAQQKAQAADSDRVVLVALPARL<br>ANTVAGAALGQTVTLTLH<br>(SEQ ID NO: 65) |
| Rv0995 | ATGGCCGTGGGCCCCCTGAGGGTGA<br>GCGCCGGCGTGATCAGGCTGAGGCC<br>CGTGAGGATGAGGGACGGCGTGCAC<br>TGGAGCAGGATCAGGCTGGCCGACA<br>GGGCCCACCTGGAGCCCTGGGAGCC<br>CAGCGCCGACGGCGAGTGGACCGTG<br>AGGCACACCGTGGCCGCCTGGCCCG<br>CCGTGTGCAGCGGCCTGAGGAGCGA<br>GGCCAGGAACGGCAGGATGCTGCCC<br>TACGTGATCGAGCTGGACGGCCAGT<br>TCTGCGGCCAGCTGACCATCGGCAA<br>CGTGACCCACGGCGCCCTGAGGAGC<br>GCCTGGATCGGCTACTGGGTGCCCA<br>GCGCCGCCACCGGCGGCGGCGTGGC<br>CACCGGCGCCCTGGCCCTGGGCCTG<br>GACCACTGCTTCGGCCCCGTGATGC<br>TGCACAGGGTGGAGGCCACCGTGAG<br>GCCCGAGAACGCCGCCAGCAGGGCC<br>GTGCTGGCCAAGGTGGGCTTCAGGG<br>AGGAGGGCCTGCTGAGGAGGTACCT<br>GGAGGTGGACAGGGCCTGGAGGGAC<br>CACCTGCTGATGGCCATCACCGTGG<br>AGGAGGTGTACGGCAGCGTGGCCAG<br>CACCCTGGTGAGGGCCGGCCACGCC<br>AGCTGGCCCTGA<br>(SEQ ID NO: 66)<br><br>MAVGPLRVSAGVIRLRPVRMRDGVH<br>WSRIRLADRAHLEPWEPSADGEWTV<br>RHTVAAWPAVCSGLRSEARNGRMLP<br>YVIELDGQFCGQLTIGNVTHGALRS |
| | AWIGYWVPSAATGGGVATGALALGL<br>DHCFGPVMLHRVEATVRPENAASRA<br>VLAKVGFREEGLLRRYLEVDRAWRD<br>HLLMAITVEEVYGSVASTLVRAGHA<br>SWP<br>(SEQ ID NO: 67) |

In some embodiments, a composition comprises at least two of the variable antigens. In some embodiments, the composition comprises at least three of the variable antigens. Inn some embodiments, the composition comprises at least four of the variable antigens. In some embodiments, the composition comprises at least five of the variable antigens. In some embodiments, the composition comprises all six variable antigens. In some embodiments, the composition comprises from at least two to six of the variable antigens. In some embodiments, the composition comprises from at least three to six of the variable antigens. In some embodiments, the composition comprises from at least four to six of the variable antigens. In some embodiments, the composition comprises five or six of the variable antigens. In some embodiments, the composition further comprises a pharmaceutically acceptable carrier.

In some embodiments, the fusion protein comprises at least two of the variable antigens. In some embodiments, the fusion protein comprises at least three of the variable antigens. In some embodiments, the fusion protein comprises at least four of the variable antigens. In some embodiments, the fusion protein comprises at least five of the variable antigens. In some embodiments, the fusion protein comprises all six variable antigens. In some embodiments, the fusion protein comprises from at least two to six of the variable antigens. In some embodiments, the fusion protein comprises from at least three to six of the variable antigens. In some embodiments, the fusion protein comprises from at least four to six of the variable antigens. In some embodiments, the fusion protein comprises five or six of the variable antigens.

In some embodiments, the fusion protein comprises Rv2719c, Rv0010c, and Rv1872c. In some embodiments, the fusion protein comprises Rv0012, Rv0990c, and Rv0995.

In any of the embodiments of fusion proteins set forth herein, the individual variable antigens can be present in any order. For example, for a fusion protein comprising Rv0012, Rv0990c, and Rv0995 antigens, the first (or N-terminal) antigen may be Rv0012, Rv0990c, or Rv0995; the second antigen may be Rv0012, Rv0990c, or Rv0995 (whichever one is not the first variable antigen); and the third antigen may be Rv0012, Rv0990c, or Rv0995 (whichever one is not the first or second variable antigen). Likewise for every fusion protein disclosed herein.

Individual variable antigens may be linked together in a C-terminus to N-terminus or N-terminus to C-terminus manner without any linker. Alternately, a linker may be present between any two variable antigens within any of the fusion proteins disclosed herein. In some embodiments, the linker is a segment of DNA or RNA optionally containing one or more restrictions sites, wherein the linker is inserted between nucleic acid molecules encoding two variable antigens of any of the fusion proteins disclosed herein.

In some embodiments, the fusion protein comprises Rv2719c-Rv0010c-Rv1872c (Construct F; see Table 8). The nucleotide sequence is SEQ ID NO:68, and the corresponding amino acid sequence is SEQ ID NO:69 (including a C-terminal HA tag (YPYDVPDYA; SEQ ID NO:17) added).

In some embodiments, the fusion protein comprises Rv0012-Rv0990c-Rv0995 (Construct G; see Table 8). The nucleotide sequence is SEQ ID NO:70, and the corresponding amino acid sequence is SEQ ID NO:71 (including a C-terminal HA tag (YPYDVPDYA; SEQ ID NO:17) added).

TABLE 8

Variable Antigen Cassette

| Construct | nucleotide sequence amino acid sequence |
|---|---|
| F | ATGACCCCCGTGAGGCCCCCCCACA CCCCCGACCCCCTGAACCTGAGGGG CCCCCTGGACGGCCCCAGGTGGAGG AGGGCCGAGCCCGCCCAGAGCAGGA GGCCCGGCAGGAGCAGGCCCGGCGG CGCCCCCCTGAGGTACCACAGGACC GGCGTGGGCATGAGCAGGACCGGCC ACGGCAGCAGGCCCGTGCCCCCCGC CACCACCGTGGGCCTGGCCCTGCTG GCCGCCGCCATCACCCTGTGGCTGG GCCTGGTGGCCCAGTTCGGCCAGAT GATCACCGGCGGCAGCGCCGACGGC AGCGCCGACAGCACCGGCAGGGTGC CCGACAGGCTGGCCGTGGTGAGGGT GGAGACCGGCGAGAGCCTGTACGAC GTGGCCGTGAGGGTGGCCCCCAACG CCCCCACCAGGCAGGTGGCCGACAG GATCAGGGAGCTGAACGGCCTGCAG ACCCCCGCCCTGGCCGTGGGCCAGA CCCTGATCGCCCCCGTGGGCATGCA GCAGACCGCCTGGGCCCCCAGGACC AGCGGCATCGCCGGCTGCGGCGCCG GCGGCGTGGTGATGGCCATCGCCAG CGTGACCCTGGTGACCGACACCCCC GGCAGGGTGCTGACCGGCGTGGCCG CCCTGGGCCTGATCCTGTTCGCCAG CGCCACCTGGAGGGCCAGGCCCAGG CTGGCCATCACCCCCGACGGCCTGG CCATCAGGGGCTGGTTCAGGACCCA GCTGCTGAGGCACAGCAACATCAAG ATCATCAGGATCGACGAGTTCAGGA GGTACGGCAGGCTGGTGAGGCTGCT GGAGATCGAGACCGTGAGCGGCGGC CTGCTGATCCTGAGCAGGTGGGACC TGGGCACCGACCCCGTGGAGGTGCT GGACGCCCTGACCGCCGGCTACGCC GGCAGGGGCCAGAGGATGGCCGTGA ACAGGAGGGTGCCCAGGGTGAGGGA CCTGGCCCCCCTGCTGCAGTTCAAC AGGCCCCAGTTCGACACCAGCAAGA GGAGGCTGGGCGCCGCCCTGACCAT CCAGGACCTGAGGAGGATCGCCAAG AGGAGGACCCCCAGGGCCGCCTTCG ACTACGCCGACGGCGGCGCCGAGGA CGAGCTGAGCATCGCCAGGGCCGAG GGCGAGGCTTCAGGGACATCGAGTT CCACCCCACCATCCTGAGGGACGTG ACCACCGTGTGCGCCGGCTGGAACG TGCTGGGCCAGCCCACCGTGCTGCC CTTCGGCATCGCCCCCACCGGCTTC ACCAGGCTGATGCACACCGAGGGCG AGATCGCCGGCGCCAGGGCCGCCGC CGCCGCGGCATCCCCTTCAGCCTG AGCACCCTGGCCACCTGCGCCATCG AGGACCTGGTGATCGCCGTGCCCCA GGGCAGGAAGTGGTTCCAGCTGTA CATGTGGAGGGACAGGGACAGGAGC ATGGCCCTGGTGAGGAGGGTGGCCG CCGCCGGCTTCGACACCATGCTGGT GACCGTGGACGTGCCCGTGGCCGGC GCCAGGCTGAGGGACGTGAGGAACG GCATGAGCATCCCCCCCGCCCTGAC CCTGAGGACCGTGCTGGACGCCATG GGCCACCCCAGGTGGTGGTTCGACC TGCTGACCACCGAGCCCCTGGCCTT CGCCAGCCTGGACAGGTGGCCCGGC ACCGTGGGCGAGTACCTGAACACCG TGTTCGACCCCAGCCTGACCTTCGA CGACCTGGCCTGGATCAAGAGCCAG TGGCCCGGCAAGCTGGTGGTGAAGG GCATCCAGACCCTGGACGACGCCAG GGCCGTGGTGGACAGGGGCGTGGAC GGCATCGTGCTGAGCAACCACGGCG GCAGGCAGCTGGACAGGGCCCCCGT GCCCTTCCACCTGCTGCCCCACGTG GCCAGGGAGCTGGGCAAGCACACCG AGATCCTGGTGGACACCGGCATCAT GAGCGGCGCCGACATCGTGGCCGCC ATCGCCCTGGGCGCCAGGTGCACCC TGATCGGCAGGGCCTACCTGTACGG CCTGATGGCCGGCGGCGAGGCCGGC GTGAACAGGGCCATCGAGATCCTGC AGACCGGCGTGATCAGGACCATGAG GCTGCTGGGCGTGACCTGCCTGGAG GAGCTGAGCCCCAGGCACGTGACCC AGCTGAGGAGGCTGGGCCCCATCGG CGCCCCCACCTACCCCTACGACGTG CCCGACTACGCCTGA (SEQ ID NO: 68) MTPVRPPHTPDPLNLRGPLDGPRWR RAEPAQSRRPGRSRPGGAPLRYHRT GVGMSRTGHGSRPVPPATTVGLALL AAAITLWLGLVAQFGQMITGGSADG SADSTGRVPDRLAVVRVETGESLYD VAVRVAPNAPTRQVADRIRELNGLQ TPALAVGQTLIAPVGMQQTAWAPRT SGIAGCGAGGVVMAIASVTLVTDTP GRVLTGVAALGLILFASATWRARPR LAITPDGLAIRGWFRTQLLRHSNIK IIRIDEFRRYGRLVRLLEIETVSGG LLILSRWDLGTDPVEVLDALTAAGY AGRGQRMAVNRRVPRVRDLAPLLQF NRPQFDTSKRRLGAALTIQDLRRIA KRRTPRAAFDYADGGAEDELSIARA EGEIAGARAAAAAGIPFSLSTLATC AIEDLVIAVPQGRKWFQLYMWRDRD RSMALVRRVAAAGFDTMLVTVDVPV AGARLRDVRNGMSIPPALTLRTVLD AMGHPRWWFDLLTTEPLAFASLDRW PGTVGEYLNTVFDPSLTFDDLAWIK SQWPGKLVVKGIQTLDDARAVVDRG VDGIVLSNHGGRQLDRAPVPFHLLP HVARELGKHTEILVDTGIMSGADIV AAIALGARCTLIGRAYLYGLMAGGE AGVNRAIEILQTGVIRTMRLLGVTC LEELSPRHVTQLRRLGPIGAPTYPY DVPDYA (SEQ ID NO: 69) |
| G | ATGAGGCTGACCCACCCCACCCCCT GCCCCGAGAACGGCGAGACCATGAT CGACAGGAGGAGGAGCGCCTGGAGG TTCAGCGTGCCCCTGGTGTGCCTGC TGGCCGGCCTGCTGCTGGCCGCCAC CCACGGCGTGAGCGGCGGCACCGAG ATCAGGAGGAGCGACGCCCCCAGGC TGGTGGACCTGGTGAGGAGGGCCCA GGCCAGCGTGAACAGGCTGGCCACC GAGAGGGAGGCCCTGACCACCAGGA TCGACGTGCACGGCAGGAGCGT GGACACCGCCCTGGCCGCCATGCAG AGGAGGAGCGCCAAGCTGGCCGGCG TGGCCGCCATGAACCCCGTGCACGG CCCCGGCCTGGTGGTGACCCTGCAG GACGCCCAGAGGGACGCCAACGGCA |

TABLE 8-continued

Variable Antigen Cassette

| Construct | nucleotide sequence amino acid sequence |
|---|---|
| | GGTTCCCCAGGGACGCCAGCCCCGA |
| | CGACCTGGTGGTGCACCAGCAGGAC |
| | ATCGAGGCCGTGCTGAAC-GCCCTG |
| | TGGAACGCCGGCGCCGAGGCCATCC |
| | AGATGCAGGACCAGAGGATCATCGC |
| | CATGAGCATCGCCAGGTGCGTGGGC |
| | AACACCCTGCTGCTGAACGGCAGGA |
| | CCTACAGCCCCCCCTACACCATCGC |
| | CGCCATCGGCGACGCCGCCGCCATG |
| | CAGGCCGCCCTGGCCGCCGCCCCC |
| | TGGTGACCCTGTACAAGCAGTACGT |
| | GGTGAGGTTCGGCCTGGGCTACTGC |
| | GAGGAGGTGCACCCCGACCTGCAGA |
| | TCGTGGGCTACGCCGACCCCGTGAG |
| | GATGCACTTCGCCCAGCCCGCCGGC |
| | CCCCTGGACTACGTGGCCGAGAGCA |
| | GCCTGAACCCCAGCCTGGTGAGCAG |
| | GATCAGCGCC7TCCTGAGGCCCGAC |
| | TGGACCAGGACCGTGAGGGCCAGGA |
| | GGTTCGCCGCCGCCGGCCTGGTGAT |
| | GCTGGCCGGCGTGGCCGCCCTGAGG |
| | AGCAACeCCGAGGACGACAGGAGCG |
| | AGGTGGTGGTGGCCGCCCACGACCT |
| | GAGGCCCGGCACCGCCCTGACCCCC |
| | GGCGACGTGAGGCTGGAGAAGAGGA |
| | GCGCCACCACCCTGCCCGACGGCAG |
| | CCAGGCCGACCTGGACGCCGTGGTG |
| | GGCAGCACCCTGGCCAGCCCCACCA |
| | GGAGGGGCGAGGTGCTGACCGACGT |
| | GAGGCTGCTGGGCAGCAGGCTGGCC |
| | GAGAGCACCGCCGGCCCCGACGCCA |
| | GGATCGTGCCCCTGCACCTGGCCGA |
| | CAGCGCCCTGGTGGACCTGGTGAGG |
| | GTGGGCGACGTGGTGGACGTGCTGG |
| | CCGCCCCCGTGACCGACAGCCCCGC |
| | CGCCCTGAGGCTGCTGGCCACCGAC |
| | GCCATCGTGGTGCTGGTGAGCGCCC |
| | AGCAGAAGGCCCAGGCCGCCGACAG |
| | CGACAGGGTGGTGCTGGTGGCCCTG |
| | CCCGCCAGGCTGGCCAACACCGTGG |
| | CCGGCGCCGCCCTGGGCCAGACCGT |
| | GACCCTGACCCTGCACATGGCCGTG |
| | GGCCCCCTGAGGGTGAGCGCCGGCG |
| | TGATCAGGCTGAGGCCCGTGAGGAT |
| | GAGGGACGGCGTGCACTGGAGCAGG |
| | ATCAGGCTGGCCGACAGGGCCCACC |
| | TGGAGCCCTGGGAGCCCAGCGCCGA |
| | CGGCGAGTGGACCGTGAGGCACACC |
| | GTGGCCGCCTGGCCCGCCGTGTGCA |
| | GCGGCCTGAGGAGCGAGGCCAGGAA |
| | CGGCAGGATGCTGCCCTACGTGATC |
| | GAGCTGGACGGCCAGTTCTGCGGCC |
| | AGCTGACCATCGGCAACGTGACCCA |
| | CGGCGCCCTGAGGAGCGCCTGGATC |
| | GGCTACTGGGTGCCCAGCGCCGCCA |
| | CCGGCGGCGGCGTGGCCACCGGCGC |
| | CCTGGCCCTGGGCCTGGACCACTGC |
| | TTCGGCCCCGTGATGCTGCACAGGG |
| | TGGAGGCCACCGTGAGGCCCGAGAA |
| | CGCCGCCAGCAGGGCCGTGCTGGCC |
| | AAGGTGGGCTTCAGGGAGGAGGGCC |
| | TGCTGAGGAGGTACCTGGAGGTGGA |
| | CAGGGCCTGGAGGGACCACCTGCTG |
| | ATGGCCATCACCGTGGAGGAGGTGT |
| | ACGGCAGCGTGGCCAGCACCCTGGT |
| | GAGGGCCGGCCACGCCAGCTGGCCC |
| | TACCCCTACGACGTGCCCGACTACG |
| | CCTGA |
| | (SEQ ID NO: 70) |
| | |
| | MRLTHPTPCPENGETMIDRRRSAWR |
| | FSVPLVCLLAGLLLAATHGVSGGTE |
| | IRRSDAPRLVDLVRRAQASVNRLAT |
| | EREALTTRIDSVHGRSVDTALAAMQ |
| | RRSAKLAGVAAMNPVHGPGLVVTLQ |
| | DAQRDANGRFPRDASPDDLVVHQQD |
| | IEAVLNALWNAGAEAIQMQDQRIIA |
| | MSIARCVGNTLLLNGRTYSPPYTIA |
| | AIGDAAAMQAALAAAPLVTLYKQYV |
| | VRFGLGYCEEVHPDLQIVGYADPVR |
| | MHFAQPAGPLDYVAESSLNPSLVSR |
| | ISAFLRPDWTRTVRARRFAAAGLVM |
| | LAGVAALRSNPEDDRSEVVVAAHDL |
| | RPGTALTPGDVRLEKRSATTLPDGS |
| | QADLDAVVGSTLASPTRRGEVLTDV |
| | RLLGSRLAESTAGPDARIVPLHLAD |
| | SALVDLVRVGDVVDVLAAPVTDSPA |
| | ALRLLATDAIVVLVSAQQKAQAADS |
| | DRVVLVALPARLANTVAGAALGQTV |
| | TLTLHMAVGPLRVSAGVIRLRPVRM |
| | RDGVHWSRIRLADRAHLEPWEPSAD |
| | GEWTVRHTVAAWPAVCSGLRSEARN |
| | GRMLPYVIELDGQFCGQLTIGNVTH |
| | GALRSAWIGYWVPSAATGGGVATGA |
| | LALGLDHCFGPVMLHRVEATVRPEN |
| | AASRAVLAKVGFREEGLLRRYLEVD |
| | RAWRDHLLMAITVEEVYGSVASTLV |
| | RAGHASWPYPYDVPDYA |
| | (SEQ ID NO: 71) |

Any Mtb antigen, including any Mtb antigen within any of the fusion proteins described herein, can have an amino acid sequence that is 100%, or from 70% to 99.9%, identical to the particular amino acid sequence listed in Tables 1 through 8. The amino acid sequence of any individual Mtb antigen, including any Mtb antigen within any of the fusion proteins described herein, can be at least 70%, at least 75%, at least 80%, at least 85%, at least 90%, at least 95%, at least 96%, at least 97%, at least 98%, or at least 99% identical to the particular amino acid sequence listed in Tables 1 through 8. Identity or similarity with respect to an amino acid or nucleotide sequence is defined herein as the percentage of amino acid residues (or nucleotide residues as the case may be) in the particular Mtb antigen that are identical (i.e., same residue) with the amino acid or nucleotide sequence for the Mtb antigen shown in Tables 1 through 8, after aligning the sequences and introducing gaps, if necessary, to achieve the maximum percent sequence identity. Percent sequence identity can be determined by, for example, the Gap program (Wisconsin Sequence Analysis Package, Version 8 for Unix, Genetics Computer Group, University Research Park, Madison WI), using default settings, which uses the algorithm of Smith and Waterman (Adv. Appl. Math., 1981, 2, 482-489). Any amino acid number calculated as a % identity can be rounded up or down, as the case may be, to the closest whole number.

Any Mtb antigen, including any Mtb antigen within any of the fusion proteins described herein, can be fragments of the particular amino acid sequences listed in Tables 1, 3, 5, and 7. The amino acid sequence of any individual Mtb antigen, including any Mtb antigen within of the fusion proteins described herein, can be missing consecutive amino acids constituting at least 20%, at least 15%, at least 10%, at least 5%, at least 4%, at least 3%, at least 2%, or at least 1%, of the particular amino acid sequences listed in Tables 1, 3, 5, and 7. The omitted consecutive amino acids may be from the C-terminus or N-terminus portion of the antigen. Alternately, the omitted consecutive amino acids may be from the internal portion of the antigen, thus retaining at least its C-terminus and N-terminus amino acids of the antigen.

Any Mtb antigen, including any Mtb antigen within any of the fusion proteins described herein, can have one or more amino acid additions, deletions, or substitutions compared to the particular amino acid sequences listed in Tables 1 through 8. Any individual Mtb antigen, including any Mtb antigen within any of the fusion proteins described herein, can have at least one, at least two, at least three, at least four, at least five, at least six, at least seven, at least eight, at least nine, at least ten, at least eleven, or at least twelve amino acid additions, deletions, or substitutions compared to the particular amino acid sequences listed in Tables 1 through 8. Any individual Mtb antigen, including any Mtb antigen within any of the fusion proteins described herein, can have one, two, three, four, five, six, seven, eight, nine, ten, eleven, or twelve amino acid additions, deletions, or substitutions compared to the particular amino acid sequences listed in Tables 1 through 8. The amino acid additions, deletions, or substitutions can take place at any amino acid position within the Mtb antigen.

Where a particular Mtb antigen, including any Mtb antigen within of the fusion proteins described herein, comprises at least one or more substitutions, the substituted amino acid(s) can each be, independently, any naturally occurring amino acid or any non-naturally occurring amino acid. Thus, a particular Mtb antigen may comprise one or more amino acid substitutions that are naturally occurring amino acids and/or one or more amino acid substitutions that are non-naturally occurring amino acids. Individual amino acid substitutions are selected from any one of the following: 1) the set of amino acids with nonpolar sidechains, for example, Ala, Cys, Ile, Leu, Met, Phe, Pro, Val; 2) the set of amino acids with negatively charged side chains, for example, Asp, Glu; 3) the set of amino acids with positively charged sidechains, for example, Arg, His, Lys; and 4) the set of amino acids with uncharged polar sidechains, for example, Asn, Cys, Gln, Gly, His, Met, Phe, Ser, Thr, Trp, Tyr, to which are added Cys, Gly, Met and Phe. Substitutions of a member of one class with another member of the same class are contemplated herein. Naturally occurring amino acids include, for example, alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan (Trp), tyrosine (Tyr), and valine (Val). Non-naturally occurring amino acids include, for example, norleucine, ornithine, norvaline, homoserine, and other amino acid residue analogues such as those described in Ellman et al., Meth. Enzym., 1991, 202, 301-336. To generate such non-naturally occurring amino acid residues, the procedures of Noren et al., Science, 1989, 244, 182 and Ellman et al., supra, can be used. Briefly, these procedures involve chemically activating a suppressor tRNA with a non-naturally occurring amino acid residue followed by in vitro transcription and translation of the RNA.

The Mtb antigens, including any Mtb antigen within any of the fusion proteins described herein, which are modified as described herein retain their ability to elicit an immune response against *Mycobacterium tuberculosis*. That is, modification of a particular Mtb antigen, including any Mtb antigen within any of the fusion proteins described herein, will still allow the resultant Mtb antigen, or fusion protein comprising the same, to elicit an immune response against *Mycobacterium tuberculosis*.

The present disclosure also provides nucleic acid molecules encoding any of the fusion proteins described herein that comprise at least two Mtb antigens. The nucleic acid molecules described herein and in Tables 1 through 8 are representative. The specific sequences recited in Tables 1 through 8 are simply representative examples of nucleic acid molecules that can encode a particular Mtb antigen within a fusion protein. One skilled in the art having knowledge of the genetic code can routinely prepare and design a plethora of nucleic acid molecules encoding the same Mtb antigen. The length and nucleotide content of any particular nucleic acid molecule is dictated by the desired amino acid sequence of the encoded Mtb antigen. The nucleic acid molecule sequences shown in Tables 1 through 8 are DNA, although RNA nucleic acid molecules are also contemplated.

The present disclosure also provides vectors encoding any of the Mtb antigens, including Mtb antigens within any of the fusion proteins described herein, including any of the modified versions described herein. The vector can be capable of expressing an Mtb antigen in the cell of a mammal in a quantity effective to elicit an immune response in the mammal. The vector can be recombinant. The vector can comprise heterologous nucleic acid encoding the antigen. The vector can be a plasmid. In some embodiments, the plasmid is a DNA plasmid, such as a pVAX backbone vector. The vector can be useful for transfecting cells with nucleic acid encoding an Mtb antigen, which the transformed host cell is cultured and maintained under conditions wherein expression of the antigen takes place.

In some embodiments, coding sequences can be optimized for stability and high levels of expression. In some instances, codons are selected to reduce secondary structure formation of the RNA such as that formed due to intramolecular bonding.

In some embodiments, the vectors can comprise regulatory elements for gene expression of the coding sequences of the nucleic acid. The regulatory elements can be a promoter, an enhancer an initiation codon, a stop codon, or a polyadenylation signal. In some embodiments, the vector can comprise heterologous nucleic acid encoding an Mtb antigen and can further comprise an initiation codon, which is upstream of the antigen coding sequence, and a stop codon, which is downstream of the antigen coding sequence. The initiation and termination codon are in frame with the antigen coding sequence.

The vector can also comprise a promoter that is operably linked to the antigen coding sequence. The promoter operably linked to the Mtb antigen coding sequence can be a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter, or the like. The promoter can also be a promoter from a human gene such as human actin, human myosin, human hemoglobin, human muscle creatine, or human metalothionein. The promoter can also be a tissue specific promoter, such as a muscle or skin specific promoter, natural or synthetic. Representative examples of promoters include the bacteriophage T7 promoter, bacteriophage T3 promoter, SP6 promoter, lac operator-promoter, tac promoter, mycobacterial Hsp60 promoter, SV40 late promoter, SV40 early promoter, RSV-LTR promoter, CMV IE promoter, SV40 early promoter or SV40 late promoter and the CMV IE promoter.

The vector can also comprise a polyadenylation signal, which can be downstream of the antigen coding sequence. The polyadenylation signal can be a SV40 polyadenylation signal, LTR polyadenylation signal, CMV polyadeylation signal, bovine growth hormone (bGH) polyadenylation signal, human growth hormone (hGH) polyadenylation signal, or human β-globin polyadenylation signal. The SV40 polyadenylation signal can be a polyadenylation signal from a pCEP4 vector (Invitrogen, San Diego, CA).

The vector can also comprise an enhancer upstream of the consensus BoNT-A, BoNT-B, BoNT-E, and BoNT-F antigen sequences. The enhancer can be necessary for DNA expression. The enhancer can be human actin, human myosin, human hemoglobin, human muscle creatine or a viral enhancer such as one from CMV, HA, RSV or EBV. Polynucleotide function enhancers are described in U.S. Pat. Nos. 5,593,972, 5,962,428, and WO94/016737.

The vector can also comprise a mammalian origin of replication in order to maintain the vector extrachromosomally and produce multiple copies of the vector in a cell. The vector can be pVAX1, pCEP4 or pREP4 from Invitrogen (San Diego, CA), which can comprise the Epstein Barr virus origin of replication and nuclear antigen EBNA-1 coding region, which can produce high copy episomal replication without integration. The vector can be pVAX1 or a pVax1 variant with changes such as the variant plasmid described herein. The variant pVax1 plasmid is a 2998 basepair variant of the backbone vector plasmid pVAX1 (Invitrogen, Carlsbad CA). The CMV promoter is located at bases 137-724. The T7 promoter/priming site is at bases 664-683. Multiple cloning sites are at bases 696-811. Bovine GH polyadenylation signal is at bases 829-1053. The Kanamycin resistance gene is at bases 1226-2020. The pUC origin is at bases 2320-2993.

The vector can also comprise a regulatory sequence, which can be well suited for gene expression in a mammalian or human cell into which the vector is administered. The consensus coding sequence can comprise a codon, which can allow more efficient transcription of the coding sequence in the host cell.

The vector can be pSE420 (Invitrogen, San Diego, Calif.) or pET28b (EMD Millipore, Billerca, Mass.), which can be used for protein production in *Escherichia coli* (*E. coli*). The vector can also be pYES2 (Invitrogen, San Diego, Calif.), which can be used for protein production in *Saccharomyces cerevisiae* strains of yeast. The vector can also be of the MAXBAC™ complete baculovirus expression system (Invitrogen, San Diego, Calif.), which can be used for protein production in insect cells. The vector can also be pcDNA I or pcDNA3 (Invitrogen, San Diego, Calif.), which may be used for protein production in mammalian cells such as Chinese hamster ovary (CHO) cells. The vector can be expression vectors or systems to produce protein by routine techniques and readily available starting materials including Sambrook et al., Molecular Cloning and Laboratory Manual, Second Ed., Cold Spring Harbor (1989).

In some embodiments, the vector is a viral vector. Suitable viral vectors include, but are not limited to, an adenovirus vector, an adeno-associated virus vector, a poxvirus vector (such as, for example, vaccinia virus vector), a paramyxovirus vector, a fowlpox virus vector, an attenuated yellow fever vectors (such as, for example, YFV-17D), an alphavirus vector, a retrovirus vector (such as, for example, lentivirus vector), a Sendai virus vector, and cytomegalovirus (CMV) vector. Suitable adenovirus vectors include, but are not limited to, adenovirus 4, adenovirus 5, chimpanzee adenovirus 3, chimpanzee adenovirus 63, and chimpanzee adenovirus 68. A suitable vaccinia virus vector includes, but is not limited to, modified vaccinia Ankara (MVA). Suitable paramyxovirus vectors include, but are not limited to, modified parainfluenza virus (PIV2) and recombinant human parainfluenza virus (rHPIV2). Suitable CMV vectors include, but are not limited to, Rhesus Macaque CMV (RhCMV) vectors and Human CMV (HCMV) vectors. In some embodiments, the vector is present within a composition comprising a pharmaceutically acceptable carrier. One skilled in the art is readily familiar with numerous vectors, many of which are commercially available.

In some embodiments, the vector is a non-viral vector. In some embodiments, the non-viral vector is RNA, such as mRNA. In some embodiments, the mRNA is protamine-complexed mRNA, wherein the Mtb antigen or fusion protein is encoded by the mRNA, and the protamine complexes contribute a strong immunostimulatory signal. An exemplary mRNA vector platform is RNActive® (CureVac Inc).

The present disclosure also provides host cells comprising any of the nucleic acid molecules or vectors disclosed herein. The host cells can be used, for example, to express the Mtb antigens, or fragments of thereof. The Mtb antigens, or fragments thereof, can also be expressed in cells in vivo. The host cell that is transformed (for example, transfected) to produce the Mtb antigens, or fragments of thereof can be an immortalised mammalian cell line, such as those of lymphoid origin (for example, a myeloma, hybridoma, trioma or quadroma cell line).

The host cell can also include normal lymphoid cells, such as B-cells, that have been immortalized by transformation with a virus (for example, the Epstein-Barr virus).

In some embodiments, the host cells include, but are not limited to: bacterial cells, such as *E. coli, Caulobacter crescentus, Streptomyces* species, and *Salmonella typhimurium*; yeast cells, such as *Saccharomyces cerevisiae, Schizosaccharomyces pombe, Pichia pastoris, Pichia methanolica*; insect cell lines, such as those from *Spodoptera frugiperda* (for example, Sf9 and Sf21 cell lines, and expresSF™ cells (Protein Sciences Corp., Meriden, CT, USA)), *Drosophila* S2 cells, and *Trichoplusia* in High Five® Cells (Invitrogen, Carlsbad, CA, USA); and mammalian cells, such as COS1 and COS7 cells, Chinese hamster ovary (CHO) cells, NS0 myeloma cells, NIH 3T3 cells, 293 cells, Procel192S, perC6, HEPG2 cells, HeLa cells, L cells, HeLa, MDCK, HEK293, WI38, murine ES cell lines (for example, from strains 129/SV, C57/BL6, DBA-1, 129/SVJ), K562, Jurkat cells, and BW5147. Other useful mammalian cell lines are well known and readily available from the American Type Culture Collection ("ATCC") (Manassas, VA, USA) and the National Institute of General Medical Sciences (NIGMS) Human Genetic Cell Repository at the Conch Cell Repositories (Camden, NJ, USA). In some embodiments, the cell is a recombinant BCG. These cell types are only representative and are not meant to be an exhaustive list.

Among other considerations, some of which are described above, a host cell strain be chosen for its ability to process the expressed. Mtb antigens, or fragment thereof, in the desired fashion. Post-translational modifications of the polypeptide include, but are not limited to, glycosylation, acetylation, carboxylation, phosphorylation, lipidation, and acylation, and it is an aspect of the present disclosure to provide Mtb antigens thereof with one or more of these post-translational modifications.

In some embodiments, the recombinant BCG has been genetically engineered to express a functional endosomalytic protein that is bioactive at pH values near neutrality (e.g. about pH 6-8 or about 6.5 to 7.5). The endosomalytic protein is active within *Mycobacteria*-containing endosomes, which typically have an internal pH near neutrality. The activity of the endosomalytic protein produced by the rBCG results in disruption of the endosome, permitting the rBCG to escape from the endosome and into the cytoplasm of the cell.

In some embodiments, the endosomalytic protein that is introduced into the rBCG by genetic engineering is Perfringolysin O (PfoA) from *Clostridium perfringens* or a mutant thereof, such as $PfoA_{G137Q}$, as described in WO 2007/058663.

In some embodiments, the *Mycobacteria* are attenuated, as exemplified by BCG. However, those of skill in the art will recognize that other attenuated and nonattenuated *Mycobacteria* exist which would also be suitable for use herein. Examples of additional types of *Mycobacteria* include, but are not limited to, *M. tuberculosis* strain CDC1551, *M. tuberculosis* strain Beijing, *M. tuberculosis* strain H37Ra (ATCC #:25177), *M. tuberculosis* strain H37Rv (ATCC #:25618), *M. bovis* (ATCC #:19211 and 27291), *M. fortuitum* (ATCC #:15073), *M. smegmatis* (ATCC #:12051 and 12549), *M. Intracellulare* (ATCC #:35772 and 13209), *M. kansasii* (ATCC #:21982 and 35775) *M. avium* (MUM (ATCC #:19421 and 25291), *M. gailinarum* (ATCC #:19711), *M. vaccae* (ATCC #:15483 and 23024), *M. leprae* (ATCC #:), marinarum (ATCC #:11566 and 11567), and *M. microtti* (ATCC #:11152).

Examples of attenuated *Mycobacterium* strains include, but are not restricted To, *M. tuberculosis* pantothenate auxotroph strain, *M. tuberculosis* rpoV mutant strain, *M. tuberculosis* leucine auxotroph strain, BCG Danish strain (ATCC #35733), BCG Japanese strain (ATCC #35737), BCG Chicago strain (ATCC #27289), BCG Copenhagen strain (ATCC #: 27290), BCG Pasteur strain (ATCC #: 35734), BCG Glaxo strain (ATCC #: 35741), BCG Connaught strain (ATCC #35745), BCG Montreal (ATCC #35746), BCG1331 strain, BCG Tokyo strain, BCG Moreau strain, BCG-Pasteur Aeras, and BCG Moscow strain.

In some embodiments, the cell comprising the one or more vector(s) is present with composition comprising a pharmaceutically acceptable carrier.

In some embodiments, the Mtb antigen, or fragment thereof, is labeled with a detectable marker. Detectable markers include, but are not limited to, radioactive isotopes (such as $P^{32}$ and $S^{35}$), enzymes (such as horseradish peroxidase, chloramphenicol acetyltransferase (CAT), β-galactosidase (β-gal), and the like), fluorochromes, chromophores, colloidal gold, dyes, and biotin. The labeled Mtb antigens, or fragments thereof, can be used to carry out diagnostic procedures in a variety of cell or tissue types. For imaging procedures, in vitro or in vivo, the Mtb antigens can be labeled with additional agents, such as NMR contrasting agents, X-ray contrasting agents, or quantum dots. Methods for attaching a detectable agent to polypeptides are known in the art. The Mtb antigens can also be attached to an insoluble support (such as a bead, a glass or plastic slide, or the like).

In some embodiments, the Mtb antigens, or fragment thereof, can be conjugated to a therapeutic agent including, but not limited to, radioisotopes (such as $^{111}In$ or $^{90}Y$), toxins (such as tetanus toxoid or ricin), toxoids, and chemotherapeutic agents.

In some embodiments, the Mtb antigens, or fragments thereof, can be conjugated to an imaging agent. Imaging agents include, for example, a labeling moiety (such as biotin, fluorescent moieties, radioactive moieties, histidine tag or other peptide tags) for easy isolation or detection.

The present disclosure also provides compositions comprising at least two Mtb antigens or at least one Mtb fusion protein. In some embodiments, the at least two Mtb antigens are not present in a fusion protein. In some embodiments, the at least two Mtb antigens are in the form of a protein and not nucleic acid molecules encoding the Mtb antigens.

The present disclosure also provides any of the Mtb compositions described herein in which the composition comprises at least one nucleic acid molecule encoding at least one of the Mtb antigens. In some embodiments, the composition comprises one Mtb antigen in protein form and one or two nucleic acid molecules encoding two Mtb antigens. In some embodiments, the composition comprises two Mtb antigens in protein form, optionally as a fusion protein, and one nucleic acid molecule encoding one Mtb antigen. Thus, the present composition can be a mixture of a protein Mtb antigen(s) and nucleic acid molecule(s) encoding an Mtb antigen(s) to make up any of the compositions described herein.

In some embodiments, at least two Mtb antigens, or a fusion protein comprising the same, are encoded by one or more nucleic acid molecules within one or more vectors. In some embodiments, the one or more vectors is one or more viral vectors. In some embodiments, the one or more viral vectors are any one or more of an adenovirus vector, an adeno-associated virus vector, a poxvirus vector (such as, for example, vaccinia virus vector), a paramyxovirus vector, a fowlpox virus vector, an attenuated yellow fever vectors (such as, for example, YFV-17D), an alphavirus vector, a retrovirus vector (such as, for example, lentivirus vector), a Sendai virus vector, and CMV vector. In some embodiments, the adenovirus vector is adenovirus 4, adenovirus 5, chimpanzee adenovirus 3, chimpanzee adenovirus 63, or chimpanzee adenovirus 68. In some embodiments, the vaccinia virus vector is MVA. In some embodiments, the paramyxovirus vector is PIV2 or rHPIV2. In some embodiments, the CMV vector is a RhCMV vector of an HCMV vector. In some embodiments, the vector is present within a composition comprising a pharmaceutically acceptable carrier. In some embodiments, the at least two Mtb antigens are encoded by a single nucleic acid molecule within the same expression vector as a fusion protein.

In some embodiments, the one or more vectors is a non-viral vector. In some embodiments, the non-viral vector is RNA, such as mRNA. In some embodiments, the mRNA is protamine-complexed mRNA. An exemplary mRNA vector platform is RNActive® (CureVac Inc).

In some embodiments, where a rBCG is used as the vehicle to deliver the Mtb antigens, or fusion proteins, or nucleic acids and or vectors comprising or encoding the same, expression of all or part of the Dos R regulon is not up-regulated in the rBCG. In some embodiments, one or more of the following Dos R regulon antigens are not up-regulated in the rBCG: Rv1738, Rv2623, Rv2031c, Rv2032, Rv2626c, Rv2005c, Rv3127, Rv1733c, Rv1996, Rv2628c, Rv0079, Rv3130c, Rv3131, Rv1813c, Rv2006, Rv2029c, Rv2627c, Rv2030c, Rv3132c, and Rv2629. In some embodiments, the rBCG does not comprise up-regulation of: 1) one or more Mtb antigens, including "classical" Mtb antigens such as 85A, 85B and TB 10.4; and 2) at least one Mtb resuscitation antigen selected from Rv0867c, Rv1009, Rv1884c, Rv2389c, Rv2450c, Rv0288, Rv1009, Rv0685, Rv0824c, Rv1349, Rv2744c, Rv3347c, Rv1130, and Rv1169c. In some embodiments, the rBCG does not include the expression of the following combinations: classical antigens Rv1886c, Rv3804c; resuscitation antigens Rv0867c, Rv1884c, Rv2389c; and Mtb-specific antigen Rv3407. In some embodiments, the rBCG does not include the expression of the following combination: Rv3804c, Rv1886c, and Rv3407, or in addition with Rv3133c, and with the combination of Rv0867c, Rv188c, and Rv2389c. In some embodiments, the rBCG does not include the expression of e following combination: TB10.4, Ag85B, Ag85A, and Rv3407. In some embodiments, the cell not a rBCG.

The present disclosure also provides compositions comprising any one or more of the fusion proteins, Mtb antigens, nucleic acid molecules encoding Mtb antigens, including fusion proteins thereof, cells, and/or vectors and a pharmaceutically acceptable carrier. Compositions include, for example, pharmaceutical compositions. A pharmaceutically acceptable carrier refers to at least one component of a pharmaceutical preparation that is normally used for administration of active ingredients. As such, a carrier can contain any pharmaceutical excipient used in the art and any form of vehicle for administration. Carriers include, but are not limited to, phosphate buffered saline, physiological saline, water, citrate/sucrose/Tween formulations and emulsions such as, for example, oil/water emulsions.

The compositions can also include an active therapeutic agent and a variety of other pharmaceutically acceptable components. See Remington's Pharmaceutical Science (15th ed., Mack Publishing Company, Easton, Pennsylvania (1980)). The desired form depends on the intended mode of administration and therapeutic application. The compositions can also include, depending on the formulation desired, pharmaceutically acceptable, non-toxic carriers or diluents, which are defined as vehicles commonly used to formulate pharmaceutical compositions for animal or human administration. The diluent is selected so as not to affect the biological activity of the combination. Examples of such diluents include, but are not limited to, distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

Solid formulations of the compositions for oral administration can contain suitable carriers or excipients, such as corn starch, gelatin, lactose, acacia, sucrose, microcrystalline cellulose, kaolin, mannitol, dicalcium phosphate, calcium carbonate, sodium chloride, or alginic acid. Disintegrators that can be used include, without limitation, microcrystalline cellulose, corn starch, sodium starch glycolate, and alginic acid. Tablet binders that can be used include acacia, methylcellulose, sodium carboxymethylcellulose, polyvinylpyrrolidone (Povidone™) hydroxypropyl methylcellulose, sucrose, starch, and ethylcellulose. Lubricants that can be used include magnesium stearates, stearic acid, silicone fluid, talc, waxes, oils, and colloidal silica. Additional excipients include, for example, colorants, taste-masking agents, solubility aids, suspension agents, compressing agents, enteric coatings, sustained release aids, and the like.

In some embodiments, the compositions can be administered in the term of a depot injection or implant preparation, which can be formulated in such a manner as to permit a sustained release. An exemplary composition comprises any one or more of the compositions described herein formulated in aqueous buffer.

In some embodiments, liquid formulations of a pharmaceutical composition for oral administration prepared in water or other aqueous vehicles can contain various suspending agents such as methylcellulose, alginates, tragacanth, pectin, kelgin, carrageenan, acacia, polyvinylpyrrolidone, and polyvinyl alcohol. Liquid formulations of pharmaceutical compositions can also include solutions, emulsions, syrups and elixirs containing, together with the active compound(s), wetting agents, sweeteners, and coloring and flavoring agents. Various liquid and powder formulations of the pharmaceutical compositions can be prepared by conventional methods for inhalation into the lungs of the mammal to be treated.

In some embodiments, liquid formulations of a pharmaceutical composition for injection can comprise various carriers such as vegetable oils, dimethylacetamide, dimethylformamide, ethyl lactate, ethyl carbonate, isopropyl myristate, ethanol, polyols such as, for example, glycerol, propylene glycol, liquid polyethylene glycol, and the like. In some embodiments, the composition includes a citrate/sucrose/tween carrier. For intravenous injections, water soluble versions of the compositions can be administered by the drip method, whereby a pharmaceutical formulation containing the antifungal agent and a physiologically acceptable excipient is infused. Physiologically acceptable excipients can include, for example, 5% dextrose, 0.9% saline, Ringer's solution or other suitable excipients. A suitable insoluble form of the composition can be prepared and administered as a suspension in an aqueous base or a pharmaceutically acceptable oil base, such as an ester of a long chain fatty acid such as, for example, ethyl oleate.

The compositions can be, for example, injectable solutions, aqueous suspensions or solutions, non-aqueous suspensions or solutions, solid and liquid oral formulations, salves, gels, ointments, intradermal patches, creams, aerosols, lotions, tablets, capsules, sustained release formulations, and the like. In some embodiments, for topical applications, the pharmaceutical compositions can be formulated in a suitable ointment. In some embodiments, a topical semi-solid ointment formulation typically comprises a concentration of the active ingredient from about 1 to 20%, or from 5 to 10%, in a carrier, such as a pharmaceutical cream base, Some examples of formulations of a composition for topical use include, but are not limited to, drops, tinctures, lotions, creams, solutions, and ointments containing the active ingredient and various supports and vehicles.

Typically compositions are prepared as injectables, either as liquid solutions or suspensions; solid forms suitable for solution in, or suspension in, liquid vehicles prior to injection can also be prepared. The preparation also can be emulsified or encapsulated in liposomes or microparticles such as polylactide, polyglycolide, or copolymer for enhanced adjuvant effect (see Langer, Science, 1990, 249, 1527 and Hanes, Advanced Drug Delivery Reviews, 1997, 28, 97). A sterile injectable preparation such as, for example, a sterile injectable aqueous or oleaginous suspension can also be prepared. This suspension may be formulated according to techniques known in the art using suitable dispersing, wetting, and suspending agents. In some embodiments, the pharmaceutical composition can be delivered in a microencapsulation device so as to reduce or prevent a host immune response against the protein.

In some embodiments, any of the Mtb antigens, constructs, vectors, or cells described herein, or compositions comprising the same, can be combined into a single therapeutic or prophylactic regimen. For example, in some embodiments, an antigen matched BCG can be combined or used with a recombinant protein vaccine.

In some embodiments, any of the Mtb antigens, constructs, vectors, or cells described herein, or compositions comprising the same, can be administered to a mammal as an aerosol. In some embodiments, the aerosol inocula comprises saline. Conventional aerosol delivery devices include, but are not limited to, a pressurized metered dose inhaler (pMDI) and a dry power inhaler (DPI), both of which deliver a dry powder formulation, and nebulizers such as the PARI eFlow device, which delivers an aqueous dose as a fine mist. In some embodiments, the aerosol delivery device is a Pari eFlow portable electronic aerosol delivery platform attached to a delivery mask. In some embodiments, the average particle size is from about 1 µm to about 10 µm, from about 1 µm to about 5 µm, from about 3 µm to about 5 µm, from about 4 µm to about 5 µm, or from about 3.9 µm to about 4.9 µm. In some embodiments, the aerosol is in a volume from about 0.1 ml to about 5 ml, from about 0.1 ml to about 2 ml, from about 0.1 ml to about 1.5 ml, from about 0.5 ml to about 1.5 ml, from about 0.5 ml to about 1.2 ml, from about 0.7 ml to about 1.2 ml, or about 1 ml.

Effective doses of the compositions of the present disclosure, for the treatment of a condition vary depending upon many different factors, including means of administration, target site, physiological state of the subject, whether the subject is human or an animal, other medications administered, and whether treatment is prophylactic or therapeutic. Usually, the subject is a human but non-human mammals including transgenic mammals can also be treated.

In some embodiments, the compositions can be administered to a subject by injection intravenously, subcutaneously, intraperitoneally, intramuscularly, intramedullarily, intraventricularly, intraepidurally, intraarterially, intravascularly, intraarticularly, intrasynovially, intrasternally, intrathecally, intrahepatically, intraspinally, intratumorly, intracranially, enteral, intrapulmonary, transmucosal, intrauterine, sublingual, or locally at sites of inflammation or tumor growth by using standard methods. In some embodiments, the compositions can be administered to a subject by injection intravenously. Alternately, the compositions can be administered to a subject by routes including oral, nasal, ophthalmic, rectal, or topical. The most typical route of administration is intravascular, subcutaneous, or intramuscular, although other routes can be effective. In some embodiments, compositions are administered as a sustained release composition or device, such as a Medipad™ device. The composition can also be administered via the respiratory tract, for example, using a dry powder inhalation device, nebulizer, or a metered dose inhaler. The composition can also be administered by traditional syringes, needleless injection devices, "microprojectile bombardment gone guns," or other physical methods such as electroporation ("EP"), "hydrodynamic method", or ultrasound.

In some embodiments, the composition can be administered to a subject by sustained release administration, by such means as depot injections of erodible implants directly applied during surgery or by implantation of an infusion pump or a biocompatible sustained release implant into the subject. Alternately, the composition can be administered to a subject by injectable depot routes of administration, such as by using 1-, 3-, or 6-month depot injectable or biodegradable materials and methods, or by applying to the skin of the subject a transdermal patch containing the composition, and leaving the patch in contact with the subject's skin, generally for 1 to 5 hours per patch.

In some embodiments, the compositions comprise about 1 nanogram to about 10 mg of nucleic acid. In some embodiments, the compositions comprise: 1) at least 10, 15, 20, 25, 30, 35, 40, 45, 50, 55, 60, 65, 70, 75, 80, 85, 90, 95 or 100 nanograms, or at least 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995 or 1000 micrograms, or at least 1.5, 2, 2.5, 3, 3.5, 4, 4.5, 5, 5.5, 6, 6.5, 7, 7.5, 8, 8.5, 9, 9.5 or 10 mg or more; and 2) up to and including 15, 20, 25, 30, 35, 40, 45, 50, 55, 60, 65, 70, 75, 80, 85, 90, 95 or 100 nanograms, or up to and including 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, or 1000 micrograms, or up to and including 1.5, 2, 2.5, 3, 3.5, 4, 4.5, 5, 5.5, 6, 6.5, 7, 7.5, 8, 8.5, 9, 9.5 or 10 mg.

In some embodiments, the compositions comprise about 5 ng to about 10 mg of nucleic acid molecule. In some embodiments, the compositions comprise about 25 ng to about 5 mg of nucleic acid molecule. In some embodiments, the compositions contain about 50 ng to about 1 mg of nucleic acid molecule. In some embodiments, the compositions contain about 0.1 μg to about 500 μg of nucleic acid molecule. In some embodiments, the compositions contain about 1 μg to about 350 μg of nucleic acid molecule. In some embodiments, the compositions contain about 5 μg to about 250 μg of nucleic acid molecule. In some embodiments, the compositions contain about 10 μg to about 200 μg of nucleic acid molecule. In some embodiments, the compositions contain about 15 μg to about 150 μg of nucleic acid molecule. In some embodiments, the compositions contain about 20 μg to about 100 μg of nucleic acid molecule. In some embodiments, the compositions contain about 25 μg to about 75 μg of nucleic acid molecule. In some embodiments, the compositions contain about 30 μg to about 50 μg of nucleic acid molecule. In some embodiments, the compositions contain about 35 μg to about 40 μg of nucleic acid molecule. In some embodiments, the compositions contain about 100 μg to about 200 μg of nucleic acid molecule. In some embodiments, the compositions comprise about 10 μg to about 100 μg of nucleic acid molecule. In some embodiments, the compositions comprise about 20 μg to about 80 μg of nucleic acid molecule. In some embodiments, the compositions comprise about 25 μg to about 60 μg of nucleic acid molecule. In some embodiments, the compositions comprise about 30 ng to about 50 μg of nucleic acid molecule. In some embodiments, the compositions comprise about 35 ng to about 45 μg of nucleic acid molecule. In some embodiments, the compositions contain about 0.1 μg to about 500 μg of nucleic acid molecule. In some embodiments, the compositions contain about 1 μg to about 350 μg of nucleic acid molecule. In some embodiments, the compositions contain about 25 μg to about 250 μg of nucleic acid molecule. In some embodiments, the compositions contain about 100 μg to about 200 μg of nucleic acid molecule.

In some embodiments, the delivery platforms described herein can be used either in a single administration alone or in combinations as matched antigen prime-boost approaches. In addition, the use of these antigens in a single vector system, which is envisioned to be used as an antigen matched prime for a boost with any of the modalities above, including protein, viral vectors, nucleic acids, or others. For example, the same Mtb antigen construct can be used as both the prime and the boost. In other embodiments, a first Mtb antigen construct can be used as the prime and a second different Mtb antigen construct can be used as the boost (i.e., heterologous prime-boost). In some embodiments, the prime is a DNA or RNA (such as mRNA) prime and the boost is a viral vector boost. In some embodiments, the prime is a viral vector prime and the boost is a DNA or RNA (such as mRNA) boost.

The compositions can be formulated according to the mode of administration to be used. In cases where compositions are injectable pharmaceutical compositions, they are sterile, pyrogen free and particulate free. An isotonic formulation can be used. Generally, additives for isotonicity can include sodium chloride, dextrose, mannitol, sorbitol and lactose. In some cases, isotonic solutions such as phosphate buffered saline are suitable. Stabilizers include gelatin and albumin. In some embodiments, a vasoconstriction agent is added to the formulation.

The compositions can further comprise a pharmaceutically acceptable excipient. The pharmaceutically acceptable excipient can be functional molecules as vehicles, adjuvants, carriers, or diluents. The pharmaceutically acceptable excipient can be a transfection facilitating agent, which can include surface active agents, such as immune-stimulating complexes (ISCOMS), Freund's incomplete adjuvant, LPS analog including monophosphoryl lipid A, muramyl peptides, quinone analogs, vesicles such as squalene and squalane, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and more suitably, the poly-L-glutamate is present in the composition at a concentration less than 6 mg/ml. The transfection facilitating agent can also include surface active agents such as immune-stimulating complexes (ISCOMS), Freunds incomplete adjuvant, LPS analog including monophosphoryl lipid A, muramyl peptides, quinone analogs and vesicles such as squalene and squalane, and hyaluronic acid can also be used administered in conjunction with the genetic construct. In some embodiments, the plasmid compositions can also include a transfection facilitating agent such as lipids, liposomes, including lecithin liposomes or other liposomes known in the art, as a DNA-liposome mixture (see for example WO9324640), calcium ions, viral proteins, polyanions, polyanions, or nanoparticles, or other known transfection facilitating agents. In some embodiments, the transfection facilitating agent is a polyanion, polycation, including poly-L-glutamate (LGS), or lipid. Concentration of the transfection agent in the composition is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The pharmaceutically acceptable excipient may be an adjuvant. The adjuvant may be other genes that are expressed in alternative plasmid or are delivered as proteins in combination with the plasmid above. The adjuvant may be selected from the group consisting of: α-interferon (IFN-α), β-interferon (IFN-β), δ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, MHC, CD80, CD86 including IL-15 having the signal sequence deleted and optionally including the signal peptide from IgE. The adjuvant may be IL-12, IL-15, IL-28, CTACK, TECK, platelet derived growth factor (PDGF), TNFα, TNFβ, GM-CSF, epidermal growth factor (EGF), IL-1, IL-2, IL-4, IL-5, IL-6, IL-10, IL-12, IL-18, or a combination thereof.

Other genes which may be useful adjuvants include those encoding: MCP-1, MIP-1α, MIP-1p, L-selectin, P-selectin, E-selectin, CD34, GlyCAM-1, MadCAM-1, LFA-1, VLA-1, Mac-1, p150.95, PECAM, ICAM-1, ICAM-2, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRCS, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

The present disclosure also provides kits comprising any of the Mtb antigens, fragments thereof, fusion proteins, nucleic acid molecules, vectors, or cells, described herein. The kit can include, for example, container(s), package(s) or dispenser(s) along with labels and instructions for administration or use.

The present disclosure also provides methods of eliciting an immune response against *Mycobacterium tuberculosis* in a mammal comprising administering to the mammal an immunologically sufficient amount of one or more fusion proteins described herein. Any of the fusion proteins described herein can be administered. In some embodiments, the fusion protein comprises Rv3872-Rv1788-Rv3893c-Rv0285-Rv1818c-Rv0159c-Rv1172c (Construct A; see Table 2). In some embodiments, the fusion protein comprises Rv3873-Rv1387-Rv3892c (Construct B; see Table 4). In some embodiments, the fusion protein comprises Rv1789-Rv1800-Rv1039c (Construct C; see Table 4). In some embodiments, the fusion protein comprises Rv3017c-Rv3020c-Rv3019c-Rv3891c-Rv2346c-Rv3445c (Construct D; see Table 6). In some embodiments, the fusion protein comprises Rv3619c-Rv3875-Rv3874 (Construct E; see Table 6). In some embodiments, the fusion protein comprises Rv2719c-Rv0010c-Rv1872c (Construct F; see Table 8). In some embodiments, the fusion protein comprises Rv0012-Rv0990c-Rv0995 (Construct G; see Table 8).

The present disclosure also provides methods of eliciting an immune response against *Mycobacterium tuberculosis* in a mammal comprising administering to the mammal an immunologically sufficient amount of any of the Mtb compositions described herein. Any of the compositions comprising two or more Mtb antigens can be administered. In some embodiments, the composition comprises Rv3872, Rv1788, Rv3893c, Rv0285, Rv1818c, Rv0159c, and Rv1172c. In some embodiments, the composition comprises Rv3873, Rv1387, and Rv3892c. In some embodiments, the composition comprises Rv1789, Rv1800, and Rv1039c. In some embodiments, the composition comprises Rv3017c, Rv3020c, Rv3019c, Rv3891c, Rv2346c, and Rv3445c. In some embodiments, the composition comprises Rv3619c, Rv3875, and Rv3874. In some embodiments, the composition comprises Rv2719c, Rv0010c, and Rv1872c. In some embodiments, the composition comprises Rv0012, Rv0990c, and Rv0995.

The present disclosure also provides methods of eliciting an immune response against *Mycobacterium tuberculosis* in a mammal comprising administering to the mammal an immunologically sufficient amount of a composition comprising at least two or three Mtb antigens, and a pharmaceutically acceptable carrier; wherein the composition comprises at least one nucleic acid molecule encoding at least one of the Mtb antigens. Any of the compositions comprising a mixture of one or more Mtb antigen proteins and one of more nucleic acid molecules encoding one or more Mtb antigens described herein can be administered.

The fusion proteins and compositions described herein can be used to treat or prevent tuberculosis. In some embodiments, the method comprises administering to a human a therapeutically- or prophylactically-effective amount of any of the fusion proteins or compositions described herein such that the tuberculosis infection is diminished or prevented.

In some embodiments, the subject being treated will have been previously diagnosed as having tuberculosis. Such subjects will, thus, have been diagnosed as being in need of such treatment. Alternately, the treatment may be intended to prevent a tuberculosis infection in a subject that does not yet have tuberculosis or to a subject that is travelling to an area where tuberculosis is prevalent.

Treatment of a subject suffering from tuberculosis can be monitored using standard methods. Some methods entail determining a baseline value, for example, of an antibody level or profile in a subject, before administering a dosage of agent, and comparing this with a value for the profile or level after treatment. A significant increase such as, for example, greater than the typical margin of experimental error in repeat measurements of the same sample, expressed as one standard deviation from the mean of such measurements in value of the level or profile signals a positive treatment outcome (i.e., that administration of the agent has achieved a desired response). If the value for immune response does not change significantly, or decreases, a negative treatment outcome is indicated.

In some embodiments, a control value such as a mean and standard deviation, of level or profile is determined for a control population. Typically the individuals in the control population have not received prior treatment. Measured values of the level or profile in a subject after administering a therapeutic agent are then compared with the control value. A significant increase relative to the control value, such as greater than one standard deviation from the mean, signals a positive or sufficient treatment outcome. A lack of significant increase or a decrease signals a negative or insufficient treatment outcome. Administration of the therapeutic is generally continued while the level is increasing relative to the control value. As before, attainment of a plateau relative to control values is an indicator that the administration of treatment can be discontinued or reduced in dosage and/or frequency.

Inn other embodiments, a control value of the level or profile, such as a mean and standard deviation, is determined from a control population of individuals who have undergone treatment with a therapeutic agent and whose levels or profiles have plateaued in response to treatment. Measured values of levels or profiles in a subject are compared with the control value. If the measured level in a subject is not significantly different, such as by more than one standard deviation, from the control value, treatment can be discontinued. If the level in a subject is significantly below the control value, continued administration of agent is warranted. If the level in the subject persists below the control value, then a change in treatment may be indicated.

In some embodiments, a subject who is not presently receiving treatment but has undergone a previous course of treatment is monitored for antibody levels or profiles to determine whether a resumption of treatment is required. The measured level or profile in the subject can be compared with a value previously achieved in the subject after a previous course of treatment. A significant decrease relative to the previous measurement, such as greater than a typical margin of error in repeat measurements of the same sample, is an indication that treatment can be resumed. Alternately, the value measured in a subject can be compared with a control value (mean plus standard deviation) determined in a population of subjects after undergoing a course of treatment. Alternately, the measured value in a subject can be compared with a control value in populations of prophylactically treated subjects who remain free of symptoms of disease, or populations of therapeutically treated subjects who show amelioration of disease characteristics. In all of these cases, a significant decrease relative to the control level, such as more than a standard deviation, is an indicator that treatment should be resumed in a subject.

In some methods, a baseline measurement of antibody to a given antigen in the subject is made before administration, a second measurement is made soon thereafter to determine the peak antibody level, and one or more further measurements are made at intervals to monitor decay of antibody levels. When the level of antibody has declined to baseline or a predetermined percentage of the peak less baseline, such as 50%, 25% or 10%, administration of a further dosage of antigen is administered. In some embodiments, peak or subsequent measured levels less background are compared with reference levels previously determined to constitute a beneficial prophylactic or therapeutic treatment regime in other subjects. If the measured antibody level is significantly less than a reference level, such as less than the mean minus one standard deviation of the reference value in population of subjects benefiting from treatment, administration of an additional dosage of antigen is indicated.

Inn some embodiments, the subject(s) that can be treated by the above-described methods is an animal, including mammals and non-mammals. Suitable mammals, include, but are not limited to, humans, non-human primates, rodents (including rats, mice, hamsters and guinea pigs) cow, horse, sheep, badger, opossum, goat, pig, dog and cat. In most instances, the mammal is a human. In some embodiments, the non-mammal is a fish. Immunization of animals with any one or more of the vaccines described herein can prevent zoonotic transmission (i.e., transition of a disease, such as TB, from an animal to a human).

The present disclosure also provides fusion proteins for use in the preparation of a medicament for treating or preventing a *Mycobacterium tuberculosis* infection. Any of the fusion proteins described herein can be administered. In some embodiments, the fusion protein comprises Rv3872-Rv1788-Rv3893c-Rv0285-Rv1818c-Rv0159c-Rv1172c (Construct A; see Table 2). In some embodiments, the fusion protein comprises Rv3873-Rv1387-Rv3892c (Construct B; see Table 4). In some embodiments, the fusion protein comprises RV1789-RV1800-Rv1039c (Construct C; see Table 4). In some embodiments, the fusion protein comprises Rv3017c-Rv3020c-Rv3019c-Rv3891c-Rv2346c-Rv3445c (Construct D; see Table 6). In some embodiments, the fusion protein comprises Rv3619c-Rv3875-Rv3874 (Construct E; see Table 6). In some embodiments, the fusion protein comprises Rv2719c-Rv0010c-Rv1872c (Construct F; see Table 8). In some embodiments, the fusion protein comprises Rv0012-Rv0990c-Rv0995 (Construct G; see Table 8).

The present disclosure also provides fusion proteins for use in treating or preventing a *Mycobacterium tuberculosis* infection. Any of the fusion proteins described herein can be administered. In some embodiments, the fusion protein comprises Rv3872-Rv1788-Rv3893c-Rv0285-Rv1818c-Rv0159c-Rv1172c (Construct A; see Table 2). In some embodiments, the fusion protein comprises Rv3873-Rv1387-Rv3892c (Construct B; see Table 4). In some embodiments, the fusion protein comprises Rv1789-Rv1800-Rv1039c (Construct C; see Table 4). In some embodiments, the fusion protein comprises Rv3017c-Rv3020c-Rv3019c-Rv3891c-Rv2346c-Rv3445c (Construct D; see Table 6). In some embodiments, the fusion protein comprises Rv361.9c-Rv3875-Rv3874 (Construct E; see Table 6). In some embodiments, the fusion protein comprises Rv2719c-Rv0010c-Rv1872c (Construct F; see Table 8). In some embodiments, the fusion protein comprises Rv0012-Rv0990c-Rv0995 (Construct G; see Table 8).

The present disclosure also provides use of a fusion protein in the preparation of a medicament for treating or preventing a *Mycobacterium tuberculosis* infection. Any of the fusion proteins described herein can be administered. In some embodiments, the fusion protein comprises Rv3872-Rv1788-Rv3893c-Rv0285-Rv1818c-Rv0159c-Rv1172c (Construct A; see Table 2). In some embodiments, the fusion protein comprises Rv3873-Rv1387-Rv3892c (Construct B; see Table 4). In some embodiments, the fusion protein comprises Rv1789-Rv1800-Rv1039c (Construct C; see Table 4). In some embodiments, the fusion protein comprises Rv3017c-Rv3020c-Rv3019c-Rv3891c-Rv2346c-Rv3445c (Construct D; see Table 6). In some embodiments, the fusion protein comprises Rv3619c-Rv3875-Rv3874 (Construct E; see Table 6). In some embodiments, the fusion protein comprises Rv2719c-Rv0010c-Rv1872c (Construct F; see Table 8). In some embodiments, the fusion protein comprises Rv0012-Rv0990c-Rv0995 (Construct G; see Table 8).

The present disclosure also provides uses of a fusion protein in treating or preventing a *Mycobacterium tuberculosis* infection. Any of the fusion proteins described herein can be administered. In some embodiments, the fusion protein comprises Rv3872-Rv1788-Rv3893c-Rv0285-Rv1818c-Rv0159c-Rv1172c (Construct A; see Table 2). In some embodiments, the fusion protein comprises Rv3873-Rv1387-Rv3892c (Construct B; see Table 4). In some embodiments, the fusion protein comprises Rv1789-Rv1800-Rv1039c (Construct C; see Table 4). In some embodiments, the fusion protein comprises Rv3017c-Rv3020c-Rv3019c-Rv3891c-Rv2346c-Rv3445c (Construct D; see Table 6). In some embodiments, the fusion protein comprises Rv3619c-Rv3875-Rv3874 (Construct E; see Table 6). In some embodiments, the fusion protein comprises Rv2719c-Rv0010c-Rv1872c (Construct F; see Table 8). In some embodiments, the fusion protein comprises Rv0012-Rv0990c-Rv0995 (Construct G; see Table 8).

The present disclosure also provides compositions for use in the preparation of a medicament for treating or preventing a *Mycobacterium tuberculosis* infection. Any of the compositions comprising two or more Mtb antigens can be administered. In some embodiments, the composition comprises Rv3872, Rv1788, Rv3893c, Rv0285, Rv1818c, Rv0159c, and Rv1172c. In some embodiments, the composition comprises Rv3873, Rv1387, and Rv3892c. In some embodiments, the composition comprises Rv1789, Rv1800, and Rv1039c. In some embodiments, the composition comprises Rv3017c, Rv3020c, Rv3019c, Rv3891c, Rv2346c, and Rv3445c. In some embodiments, the composition comprises Rv3619c, Rv3875, and Rv3874. In some embodiments, the composition comprises Rv2719c, Rv0010c, and Rv1872c. In some embodiments, the composition comprises Rv0012, Rv0990c, and Rv0995.

The present disclosure also provides compositions for use in treating or preventing a *Mycobacterium tuberculosis* infection. Any of the compositions comprising two or more Mtb antigens can be administered. In some embodiments, the composition comprises Rv3872, Rv1788, Rv3893c, Rv0285, Rv1818c, Rv0159c, and Rv1172c. In some embodiments, the composition comprises Rv3873, Rv1387, and Rv3892c. In some embodiments, the composition comprises Rv1789, Rv1800, and Rv1039c. In some embodiments, the composition comprises Rv3017c, Rv3020c, Rv3019c, Rv3891c, Rv2346c, and Rv3445c. In some embodiments, the composition comprises Rv3619c, Rv3875, and Rv3874. In some embodiments, the composition comprises Rv2719c, Rv0010c, and Rv1872c. In some embodiments, the composition comprises Rv0012, Rv0990c, and Rv0995.

The present disclosure also provides uses of a composition in preparation of a medicament for treating or preventing a *Mycobacterium tuberculosis* infection. Any of the compositions comprising two or more Mtb antigens can be administered. In some embodiments, the composition comprises Rv3872, Rv1788, Rv3893c, Rv0285, Rv1818c, Rv0159c, and Rv1172c. In some embodiments, the composition comprises Rv3873, Rv1387, and Rv3892c. In some embodiments, the composition comprises Rv1789, Rv1800, and Rv1039c. In some embodiments, the composition comprises Rv3017c, Rv3020c, Rv3019c, Rv3891c, Rv2346c, and Rv3445c. In some embodiments, the composition comprises Rv3619c, Rv3875, and Rv3874. In some embodiments, the composition comprises Rv2719c, Rv0010c, and Rv1872c. In some embodiments, the composition comprises Rv0012, Rv0990c, and Rv0995.

The present disclosure also provides uses of a composition in treating or preventing a *Mycobacterium tuberculosis* infection. Any of the compositions comprising two or more Mtb antigens can be administered. In some embodiments, the composition comprises Rv3872, Rv1788, Rv3893c, Rv0285, Rv181.8c, Rv0159c, and Rv1172c. In some embodiments, the composition comprises Rv3873, Rv1387, and Rv3892c. In some embodiments, the composition comprises Rv1789, Rv1800, and Rv1039c. In some embodiments, the composition comprises Rv3017c, Rv3020c, Rv3019c, Rv3891c, Rv2346c, and Rv3445c. In some embodiments, the composition comprises Rv3619c, Rv3875, and Rv3874. In some embodiments, the composition comprises Rv2719c, Rv0010c, and Rv1872c. In some embodiments, the composition comprises Rv0012, Rv0990c, and Rv0995.

The present disclosure also provides compositions for use in the preparation of a medicament for treating or preventing a *Mycobacterium tuberculosis* infection, wherein the composition comprises at least two or three Mtb antigens, and a pharmaceutically acceptable carrier, wherein the composition comprises at least one nucleic acid molecule encoding at least one of the Mtb antigens.

The present disclosure also provides compositions for use in treating or preventing a *Mycobacterium tuberculosis* infection, wherein the composition comprises at least two or three Mtb antigens, and a pharmaceutically acceptable carrier, wherein the composition comprises at least one nucleic acid molecule encoding at least one of the Mtb antigens.

The present disclosure also provides uses of a composition in the preparation of a medicament for treating or preventing a *Mycobacterium tuberculosis* infection, wherein the composition comprises at least two or three Mtb antigens, and a pharmaceutically acceptable carrier, wherein the composition comprises at least one nucleic acid molecule encoding at least one of the Mtb antigens.

The present disclosure also provides uses of a composition in treating or preventing a *Mycobacterium tuberculosis* infection, wherein the composition comprises at least two or three Mtb antigens, and a pharmaceutically acceptable carrier, wherein the composition comprises at least one nucleic acid molecule encoding at least one of the Mtb antigens.

The present disclosure also provides any of the fusion proteins described herein, or any of the compositions described herein, or any of the cells described herein, or any of the vectors described herein, or any of the methods described herein, or any of the uses described herein, substantially as described herein.

Various modifications of the described subject matter, inn addition to those described herein, will be apparent to those skilled in the art from the foregoing description. Such modifications are also intended to fall within the scope of the appended claims Each reference (including, but not limited to, journal articles, U.S. and non-U.S. patents, patent application publications, international patent application publications, gene bank accession numbers, and the like) cited in the present application is incorporated herein by reference in its entirety.

What is claimed is:

1. A method of eliciting an immune response against *Mycobacterium tuberculosis* in a mammal comprising administering to the mammal an immunologically sufficient amount of a fusion protein comprising at least three Mtb PPE antigens chosen from Rv3873, Rv1387, Rv3892c, Rv1789, Rv1800, and Rv1039c, wherein: Rv3873 comprises the amino acid sequence set forth in SEQ ID NO:19, Rv1387 comprises the amino acid sequence set forth in SEQ ID NO: 21, Rv3892c comprises the amino acid sequence set forth in SEQ ID NO:23, Rv1789 comprises the amino acid sequence set forth in SEQ ID NO:25, Rv1800 comprises the amino acid sequence set forth in SEQ ID NO:27, and/or Rv1039c comprises the amino acid sequence set forth in SEQ ID NO:29.

2. The method of claim 1, wherein the fusion protein comprises Rv3873, Rv1387, and Rv3892c.

3. The method of claim 2, wherein the fusion protein comprises Rv3873-Rv1387-Rv3892c.

4. The method of claim 1, wherein the fusion protein comprises Rv1789, Rv1800, and Rv1039c.

5. The method of claim 4, wherein the fusion protein comprises Rv1789-Rv1800-Rv1039c.

6. A method of eliciting an immune response against *Mycobacterium tuberculosis* in a mammal comprising administering to the mammal an immunologically sufficient amount of a fusion protein comprising at least two Mtb PPE antigens chosen from Rv3873, Rv1387, Rv3892c, Rv1789, Rv1800, and Rv1039c, wherein: Rv3873 comprises the amino acid sequence set forth in SEQ ID NO:19, Rv1387 comprises the amino acid sequence set forth in SEQ ID NO: 21, Rv3892c comprises the amino acid sequence set forth in SEQ ID NO:23, Rv1789 comprises the amino acid sequence set forth in SEQ ID NO:25, Rv1800 comprises the amino acid sequence set forth in SEQ ID NO:27, and/or Rv1039c comprises the amino acid sequence set forth in SEQ ID NO:29, wherein when the fusion protein comprises Rv3873, the fusion protein does not comprise Rv1789, and wherein when the fusion protein comprises Rv1789, the fusion protein does not comprise Rv3873.

7. A method of eliciting an immune response against *Mycobacterium tuberculosis* in a mammal comprising administering to the mammal an immunologically sufficient amount of a fusion protein comprising at least two Mtb PPE antigens chosen from an Rv3873 fragment, Rv1387, Rv3892c, an Rv1789 fragment, Rv1800, and Rv1039c, wherein: the Rv3873 fragment comprises the amino acid sequence set forth in SEQ ID NO:19, Rv1387 comprises the amino acid sequence set forth in SEQ ID NO:21, Rv3892c comprises the amino acid sequence set forth in SEQ ID NO:23, the Rv1789 fragment comprises the amino acid sequence set forth in SEQ ID NO: 25, Rv1800 comprises the amino acid sequence set forth in SEQ ID NO:27, and/or Rv1039c comprises the amino acid sequence set forth in SEQ ID NO:29, and when the fusion protein comprises an Rv3873 fragment, the fusion protein does not comprise an Rv1789 fragment, and wherein when the fusion protein comprises an Rv1789 fragment, the fusion protein does not comprise an Rv3873 fragment.

\* \* \* \* \*